United States Patent
Pajouhesh et al.

(10) Patent No.: US 8,133,998 B2
(45) Date of Patent: Mar. 13, 2012

(54) BICYCLIC PYRIMIDINE DERIVATIVES AS CALCIUM CHANNEL BLOCKERS

(75) Inventors: Hassan Pajouhesh, West Vancouver (CA); Hossein Pajouhesh, Coquitlam (CA); Yanbing Ding, Richmond (CA); Jason Tan, Vancouver (CA); Mike Grimwood, North Vancouver (CA); Francesco Belardetti, Vancouver (CA); Ramesh Kaul, Burnaby (CA); Richard Holland, Vancouver (CA); Navjot Chahal, Vancouver (CA)

(73) Assignee: Zalicus Pharmaceuticals, Ltd., Vancouver, British Columbia (CA)

( * ) Notice: Subject to any disclaimer, the term of this patent is extended or adjusted under 35 U.S.C. 154(b) by 937 days.

(21) Appl. No.: 12/118,492

(22) Filed: May 9, 2008

(65) Prior Publication Data
US 2008/0280900 A1 Nov. 13, 2008

Related U.S. Application Data

(60) Provisional application No. 60/917,041, filed on May 9, 2007.

(51) Int. Cl.
C07D 491/00 (2006.01)
C07D 333/00 (2006.01)
C07D 333/52 (2006.01)
C07D 333/38 (2006.01)

(52) U.S. Cl. ............... 544/278; 549/49; 549/51; 549/71
(58) Field of Classification Search .................. 544/278; 549/49, 51, 71
See application file for complete search history.

(56) References Cited

U.S. PATENT DOCUMENTS

| | | | |
|---|---|---|---|
| 6,159,962 A * | 12/2000 | Steiner et al. ............ | 514/211.08 |
| 6,387,912 B1 | 5/2002 | Steiner et al. | |
| 2003/0004172 A1 | 1/2003 | Harter et al. | |
| 2003/0086980 A1 | 5/2003 | Shin et al. | |
| 2003/0087799 A1 | 5/2003 | Wolfart et al. | |
| 2003/0125269 A1 | 7/2003 | Li | |
| 2004/0038994 A1 | 2/2004 | Wilson | |
| 2004/0197825 A1 | 10/2004 | Karicheti et al. | |
| 2005/0004126 A1 | 1/2005 | Andrianjara et al. | |
| 2006/0003985 A1 | 1/2006 | Renger et al. | |
| 2006/0025397 A1 | 2/2006 | Shin et al. | |

FOREIGN PATENT DOCUMENTS

| | | |
|---|---|---|
| CA | 2520628 | 10/2004 |
| WO | WO-93/13664 | 7/1993 |
| WO | WO-03/007953 | 1/2003 |
| WO | WO-04/000311 | 12/2003 |
| WO | WO-2005/033288 | 4/2005 |
| WO | WO-2005/077082 | 8/2005 |
| WO | WO-2005/086971 | 9/2005 |
| WO | WO-2005/105760 | 11/2005 |
| WO | WO-2006/023881 | 3/2006 |
| WO | WO-2006/024160 | 3/2006 |
| WO | WO-2006/098969 | 9/2006 |
| WO | WO-2007/120729 | 10/2007 |
| WO | WO-2008/007835 | 1/2008 |

OTHER PUBLICATIONS

Alfred Burger, Isosterism and Bioisosterism in Drug Design, in Progress in Drug Research 287-328 (Ernst Jucker, ed., Birkhauser Verlag, 1991).*
George Patani & Edmond LaVoie, Bioisosterism: A Rational Approach in Drug Design, 96 Chem. Rev. 3147 (1996).*
Augustine et al., Annu. Rev. Neurosci. (1987) 10:633-693.
Catterall, Annu. Rev. Cell Dev. Biol. (2000) 16:521-555.
Dogrul et al., Pain (2003) 105:159-168.
Gomora et al., Mol. Pharmacol. (2001) 60:1121-1132.
Heady et al., Jpn. J. Pharmacol. (2001) 85:339-350.
Huguenard, Annu. Rev. Physiol. (1996) 58:329-348.
Kim et al., Mol. Cell Neurosci. (2001) 18(2):235-245.
Miller, Science (1987) 235:46-52.
Su et al., J. Neurosci. (2002) 22:3645-3655.
Sui et al., British Journal of Urology International (2007) 99(2):436-441.
International Search Report and Written Opinion for PCT/CA2008/000904, mailed Aug. 27, 2008, 7 pages.
Doddareddy et al., Bioorganic & Medicinal Chemistry Ltrs. (2007) 15:1091-1105. Jo et al., Bioorganic & Medicinal Chemistry Ltrs. (2007) 15:365-373.
Modica et al., European Journal Medical Chemistry (2000) 35:1065-1079.

* cited by examiner

Primary Examiner — Karlheinz R Skowronek
Assistant Examiner — Sean Basquill
(74) Attorney, Agent, or Firm — Clark & Elbing LLP

(57) ABSTRACT

Methods and compounds effective in ameliorating conditions characterized by unwanted calcium channel activity, particularly unwanted T-type calcium channel activity are disclosed. Specifically, a series of compounds containing thienopyrimidine or oxoquinazoline derivatives are disclosed of the general formula (1) or formula (2) where X is a linker and Y is an aromatic moiety or N(R5)(R6).

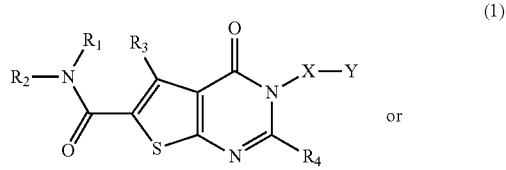

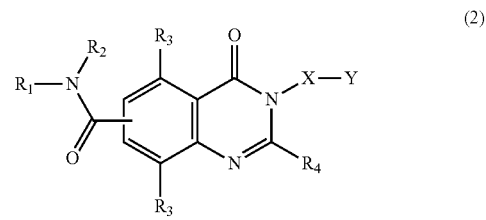

42 Claims, No Drawings

BICYCLIC PYRIMIDINE DERIVATIVES AS CALCIUM CHANNEL BLOCKERS

CROSS-REFERENCE TO RELATED APPLICATIONS

This application claims priority to U.S. Provisional Application Ser. No. 60/917,041, filed May 9, 2007, the contents of which are incorporated herein by reference.

TECHNICAL FIELD

The invention relates to compounds useful in treating conditions associated with calcium channel function, and particularly conditions associated with T-type calcium channel activity. More specifically, the invention concerns compounds containing either thienopyrimidine or oxoquinazoline derivatives that are useful in treatment of conditions such as cardiovascular disease, epilepsy and pain.

BACKGROUND ART

The entry of calcium into cells through voltage-gated calcium channels mediates a wide variety of cellular and physiological responses, including excitation-contraction coupling, hormone secretion and gene expression (Miller, R. J., *Science* (1987) 235:46-52; Augustine, G. J. et al., *Annu Rev Neurosci* (1987) 10: 633-693). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter, which also affects neurite outgrowth and growth cone migration in developing neurons.

Calcium channels mediate a variety of normal physiological functions, and are also implicated in a number of human disorders. Examples of calcium-mediated human disorders include but are not limited to congenital migraine, cerebellar ataxia, angina, epilepsy, hypertension, ischemia, and some arrhythmias. The clinical treatment of some of these disorders has been aided by the development of therapeutic calcium channel antagonists (e.g., dihydropyridines, phenylalkyl amines, and benzothiazapines all target L-type calcium channels) (Janis, R. J. & Triggle, D. J., In Calcium Channels: Their Properties, Functions, Regulation and Clinical Relevance (1991) CRC Press, London).

Native calcium channels have been classified by their electrophysiological and pharmacological properties into T-, L-, N-, P/Q- and R-types (reviewed in Catterall, W., *Annu Rev Cell Dev Biol* (2000) 16: 521-555; Huguenard, J. R., *Annu Rev Physiol* (1996) 58: 329-348). T-type (or low voltage-activated) channels describe a broad class of molecules that transiently activate at negative potentials and are highly sensitive to changes in resting potential.

The L-, N- and P/Q-type channels activate at more positive potentials (high voltage-activated) and display diverse kinetics and voltage-dependent properties (Catterall (2000); Huguenard (1996)). T-type channels can be distinguished by having a more negative range of activation and inactivation, rapid inactivation, slow deactivation, and smaller single-channel conductances. There are three subtypes of T-type calcium channels that have been molecularly, pharmacologically, and elecrophysiologically identified: these subtypes have been termed $\alpha_{1G}$, $\alpha_{1H}$, and $\alpha_{1I}$ (alternately called Cav 3.1, Cav 3.2 and Cav 3.3 respectively).

T-type calcium channels are involved in various medical conditions. In mice lacking the gene expressing the $\alpha_{1G}$ subunit, resistance to absence seizures was observed (Kim, C. et al., *Mol Cell Neurosci* (2001) 18(2): 235-245). Other studies have also implicated the $\alpha_{1H}$ subunit in the development of epilepsy (Su, H. et al., *J Neurosci* (2002) 22: 3645-3655). There is strong evidence that some existing anticonvulsant drugs, such as ethosuximide, function through the blockade of T-type channels (Gomora, J. C. et al., *Mol Pharmacol* (2001) 60: 1121-1132).

Low voltage-activated calcium channels are highly expressed in tissues of the cardiovascular system. Mibefradil, a calcium channel blocker 10-30 fold selective for T-type over L-type channels, was approved for use in hypertension and angina. It was withdrawn from the market shortly after launch due to interactions with other drugs (Heady, T. N., et al., *Jpn J Pharmacol.* (2001) 85:339-350).

Growing evidence suggests T-type calcium channels are also involved in pain (see for example: US Patent Application No. 2003/086980; PCT Patent Application Nos. WO 03/007953 and WO 04/000311). Both mibefradil and ethosuximide have shown anti-hyperalgesic activity in the spinal nerve ligation model of neuropathic pain in rats (Dogrul, A., et al., *Pain* (2003) 105:159-168). In addition to cardiovascular disease, epilepsy (see also US Patent Application No. 2006/025397), and chronic and acute pain, T-type calcium channels have been implicated in diabetes (US Patent Application No. 2003/125269), certain types of cancer such as prostate cancer (PCT Patent Application Nos. WO 05/086971 and WO 05/77082), sleep disorders (US Patent Application No. 2006/003985), Parkinson's disease (US Patent Application No. 2003/087799); psychosis such as schizophrenia (US Patent Application No. 2003/087799), overactive bladder (Sui, G.-P., et al., *British Journal of Urology International* (2007) 99(2): 436-441; see also US 2004/197825) and male birth control.

All patents, patent applications and publications are herein incorporated by reference in their entirety.

DISCLOSURE OF THE INVENTION

The invention relates to compounds useful in treating conditions modulated by calcium channel activity and in particular conditions mediated by T-type channel activity. The compounds of the invention are bicyclic pyrimidine derivatives with structural features that enhance the calcium channel blocking activity of the compounds. Thus, in one aspect, the invention is directed to a method of treating conditions mediated by calcium channel activity by administering to patients in need of such treatment at least one compound of formula (1) or formula (2):

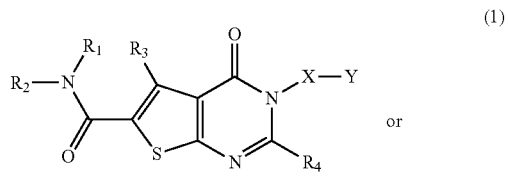

or

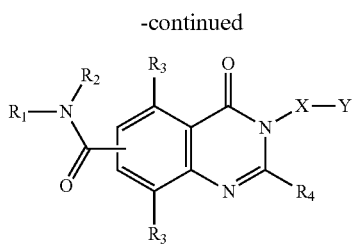

(2)

or a pharmaceutically acceptable salt or conjugate thereof, wherein each $R_1$ and $R_2$ are independently, H, or an optionally substituted alkyl (1-6C), alkenyl (2-6C), alkynyl (2-6C), heteroalkyl (2-6C), heteroalkenyl (2-6C), heteroalkynyl (2-6C), aryl (6-10C), heteroaryl (5-12C), or C6-C12-aryl-C1-C6-alkyl; or $R_1$ and $R_2$ together with N to which they are attached form an optionally substituted 3-8 membered heterocyclic ring or 5-12 membered heteroaromatic ring;

each $R_3$ and $R_4$ are independently H, halo or an optionally substituted alkyl (1-3C) or heteroalkyl (1-3C);

X is an optionally substituted alkylene (1-3C) or heteroalkylene (1-3C);

Y is Ar or $N(R_5)(R_6)$ wherein Ar is an optionally substituted aryl (6-10C) or heteroaryl (5-12C) and $R_5$ and $R_6$ are independently, H, or an optionally substituted alkyl (1-6C), alkenyl (2-6C), alkynyl (2-6C), heteroalkyl (2-6C), heteroalkenyl (2-6C), heteroalkynyl (2-6C), aryl (6-10C), heteroaryl (5-12C), or C6-C12-aryl-C1-C6-alkyl; or $R_5$ and $R_6$ together with N to which they are attached form an optionally substituted 3-8 membered heterocyclic ring or 5-12 membered heteroaromatic ring;

wherein the optional substituents on each X, Ar, $R_1$, $R_2$, $R_3$, $R_4$ and $R_5$ are independently selected from halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from alkyl (1-6C), alkenyl (2-6C), alkynyl (2-6C), heteroalkyl (2-6C) heteroalkenyl (2-6C), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), or heteroalkynyl (2-6C); and wherein the optional substituent on X, $R^1$, $R^2$, $R^5$ and $R^6$ may further be selected from =O and =NOR';

and wherein optional substituents on a heterocyclic ring formed with $R^1$ and $R^2$ or $R^5$ and $R^6$ may independently be selected from =O, =NOR', halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), heteroalkynyl (2-6C), or aryl (6-10C), heteroaryl (5-12C), or C6-C12-aryl-C1-C6-alkyl;

with the provisos that for compounds of formula (1): when Y is $N(R_5)(R_6)$, a carbon atom in X or Y that is adjacent to the N in Y is substituted by =O;

and when Y is Ar, then neither $R_1$ nor $R_2$ is arylalkyl.

The invention is also directed to the use of compounds of formula (1) and formula (2) for the preparation of medicaments for the treatment of conditions requiring modulation of calcium channel activity, and in particular T-type calcium channel activity. In another aspect, the invention is directed to pharmaceutical compositions containing compounds of formula (1) and formula (2) and to the use of these compositions for treating conditions requiring modulation of calcium channel activity, and particularly T-type calcium channel activity. The invention is also directed to compounds of formula (1) and formula (2) useful to modulate calcium channel activity, particularly T-type channel activity.

DETAILED DESCRIPTION

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. Typically, the alkyl, alkenyl and alkynyl groups contain 1-8C (alkyl) or 2-8C (alkenyl or alkynyl). In some embodiments, they contain 1-6C, 1-4C, 1-3C or 1-2C (alkyl); or 2-6C, 2-4C or 2-3C (alkenyl or alkynyl). Further, any hydrogen atom on one of these groups can be replaced with a halogen atom, and in particular a fluoro or chloro, and still be within the scope of the definition of alkyl, alkenyl and alkynyl. For example, $CF_3$ is a 1C alkyl. These groups may be also be substituted by other substituents.

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In preferred embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In preferred embodiments, the heteroatom is O or N. For greater certainty, to the extent that alkyl is defined as 1-6C, then the corresponding heteroalkyl contains 2-6 C, N, O, or S atoms such that the heteroalkyl contains at least one C atom and at least one heteroatom. Similarly, when alkyl is defined as 1-6C or 1-4C, the heteroform would be 2-6C or 2-4C respectively, wherein at least one C is replaced by O, N or S. Accordingly, when alkenyl or alkynyl is defined as 2-6C (or 2-4C), then the corresponding heteroform would also contain 2-6 C, N, O, or S atoms (or 2-4) since the heteroalkenyl or heteroalkynyl contains at least one carbon atom and at least one heteroatom. Further, heteroalkyl, heteroalkenyl or heteroalkynyl substituents may also contain one or more carbonyl groups. Examples of heteroalkyl, heteroalkenyl and heteroalkynyl groups include $CH_2OCH_3$, $CH_2N(CH_3)_2$, $CH_2OH$, $(CH_2)_nNR_2$, OR, COOR, $CONR_2$, $(CH_2)_nOR$, $(CH_2)_nCOR$, $(CH_2)_nCOOR$, $(CH_2)_nSR$, $(CH_2)_nSOR$, $(CH_2)_nSO_2R$, $(CH_2)_nCONR_2$, $NRCOR$, $NRCOOR$, $OCONR_2$, OCOR and the like wherein the group contains at least one C and the size of the substituent is consistent with the definition of alkyl, alkenyl and alkynyl.

As used herein, the terms "alkylene," "alkenylene" and "alkynylene" refers to divalent groups having a specified size, typically 1-2C, 1-3C, 1-4C, 1-6C or 1-8C for the saturated groups and 2-3C, 2-4C, 2-6C or 2-8C for the unsaturated groups. They include straight-chain, branched-chain and cyclic forms as well as combinations of these, containing only C and H when unsubstituted. Because they are divalent, they can link together two parts of a molecule, as exemplified by X in formula (1) and formula (2). Examples include methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example.

Heteroalkylene, heteroalkenylene and heteroalkynylene are similarly defined as divalent groups having a specified size, typically 2-3C, 2-4C, 2-6C or 2-8C for the saturated groups and 2-3C, 2-4C, 2-6C or 2-8C for the unsaturated groups. They include straight chain, branched chain and cyclic groups as well as combinations of these, and they further contain at least one carbon atom but also contain one or more O, S or N heteroatoms or combinations thereof within the backbone residue, whereby each heteroatom in the heteroalkylene, heteroalkenylene or heteroalkynylene group replaces one carbon atom of the alkylene, alkenylene or alkynylene group to which the heteroform corresponds. As is understood in the art, these heteroforms do not contain more than three contiguous heteroatoms.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, 2-, 3- or 4-pyridyl, indolyl, 2- or 4-pyrimidyl, pyridazinyl, benzothiazolyl or benzimidazolyl. Even more particularly, such moiety is phenyl, pyridyl, or pyrimidyl and even more particularly, it is phenyl.

"O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of 1-8C, 1-6C or more particularly 1-4C or 1-3C when saturated or 2-8C, 2-6C, 2-4C or 2-3C when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(6-12C)alkyl(1-8C), aryl(6-12C)alkenyl(2-8C), or aryl(6-12C)alkynyl(2-8C), plus the heteroforms. A typical example is phenylmethyl, commonly referred to as benzyl.

Typical optional substituents on aromatic or heteroaromatic groups include independently halo, CN, $NO_2$, $CF_3$, $OCF_3$, COOR', $CONR'_2$, OR', SR', SOR', $SO_2R'$, $NR'_2$, NR'(CO)R', NR'C(O)OR', $NR'C(O)NR'_2$, $NR'SO_2NR'_2$, or $NR'SO_2R'$, wherein each R' is independently H or an optionally substituted group selected from alkyl, alkenyl, alkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group, are typically selected from the same list of substituents suitable for aromatic or heteroaromatic groups and may further be selected from =O and =NOR' where R' is H or an optionally substituted group selected from alkyl, alkenyl, alkynyl, heteroaryl, and aryl (all as defined above).

Halo may be any halogen atom, especially F, Cl, Br, or I, and more particularly it is fluoro, or chloro.

In general, any alkyl, alkenyl, alkynyl, or aryl (including all heteroforms defined above) group contained in a substituent may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included.

X may independently be an optionally substituted alkylene or heteroalkylene (as defined above). In a more particular embodiment, X may independently be an optionally substituted ethylene or an optionally substituted methylene, and even more particularly, the optional substituent can be a carbonyl. In specific embodiments, X is $CH_2C=O$ or $CH_2CH_2$ or $CH(CH_3)C=O$ or $CH_2$.

In some embodiments, Y in compounds of Formula (1) or (2) is an optionally substituted aryl moiety or an optionally substituted heteroaryl moiety. In more particular embodiments, Y is an optionally substituted phenyl ring. For example, Y may be unsubstituted phenyl or a halogenated phenyl such as 2-, 3- or 4-fluorophenyl and more particularly 2-fluorophenyl. In other embodiments, Y is $N(R_5)(R_6)$. In such embodiments, $R_5$ and $R_6$ may be the same or different and may independently by H, or an optionally substituted alkyl, alkenyl, alkynyl, heteroalkyl, heteroalkenyl, heteroalkynyl, aryl, heteroaryl or arylalkyl. In more particular embodiments, $R_5$ and $R_6$ are H or an optionally substituted alkyl or heteroalkyl and even more particularly $R_5$ and $R_6$ are H or an optionally substituted alkyl. For example, $R_5$ and $R_6$ may be H, or an optionally substituted methyl, ethyl, butyl, cyclohexyl, cyclopentyl, cyclopropyl, or phenyl. In particular embodiments, optional substituents include halo and methyl and trifluoromethyl. In other embodiments, $R_5$ and $R_6$ together with N in $NR_5R_6$ may form an optionally substituted 3-8 membered heterocyclic ring or 5-12 membered heteroaromatic ring such as a pyrrolidinyl, piperidinyl, piperazinyl, morpholino or pyridinyl or pyrrolyl. In more particular embodiments, $R_5$ and $R_6$ together form an optionally substituted heterocyclic ring. Without limiting the generality of the substituents as defined herein, examples of more particular substituents include halo, methyl, trifluoromethyl, and =O as substituents on such heterocyclic ring.

$R_1$ and $R_2$ are independently H or an optionally substituted alkyl, alkenyl, alkynyl, heteroalkyl, heteroalkenyl, heteroalkynyl, aryl, heteroaryl or arylalkyl. In more particular embodiments, $R_1$ and $R_2$ are H or an optionally substituted alkyl, heteroalkyl, aryl or arylalkyl. Further, $R_1$ and $R_2$ may be the same or different. For example, $R_1$ and $R_2$ may independently be H or methyl, butyl, phenyl or benzyl. In other embodiments, $R_1$ and $R_2$ together form an optionally substituted 3-8 membered heterocyclic or 5-12 membered heteroaromatic ring such as a pyrrolidinyl, piperidinyl, piperazinyl, morpholino or pyridinyl or pyrrolyl. Without limiting the generality of the substituents defined herein, examples of even more particular substitutents on such optionally substituted ring include halo, or optionally substituted alkyl, heteroalkyl, aryl, heteroaryl, or arylalkyl. More specific examples of substituents on such a heterocyclic ring include fluoro, methyl, trifluoromethyl, optionally substituted phenyl, benzyl, and morpholino. Even more specific examples include benzoyl, fluoro-benzoyl, phenyl, chlorophenyl, trifluoromethylphenyl, butylphenyl, methoxyphenyl, nitrophenyl, and methylphenyl.

Each $R_3$ and $R_4$ is independently H, halo or an optionally substituted alkyl (1-3C) or heteroalkyl (1-3C). In particular embodiments, $R_3$ is H or methyl. In a more particular embodiment, $R_3$ is methyl and the compound is of formula (1). In another embodiment $R_3$ is H and the compound is of formula (2). In some embodiments, $R_4$ is H.

In compounds of formula (2), the amide chain on the quinazolinone may be at the six position as shown in formula (3) or in the seven position as shown in formula (4):

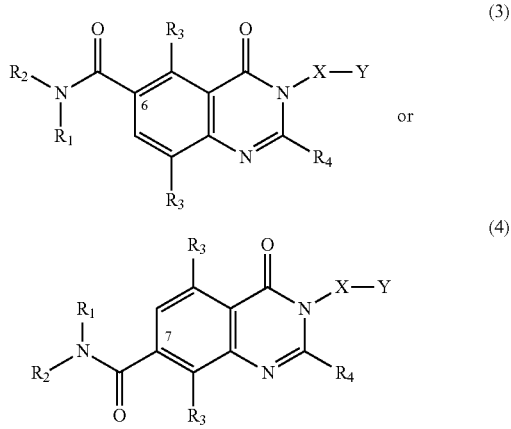

In some preferred embodiments, two or more of the particularly described groups are combined into one compound: it is often suitable to combine one of the specified embodiments of one feature as described above with a specified embodiment or embodiments of one or more other features as described above. For example, a specified embodiment includes X being $CH_2C=O$, and another specified embodiment has Y is $N(R_5)(R_6)$ where $R_5$ and $R_6$ form a heterocyclic ring such as a piperidinyl. Thus one preferred embodiment combines both of these features together, i.e., X is $CH_2C=O$ in combination with $Y=NR_5R_6$, where $NR_5R_6$ is an optionally substituted piperidinyl. In some specific embodiments, $R_3$ is H and in others $R_3$ is methyl. Thus additional preferred embodiments include $R_3$ as H in combination with any of the preferred combinations set forth above; other preferred combinations include $R_3$ as methyl in combination with any of the preferred combinations set forth above.

The compounds of the invention may have ionizable groups so as to be capable of preparation as salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed.

Compounds of formula (1) and formula (2) are also useful for the manufacture of a medicament useful to treat conditions characterized by undesired T-type calcium channel activities.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to the compounds of formula (1) and formula (2) when modified so as to be included in a conjugate of this type.

Modes of Carrying Out the Invention

The compounds of formula (1) and formula (2) are useful in the methods of the invention and, while not bound by theory, are believed to exert their desirable effects through their ability to modulate the activity of calcium channels, particularly the activity of T-type calcium channels. This makes them useful for treatment of certain conditions where modulation of T-type calcium channels is desired, including: cardiovascular disease; epilepsy; diabetes; certain types of cancer such as prostate cancer; pain, including both chronic and acute pain; sleep disorders; Parkinson's disease; psychosis such as schizophrenia; overactive bladder and male birth control.

Cardiovascular disease as used herein includes but is not limited to hypertension, pulmonary hypertension, arrhythmia (such as atrial fibrillation and ventricular fibrillation), congestive heart failure, and angina pectoris.

Epilepsy as used herein includes but is not limited to partial seizures such as temporal lobe epilepsy, absence seizures, generalized seizures, and tonic/clonic seizures.

Acute pain as used herein includes but is not limited to nociceptive pain and post-operative pain. Chronic pain includes but is not limited by: peripheral neuropathic pain such as post-herpetic neuralgia, diabetic neuropathic pain, neuropathic cancer pain, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome; inflammatory pain such as rheumatoid arthritis and endometriosis; headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

For greater certainty, in treating osteoarthritic pain, joint mobility will also improve as the underlying chronic pain is reduced. Thus, use of compounds of the present invention to treat osteoarthritic pain inherently includes use of such compounds to improve joint mobility in patients suffering from osteoarthritis.

It is known that calcium channel activity is involved in a multiplicity of disorders, and particular types of channels are associated with particular conditions. The association of T-type channels in conditions associated with neural transmission would indicate that compounds of the invention which target T-type receptors are most useful in these conditions. Many of the members of the genus of compounds of formula (1) and formula (2) exhibit high affinity for T-type channels. Thus, as described below, they are screened for their ability to interact with T-type channels as an initial indication of desirable function. It is particularly desirable that the compounds exhibit $IC_{50}$ values of <1 µM. The $IC_{50}$ is the concentration which inhibits 50% of the calcium, barium or other permeant divalent cation flux at a particular applied potential.

In order to be maximally useful in treatment, it is also helpful to assess the side reactions which might occur. Thus, in addition to being able to modulate a particular calcium channel, it is desirable that the compound has very low activity with respect to the hERG $K^+$ channel which is expressed in the heart. Compounds that block this channel with high potency may cause reactions which are fatal. Thus, for a compound that modulates the calcium channel, it is preferred that the hERG $K^+$ channel is not inhibited. Similarly, it would be undesirable for the compound to inhibit cytochrome p450 since this enzyme is required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The compounds of the invention modulate the activity of calcium channels; in general, said modulation is the inhibition of the ability of the channel to transport calcium. As described below, the effect of a particular compound on calcium channel activity can readily be ascertained in a routine assay whereby the conditions are arranged so that the channel is activated, and the effect of the compound on this activation (either positive or negative) is assessed. Typical assays are described hereinbelow in Example 14.

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol.* (1993) 9:109-115; Salemme, F. R., et al., *Structure* (1997) 5:319-324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, e.g., the N-type channel. In addition, using standard screening protocols, the libraries may be screened for compounds that block additional channels or receptors such as sodium channels, potassium channels and the like.

Methods of performing these screening functions are well known in the art. These methods can also be used for individually ascertaining the ability of a compound to agonize or antagonize the channel. Typically, the channel to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the channel is measured in the presence of calcium, barium or other permeant divalent cation and the ability of the compound to interfere with the signal generated is measured using standard techniques. In more detail, one method involves the binding of radiolabeled agents that interact with the calcium channel and subsequent analysis of equilibrium binding measurements including, but not limited to, on rates, off rates, $K_d$ values and competitive binding by other molecules.

Another method involves the screening for the effects of compounds by electrophysiological assay whereby individual cells are impaled with a microelectrode and currents through the calcium channel are recorded before and after application of the compound of interest.

Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.03 Hz. Finally, resting channel blockers would diminish the peak current amplitude during the very first depolarization after drug application without additional inhibition during the depolarization.

Accordingly, a library of compounds of formula (1) and formula (2) can be used to identify a compound having a desired combination of activities that includes activity against at least one type of calcium channel. For example, the library can be used to identify a compound having a suitable level of activity on T-type calcium channels while having minimal activity on HERG K+ channels.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa., incorporated herein by reference.

In general, for use in treatment, the compounds of formula (1) and formula (2) may be used alone, as mixtures of two or more compounds of formula (1) or formula (2) or in combination with other pharmaceuticals. An example of other potential pharmaceuticals to combine with the compounds of formula (1) or formula (2) would include pharmaceuticals for the treatment of the same indication but having a different mechanism of action from T-type calcium channel blocking. For example, in the treatment of pain, a compound of formula (1) or formula (2) may be combined with another pain relief treatment such as an NSAID, or a compound which selectively inhibits COX-2, or an opioid, or an adjuvant analgesic such as an antidepressant. Another example of a potential pharmaceutical to combine with the compounds of formula (1) or formula (2) would include pharmaceuticals for the treatment of different yet associated or related symptoms or indications. Depending on the mode of administration, the compounds will be formulated into suitable compositions to permit facile delivery.

The compounds of the invention may be prepared and used as pharmaceutical compositions comprising an effective amount of at least one compound of formula (1) or formula (2) admixed with a pharmaceutically acceptable carrier or excipient, as is well known in the art. Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.01-15 mg/kg, preferably 0.1-10 mg/kg. However, dosage levels are highly dependent on the nature of the condition, drug efficacy, the condition of the patient, the judgment of the practitioner, and the frequency and mode of administration. Optimization of the dosage for a particular subject is within the ordinary level of skill in the art.

Synthesis of the Invention Compounds

The following reaction schemes and examples are intended to illustrate the synthesis of a representative number of compounds. Accordingly, the following examples are intended to illustrate but not to limit the invention. Additional compounds not specifically exemplified may be synthesized using conventional methods in combination with the methods described hereinbelow.

Example 1

Synthesis of 2-(6-(4-(3,4-dichlorophenyl)piperazine-1-carbonyl)-5-methyl-4-oxothieno[2,3-d]pyrimidin-3 (4H)-yl)-N,N-diethylacetamide (Compound 6)

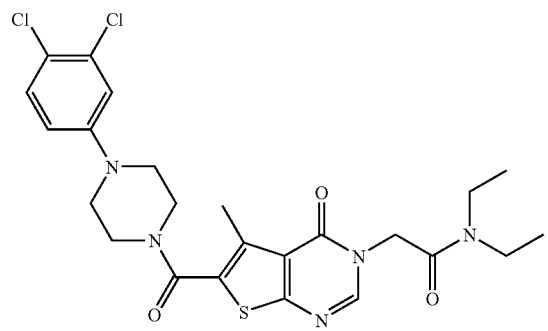

A. Synthesis of methyl 3-(2-(diethylamino)-2-oxoethyl)-5-methyl-4-oxo-3,4-dihydrothieno[2,3-d]pyrimidine-6-carboxylate

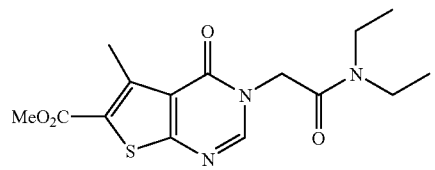

To a suspension of methyl 5-methyl-4-oxo-3,4-dihydrothieno[2,3-d]pyrimidine-6-carboxylate (2.24 g, 10 mmol) in $CH_3CN$ (20 mL) was added $K_2CO_3$ (1.38 g, 10 mmol), KI (1.61 g, 10 mmol), and 2-chloro-N,N-diethylacetamide (1.4 mL, 10 mmol). The reaction mixture was refluxed overnight and quenched with $H_2O$ (50 mL). The resulting precipitate was filtered and dried to afford 3.3 g of methyl 3-(2-(diethylamino)-2-oxoethyl)-5-methyl-4-oxo-3,4-dihydrothieno[2,3-d]pyrimidine-6-carboxylate as a solid (yield: quantitative).

B. Synthesis of 3-(2-(diethylamino)-2-oxoethyl)-5-methyl-4-oxo-3,4-dihydrothieno[2,3-d]pyrimidine-6-carboxylic acid

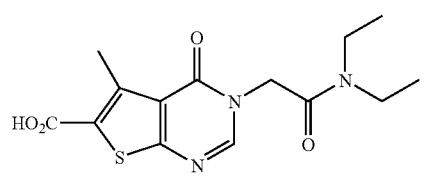

To a solution of methyl 3-(2-(diethylamino)-2-oxoethyl)-5-methyl-4-oxo-3,4-dihydrothieno[2,3-d]pyrimidine-6-carboxylate (3.3 g, 10 mmol) in THF (30 mL), MeOH (10 mL), and H₂O (10 mL) was added lithium hydroxide monohydrate (1.26 g, 30 mmol). The reaction mixture was then stirred at RT overnight. The reaction mixture was concentrated, diluted with H₂O (30 mL) and washed with DCM (2×30 mL). The aqueous layer was acidified (pH~2) with 1M HCl and the resultant precipitate was filtered and dried to give 1.6 g of 3-(2-(diethylamino)-2-oxoethyl)-5-methyl-4-oxo-3,4-dihydrothieno[2,3-d]pyrimidine-6-carboxylic acid, (yield: 50%).

C. Synthesis of 2-(6-(4-(3,4-dichlorophenyl)piperazine-1-carbonyl)-5-methyl-4-oxothieno[2,3-d]pyrimidin-3(4H)-yl)-N,N-diethylacetamide

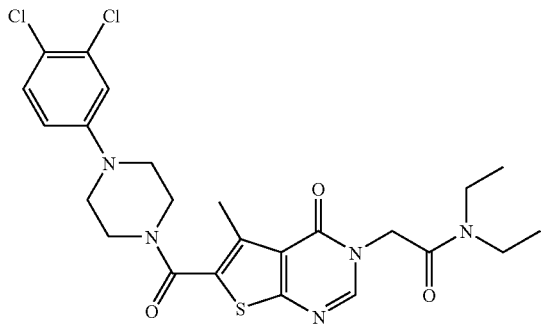

To a mixture of 3-(2-(diethylamino)-2-oxoethyl)-5-methyl-4-oxo-3,4-dihydrothieno[2,3-d]pyrimidine-6-carboxylic acid (0.12 g, 0.37 mmol) in DCM (5 mL) was added DIEA (0.2 mL, 1.1 mmol), 4(3,4-dichlorophenyl)piperazine (0.073 g, 0.37 mmol), and HATU (0.182 g, 0.48 mmol). The reaction mixture was stirred at RT overnight. The organic layer was diluted with CH₂Cl₂ and then washed with sat. NaHCO₃ aq. (20 mL), dried over Na₂SO₄, and concentrated to give crude product as a gummy solid. Purification by flash column chromatography using a mixture of Et₂O: DCM (1:1) as the eluant afforded the 0.092 g of 2-(6-(4-(3,4-dichlorophenyl)piperazine-1-carbonyl)-5-methyl-4-oxo thieno[2,3-d]pyrimidin-3(4H)-yl)-N,N-diethylacetamide, (yield: 50%).

Example 2

Synthesis of N-tert-butyl-2-(6-(4-(4-chlorophenyl)piperazine-1-carbonyl)-5-methyl-4-oxo thieno[2,3-d]pyrimidin-3(4H)-yl)acetamide (Compound 15)

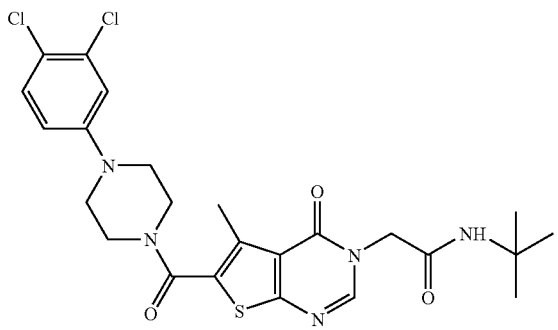

A. Synthesis of N-tert-butyl-2-chloroacetamide

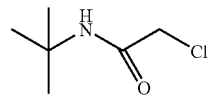

To a cooled (0° C.) solution of tert-butyl amine (5.25 mL, 50 mmol) in DCM (40 mL) was added triethylamine (14 mL, 101 mmol) followed by chloro acetylchloride (3.98 mL, 50.3 mmol). The reaction was warmed to RT and stirred for 2 h. The reaction mixture was concentrated, redissolved in EtOAc (20 mL) and washed with brine. The organic layer was dried over anhydrous Na₂SO4 and concentrated to yield 5.39 g of crude product which was further purified by flash column chromatography using 7:3 Pet. Ether: EtOAc as the eluant. Pure N-tert-butyl-2-chloroacetamide (3.65 g) was isolated.

B. Synthesis of methyl 3-(2-(tert-butylamino)-2-oxoethyl)-5-methyl-4-oxo-3,4-dihydrothieno[2,3-d]pyrimidine-6-carboxylate

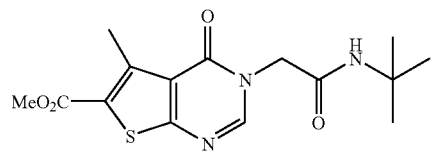

To a suspension of methyl 5-methyl-4-oxo-3,4-dihydrothieno[2,3-d]pyrimidine-6-carboxylate (2.69 g, 12 mmol) in CH₃CN (30 mL) was added K₂CO₃ (2.01 g, 14.5 mmol), KI (2.0 g, 12 mmol), and N-tert-butyl-2-chloroacetamide (1.8 g, 12 mmol). The reaction mixture was refluxed overnight and quenched with H₂O (150 mL). The resulting precipitate was filtered and dried to afford methyl 3-(2-(tert-butylamino)-2-oxoethyl)-5-methyl-4-oxo-3,4-dihydrothieno[2,3-d]pyrimidine-6-carboxylate, as a solid (yield: quantitative).

C. Synthesis of 3-(2-(tert-butylamino)-2-oxoethyl)-5-methyl-4-oxo-3,4-dihydrothieno[2,3-d]pyrimidine-6-carboxylic acid

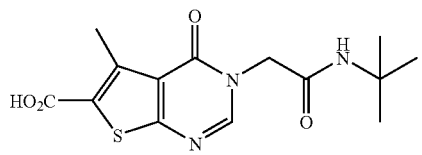

To a solution of methyl 3-(2-(tert-butylamino)-2-oxoethyl)-5-methyl-4-oxo-3,4-dihydrothieno[2,3-d]pyrimidine-6-carboxylate, (3.3 g, 10 mmol) in THF (30 mL), MeOH (10 mL), and H₂O (10 mL) was added lithium hydroxide monohydrate (1.26 g, 30 mmol). The reaction mixture was stirred at RT overnight. The reaction mixture was concentrated, diluted with H₂O (30 mL) and washed with DCM (2×30 mL). The aqueous layer was acidified (pH~2) with 1M HCl and the resultant precipitate was filtered and dried to give 1.8 g of 3-(2-(tert-butylamino)-2-oxoethyl)-5-methyl-4-oxo-3,4-dihydrothieno[2,3-d]pyrimidine-6-carboxylic acid (yield: 55%).

D. Synthesis of N-tert-butyl-2-(6-(4-(4-chlorophenyl)piperazine-1-carbonyl)-5-methyl-4-oxothieno[2,3-d]pyrimidin-3(4H)-yl)acetamide

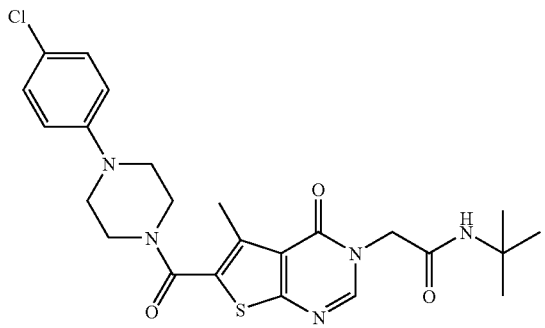

To a solution of 3-(2-(tert-butylamino)-2-oxoethyl)-5-methyl-4-oxo-3,4-dihydrothieno[2,3-d]pyrimidine-6-carboxylic acid, (0.13 g, 0.4 mmol) in DCM (5 mL) was added DIEA (0.2 mL, 1.1 mmol), 1-[4(chlorophenyl)]piperazine (0.107 g, 0.4 mmol), and HATU (0.197 g, 0.52 mmol). The reaction mixture was stirred at RT overnight. The organic layer was washed with sat. NaHCO₃ aq. (20 mL), dried over Na₂SO₄, and concentrated to give crude product as a gummy solid. Purification by flash column chromatography using a mixture of Et₂O:DCM (1:1) as the eluant afforded the 0.065 g of N-tert-butyl-2-(6-(4-(4-chlorophenyl)piperazine-1-carbonyl)-5-methyl-4-oxothieno[2,3-d]pyrimidin-3(4H)-yl)acetamide, (yield: 40%).

Example 3

Synthesis of 2-(6-(4-(3-chlorophenyl)piperazine-1-carbonyl)-5-methyl-4-oxothieno[2,3-d]pyrimidin-3(4H)-yl)-N-cyclohexylacetamide (Compound 24)

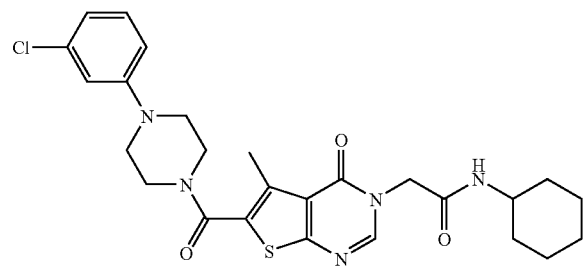

A. Synthesis of 2-chloro-N-cyclohexylacetamide

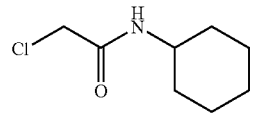

To a cooled (0° C.) solution of cyclohexylamine (2.31 mL, 20 mmol) in DCM (20 mL) was added triethylamine (5.7 mL, 40 mmol) followed by chloro acetylchloride (1.61 mL, 20 mmol). The reaction was warmed to RT and stirred for 3 h. The reaction mixture was concentrated, redissolved in EtOAc (20 mL) and washed with brine. The organic layer was dried over anhydrous Na₂SO₄ and concentrated to yield crude product which was further purified by flash column chromatography using 7:3 Pet. Ether:EtOAc as the eluant. 1.8 g of pure 2-chloro-N-cyclohexylacetamide was isolated.

B. Synthesis of methyl 3-(2-(cyclohexylamino)-2-oxoethyl)-5-methyl-4-oxo-3,4-dihydrothieno[2,3-d]pyrimidine-6-carboxylate

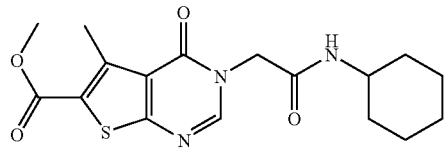

To a suspension of methyl 5-methyl-4-oxo-3,4-dihydrothieno[2,3-d]pyrimidine-6-carboxylate (2.24 g, 10 mmol) in CH₃CN (25 mL) was added K₂CO₃ (1.38 g, 10 mmol), KI (1.61 g, 10 mmol), and 2-chloro-N-cyclohexylacetamide (1.75 g, 10 mmol). The reaction mixture was refluxed overnight and quenched with H₂O (120 mL). The resulting precipitate was filtered and dried to afford methyl 3-(2-(cyclohexylamino)-2-oxoethyl)-5-methyl-4-oxo-3,4-dihydrothieno[2,3-d]pyrimidine-6-carboxylate, as a solid (yield: quantitative).

C. Synthesis of 3-(2-(cyclohexylamino)-2-oxoethyl)-5-methyl-4-oxo-3,4-dihydrothieno[2,3-d]pyrimidine-6-carboxylic acid

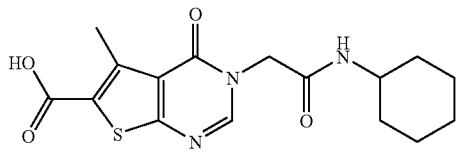

To a solution of methyl 3-(2-(cyclohexylamino)-2-oxoethyl)-5-methyl-4-oxo-3,4-dihydrothieno[2,3-d]pyrimidine-6-carboxylate (3.6 g, 10 mmol) in THF (30 mL), MeOH (10 mL), and H₂O (10 mL) was added lithium hydroxide monohydrate (1.26 g, 30 mmol). The reaction mixture was then stirred at RT overnight. The reaction mixture was concentrated, diluted with H₂O (30 mL) and washed with DCM (2×30 mL). The aqueous layer was acidified (pH~2) with 1M HCl and the resultant precipitate was filtered and dried to give 1.7 g of 3-(2-(cyclohexylamino)-2-oxoethyl)-5-methyl-4-oxo-3,4-dihydrothieno[2,3-d]pyrimidine-6-carboxylic acid, (yield: 52%).

D. Synthesis of 2-(6-(4-(3-chlorophenyl)piperazine-1-carbonyl)-5-methyl-4-oxothieno[2,3-d]pyrimidin-3(4H)-yl)-N-cyclohexylacetamide

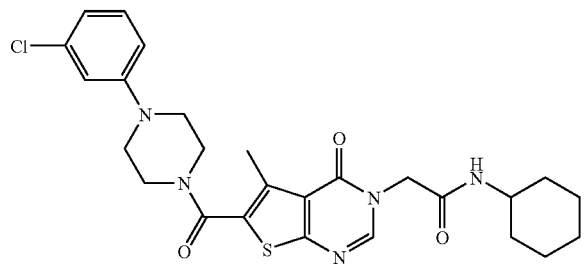

To a solution of 3-(2-(cyclohexylamino)-2-oxoethyl)-5-methyl-4-oxo-3,4-dihydrothieno[2,3-d]pyrimidine-6-carboxylic acid, (0.15 g, 0.45 mmol) in DCM (5 mL) was added DIEA (0.3 mL, 1.3 mmol), 1-3(chlorophenyl)piperazine (0.120 g, 0.45 mmol), and HATU (0.220 g, 0.58 mmol). The reaction mixture was stirred at RT overnight. The organic layer was washed with sat. NaHCO$_3$ aq. (20 mL), dried over Na$_2$SO$_4$, and concentrated to give crude product as a gummy solid. Purification by flash column chromatography using a mixture of Et$_2$O:DCM (1:1) as the eluant afforded the 0.082 g of 2-(6-(4-(3-chlorophenyl)piperazine-1-carbonyl)-5-methyl-4-oxothieno[2,3-d]pyrimidin-3(4H)-yl)-N-cyclohexylacetamide, (yield: 33%).

Example 4

Synthesis of N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide (Compound 64)

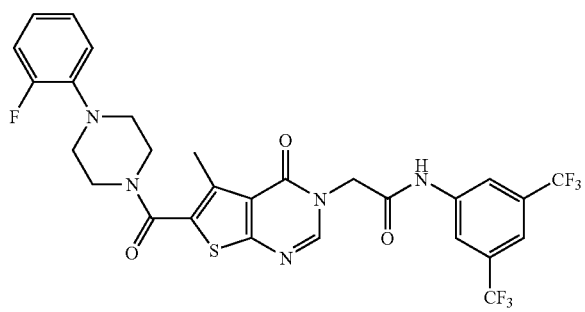

A. Synthesis of N-(3,5-bis(trifluoromethyl)phenyl)-2-chloroacetamide

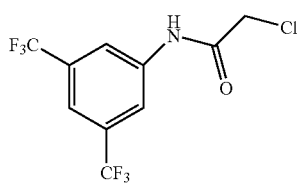

To a solution of 3,5-bis(trifluoromethyl)aniline (3.74 g, 16.3 mmol) in DCM (60 mL) was added chloroacetic acid (2.31 g, 24.4 mmol), EDC (5.0 g, 32.6 mmol) and DMAP (cat.). The reaction mixture was stirred at RT overnight. The contents were transferred to a separatory funnel and DCM layer was washed with saturated NaHCO$_3$ solution, dried over anhydrous Na$_2$SO$_4$. The crude product was purified by flash column chromatography using 3:1 Pet. Ether:DCM in. Purified product was isolated as a white solid weighing 3.67 g (yield: 74%).

B. Synthesis of methyl 3-(2-(3,5-bis(trifluoromethyl)phenylamino)-2-oxoethyl)-5-methyl-4-oxo-3,4-dihydrothieno[2,3-d]pyrimidine-6-carboxylate

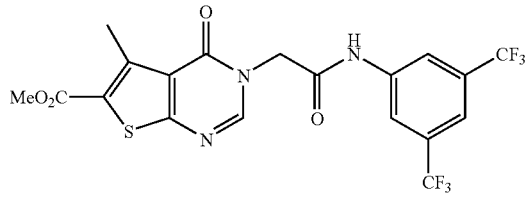

To a suspension of methyl 5-methyl-4-oxo-3,4-dihydrothieno[2,3-d]pyrimidine-6-carboxylate (1.62 g, 7.2 mmol) in CH$_3$CN (35 mL) was added K$_2$CO$_3$ (1.0 g, 7.24 mmol), KI (1.2 g, 7.23 mmol), and N-(3,5-bis(trifluoromethyl)phenyl)-2-chloroacetamide 1 (2.2 g, 7.19 mmol). The reaction mixture was refluxed overnight and quenched with H$_2$O (100 mL). The resultant precipitate was filtered and dried to afford 3.33 g of methyl 3-(2-(3,5-bis(trifluoromethyl)phenylamino)-2-oxoethyl)-5-methyl-4-oxo-3,4-dihydrothieno[2,3-d]pyrimidine-6-carboxylate, as a solid (yield: 90%).

C. Synthesis of 3-(2-(3,5-bis(trifluoromethyl)phenylamino)-2-oxoethyl)-5-methyl-4-oxo-3,4-dihydrothieno[2,3-d]pyrimidine-6-carboxylic acid

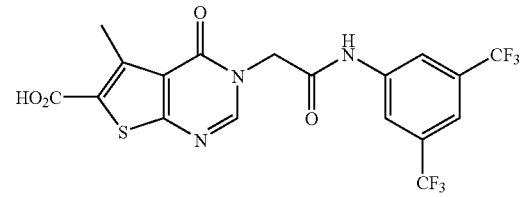

To a solution of methyl 3-(2-(3,5-bis(trifluoromethyl)phenylamino)-2-oxoethyl)-5-methyl-4-oxo-3,4-dihydrothieno[2,3-d]pyrimidine-6-carboxylate, (3.3 g, 6.75 mmol) in THF (30 mL), MeOH (10 mL), and H$_2$O (10 mL) was added lithium hydroxide monohydrate (1.42 g, 33.8 mmol). The reaction mixture was then stirred at RT overnight. The reaction mixture was concentrated, diluted with H$_2$O (30 mL) and washed with DCM (2×30 mL). The aqueous layer was acidified (pH~2) with 1M HCl and the resultant precipitate was filtered and dried to give 1.9 g of 3-(2-(3,5-bis(trifluoromethyl)phenylamino)-2-oxoethyl)-5-methyl-4-oxo-3,4-dihydrothieno[2,3-d]pyrimidine-6-carboxylic acid, (yield: 59%).

D. Synthesis of N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide

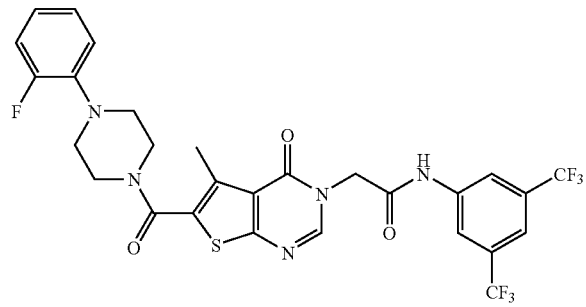

To a solution of 3-(2-(3,5-bis(trifluoromethyl)phenylamino)-2-oxoethyl)-5-methyl-4-oxo-3,4-dihydrothieno[2,3-d]pyrimidine-6-carboxylic acid (0.24 g, 0.5 mmol) in DCM (5 mL) was added DIEA (0.3 mL, 1.5 mmol), 2-fluorophenylpiperazine (0.060 mL, 0.5 mmol), and HATU (0.25 g, 0.65 mmol). The reaction mixture was stirred at RT overnight. The organic layer was washed with sat. NaHCO₃ aq. (20 mL), dried over Na₂SO₄, and concentrated to give crude product as a gummy solid. Purification by flash column chromatography using a mixture of Et₂O:DCM (1:1) as the eluant afforded the 0.19 g of the desired product N-(3,5-bis(trifluoromethyl)phenyl)-2-(6-(4-(2-fluorophenyl)piperazine-1-carbonyl)-5-methyl-4-oxo thieno[2,3-d]pyrimidin-3(4H)-yl)acetamide, (yield: 60%).

Example 5

Synthesis of 3-(2-(4,4-difluoropiperidin-1-yl)-2-oxoethyl)-5-methyl-6-(4-phenylpiperazine-1-carbonyl)thieno[2,3-d]pyrimidin-4(3H)-one (Compound 30)

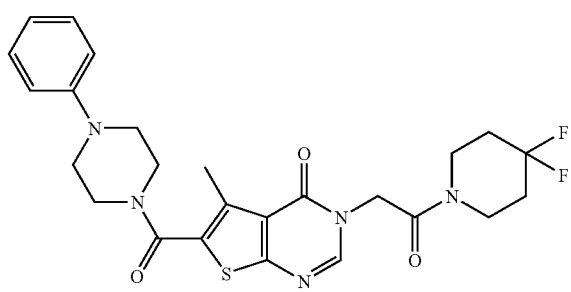

A. Synthesis of 5-methyl-4-oxo-3,4-dihydrothieno[2,3-d]pyrimidine-6-carboxylic acid

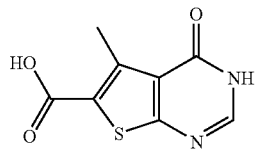

To a solution of ethyl 5-methyl-4-oxo-3,4-dihydrothieno[2,3-d]pyrimidine-6-carboxylate (1.0 g, 4.5 mmol) in THF (14 mL), MeOH (3 mL), and H₂O (3 mL) was added lithium hydroxide monohydrate (0.68 g, 16 mmol). The reaction mixture was stirred at RT overnight. The reaction mixture was concentrated, diluted with H₂O (20 mL) and washed with DCM (25 mL). The aqueous layer was acidified (pH~2) with 1M HCl and the resultant precipitate was filtered and dried to give 0.9 g of pure 5-methyl-4-oxo-3,4-dihydrothieno[2,3-d]pyrimidine-6-carboxylic acid, (yield: 94%).

B. Synthesis of 5-methyl-6-(4-phenylpiperazine-1-carbonyl)thieno[2,3-d]pyrimidin-4(3H)-one

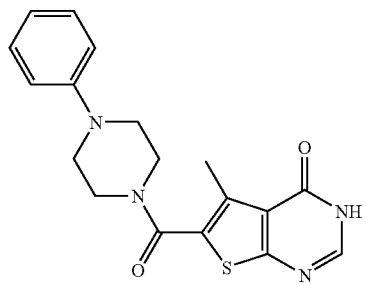

To a solution of 5-methyl-4-oxo-3,4-dihydrothieno[2,3-d]pyrimidine-6-carboxylic acid, (0.42 g, 2 mmol) in 1:1 DCM and DMF (10 mL) was added EDC (0.764 g, 4 mmol), DMAP (cat.) and 4-phenylpiperazine (0.324 g, 2 mmol). The reaction was stirred at RT overnight and DCM was removed. The resultant residue was partitioned between EtOAc (50 mL) and H₂O (50 mL). The organic layer was dried over Na₂SO₄ and concentrated to provide 0.4 g 5-methyl-6-(4-phenylpiperazine-1-carbonyl)thieno[2,3-d]pyrimidin-4(3H)-one, (yield: 57%).

C. Synthesis of 2-(4,4-difluoropiperidin-1-yl)acetyl chloride

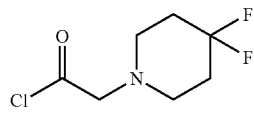

To a solution of 4,4-difluoropiperidine hydrochloride (1.44 g, 9 mmol) in DCM (15 mL) was added chloroacetic acid (0.94 g, 10 mmol), TEA (1.5 mL), EDC (3.82 g, 20 mmol) and DMAP (cat.). The reaction mixture was stirred at RT overnight. The contents were transferred to a separatory funnel and DCM layer was washed saturated NaHCO$_3$ solution, dried over anhydrous Na$_2$SO$_4$. The crude product was purified by flash column chromatography using 3:1 Pet. Ether: DCM in. 2-(4,4-difluoropiperidin-1-yl)acetyl chloride was isolated as a white solid weighing 1.57 g (yield: 88%).

D. Synthesis of 3-(2-(4,4-difluoropiperidin-1-yl)-2-oxoethyl)-5-methyl-6-(4-phenyl piperazine-1-carbonyl)thieno[2,3-d]pyrimidin-4(3H)-one

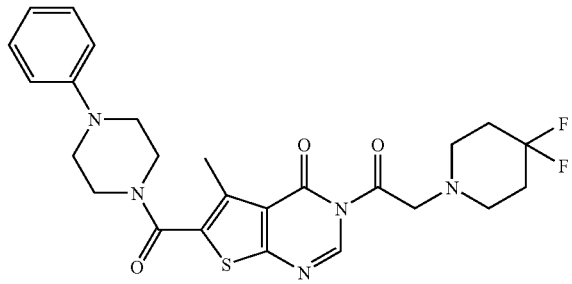

To a suspension of 5-methyl-6-(4-phenylpiperazine-1-carbonyl)thieno[2,3-d]pyrimidin-4(3H)-one, (0.4 g, 1.13 mmol) in CH$_3$CN (5 mL) was added K$_2$CO$_3$ (0.156 g, mmol), KI (0.182 g, 1.13 mmol), and 2-(4,4-difluoropiperidin-1-yl) acetyl chloride (0.223 g, 1.13 mmol). The reaction mixture was refluxed overnight and then quenched with H$_2$O (20 mL). The resultant precipitate was filtered and dried to provide a crude solid which was purified by flash chromatography (Et$_2$O:DCM, 1:1) providing 0.29 g of pure 3-(2-(4,4-difluoropiperidin-1-yl)-2-oxoethyl)-5-methyl-6-(4-phenyl piperazine-1 carbonyl)thieno[2,3-d]pyrimidin-4(3H)-one, (yield: 50%).

Example 6

Synthesis of N-(2,4-difluorophenyl)-2-(6-(4-(2-fluorophenyl)piperazine-1-carbonyl)-5-methyl-4-oxothieno[2,3-d]pyrimidin-3(4H)-yl)acetamide
(Compound 139)

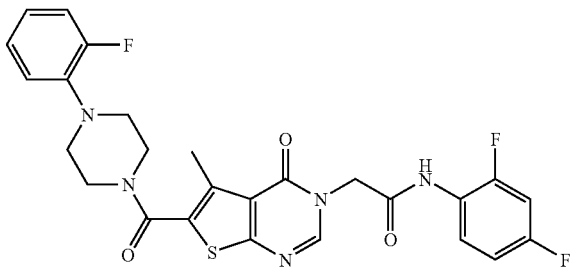

A. Synthesis of 6-(4-(2-fluorophenyl)piperazine-1-carbonyl)-5-methylthieno[2,3-d]pyrimidin-4(3H)-one

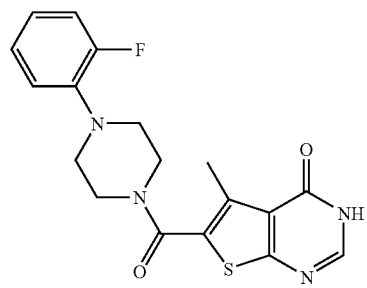

To a solution of 5-methyl-4-oxo-3,4-dihydrothieno[2,3-d]pyrimidine-6-carboxylic acid, (2 g, 9.5 mmol) in DMF (20 mL) was added DIEA (5 mL, 28.5 mmol), 1-(2-fluorophenyl)piperazine (1.7 g, 9.5 mmol), and HATU (4.7 g, 12.3 mmol). The reaction mixture was stirred at RT overnight. The reaction mixture was diluted with EtOAc (60 mL) and the organic layer was washed successively with sat. NaHCO$_3$ aq. (50 mL) and brine (50 mL). The organic layer was separated, dried over Na$_2$SO$_4$, and concentrated to give crude product as a gummy solid. Purification by flash column chromatography using EtOAc as the eluant afforded the 3.0 g of pure 6-(4-(2-fluorophenyl)piperazine-1-carbonyl)-5-methylthieno[2,3-d]pyrimidin-4(3H)-one, (yield: 86%).

B. Synthesis of 2-chloro-N-(2,4-difluorophenyl)acetamide

To a cooled (0° C.) solution of 2,4-difluoroaniline, (1.5 g, 11.6 mmol) in DCM (50 mL) was added triethylamine (1.9 mL, 13.9 mmol) followed by 2-chloroacetyl chloride (1.0 mL, 12.8 mmol). The reaction was warmed to RT and stirred for 2 h. The reaction mixture was concentrated, redissolved in EtOAc (50 mL) and washed with brine (50 mL). The organic layer was dried over anhydrous Na$_2$SO$_4$ and concentrated to yield 2.2 g of crude product which was further purified by flash column chromatography using 1:1 EtOAc:hexanes as the eluent. 2.0 g of 2-chloro-N-(2,4-difluorophenyl)acetamide, (yield: 84%) was isolated.

C. Synthesis of N-(2,4-difluorophenyl)-2-(6-(4-(2-fluorophenyl)piperazine-1-carbonyl)-5-methyl-4-oxothieno [2,3-d]pyrimidin-3(4H)-yl)acetamide

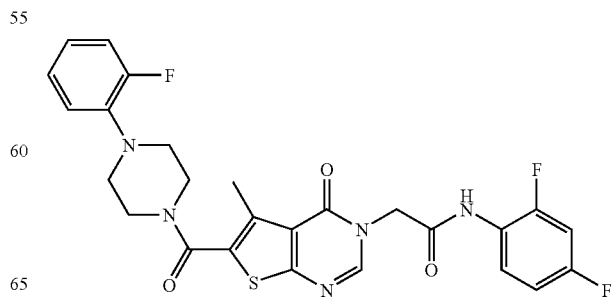

To a suspension of 6-(4-(2-fluorophenyl)piperazine-1-carbonyl)-5-methylthieno[2,3-d]pyrimidin-4(3H)-one, (0.06 g, 0.16 mmol) in CH$_3$CN (0.5 mL) was added K$_2$CO$_3$ (22 mg, 0.16 mmol), KI (29 mg, 0.17 mmol), and 2-chloro-N-(2,4-difluorophenyl)acetamide, (36 mg, 0.16 mmol). The reaction mixture was heated at 130° C. for 25 min in a microwave reactor. The reaction was quenched with H$_2$O (25 mL) and the aqueous layer was extracted with EtOAc (25 mL). The organic layer was washed with brine (25 mL), dried over Na$_2$SO$_4$ and concentrated. The crude material was purified by flash chromatography (Et$_2$O:DCM, 1:1) providing 30 mg of pure N-(2,4-difluorophenyl)-2-(6-(4-(2-fluorophenyl)piperazine-1-carbonyl)-5-methyl-4-oxothieno[2,3-d]pyrimidin-3(4H)-yl)acetamide, (yield: 35%).

Example 7

Synthesis of 3-(2-(4-(3-chlorophenyl)piperazin-1-yl)-2-oxoethyl)-5-methyl-6-(pyrrolidine-1-carbonyl)thieno[2,3-d]pyrimidin-4(3H)-one (Compound 119)

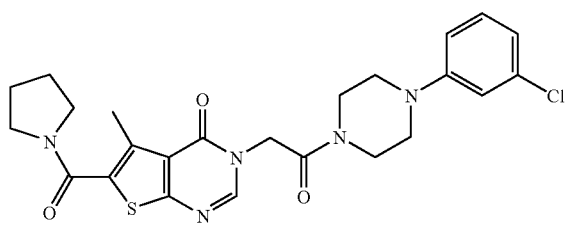

A. Synthesis of -methyl-6-(pyrrolidine-1-carbonyl)thieno[2,3-d]pyrimidin-4(3H)-one

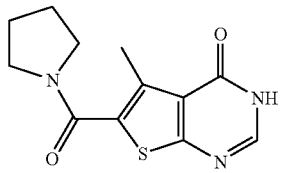

To a cooled (0° C.) solution of pure 5-methyl-4-oxo-3,4-dihydrothieno[2,3-d]pyrimidine-6-carboxylic acid, (0.1 g, 0.47 mmol) in DMF (5 mL) was added dropwise thionyl chloride (0.034 mL, 0.47 mmol). The reaction mixture was stirred at 0° C. for 15 min. Pyrrolidine (0.12 mL, 1.4 mmol) was then added and the reaction was allowed to warm to RT over 1 h. The reaction mixture was quenched with saturated NaHCO$_3$ (25 mL) and extracted with EtOAc (25 mL). The organic layer was washed with brine (30 mL), dried over Na$_2$SO$_4$ and concentrated to give 0.080 g of pure 5-methyl-6-(pyrrolidine-1-carbonyl)thieno[2,3-d]pyrimidin-4(3H)-one, (yield: 65%).

B. Synthesis of 2-chloro-1-(4-(3-chlorophenyl)piperazin-1-yl)ethanone

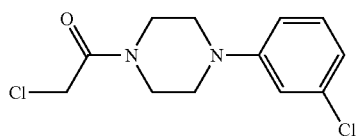

To solution of 1-(3-chlorophenyl)piperazine hydrochloride (1.2 g, 5.2 mmol) in DCM (10 mL) was added triethylamine (1.0 mL, 7.3 mmol), EDC (1.9 g, 10 mmol), DMAP (cat.) and chloroacetic acid (0.4 g, 5.2 mmol). The reaction was stirred at RT overnight and DCM was removed. The resultant residue was partitioned between EtOAc (50 mL) and H$_2$O (50 mL). The organic layer was dried over Na$_2$SO$_4$ and concentrated to provide 1.0 g of pure 2-chloro-1-(4-(3-chlorophenyl)piperazin-1-yl)ethanone, (yield: 70%).

C. Synthesis of 3-(2-(4-(3-chlorophenyl)piperazin-1-yl)-2-oxoethyl)-5-methyl-6-(pyrrolidine-1-carbonyl)thieno[2,3-d]pyrimidin-4(3H)-one

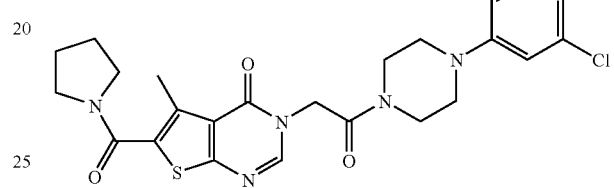

To a suspension of 5-methyl-6-(pyrrolidine-1-carbonyl)thieno[2,3-d]pyrimidin-4(3H)-one, (0.06 g, 0.23 mmol) in CH$_3$CN (5 mL) was added K$_2$CO$_3$ (0.032 g, 0.23 mm (38 mg, 0.23 mmol), and 2-chloro-1-(4-(3-chlorophenyl)piperazin-1-yl)ethanone, (0.062 g, 0.23 mmol). The reaction mixture was refluxed overnight and then quenched with H$_2$O (20 mL). The resultant precipitate was filtered and dried to provide a crude solid which was purified by flash chromatography (Et$_2$O:DCM, 1:1) providing 0.025 g of pure 3-(2-(4-(3-chlorophenyl)piperazin-1-yl)-2-oxoethyl)-5-methyl-6-(pyrrolidine-1-carbonyl)thieno[2,3-d]pyrimidin-4(3H)-one, (yield: 22%).

Example 8

Synthesis of 2-(6-(4-(3-chlorophenyl)piperazine-1-carbonyl)-5-methyl-4-oxothieno[2,3-d]pyrimidin-3(4H)-yl)-N-ethyl-N-(2,2,2-trifluoroethyl)acetamide (Compound 126)

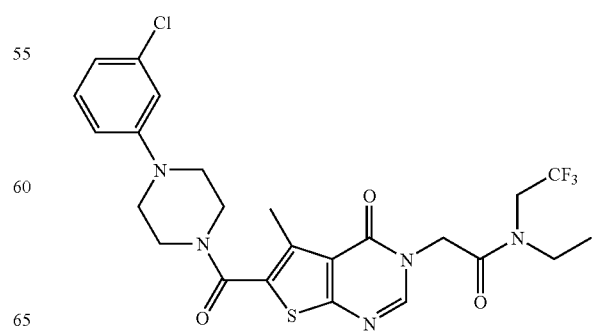

A. Synthesis of 6-(4-(3-chlorophenyl)piperazine-1-carbonyl)-5-methylthieno[2,3-d]pyrimidin-4(3H)-one

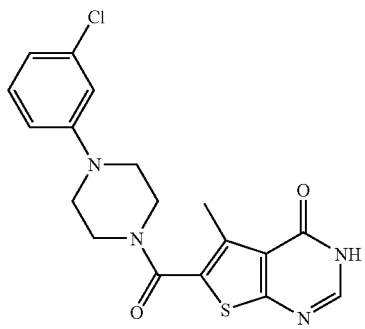

To a solution of 5-methyl-4-oxo-3,4-dihydrothieno[2,3-d]pyrimidine-6-carboxylic acid, (2 g, 9.5 mmol) in DMF (20 mL) was added DIEA (5 mL, 28.5 mmol), 1-(3-chlorophenyl)piperazine hydrochloride (2.2 g, 9.5 mmol), and HATU (4.7 g, 12.3 mmol). The reaction mixture was stirred at RT overnight. The reaction mixture was diluted with EtOAc (60 mL) and the organic layer was washed successively with sat. NaHCO$_3$ aq. (50 mL) and brine (50 mL). The organic layer was separated, dried over Na$_2$SO$_4$, and concentrated to give crude product as a gummy solid. Purification by flash column chromatography using EtOAc as the eluent afforded the 3 g of pure 6-(4-(3-chlorophenyl)piperazine-1-carbonyl)-5-methylthieno[2,3-d]pyrimidin-4(3H)-one, (yield: 81%).

B. Synthesis of N-ethyl-2,2,2-trifluoroethanamine hydrochloride

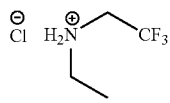

To a solution of 2,2,2-trifluoroethylamine hydrochloride (0.5 g, 3.7 mmol) in MeOH (5 mL) was added triethylamine (0.51 mL, 0.37 mmol) followed by acetaldehyde (1.0 mL, excess). The reaction mixture was then stirred at 0° C. for 3 h. Sodium borohydride (1 g, 5.9 mmol) was then added and the reaction mixture was stirred at 0° C. for 20 min. The reaction was quenched with 1M NaOH (10 mL) and the aqueous layer was extracted with DCM (25 mL). The organic layer was separated and to it was added 2M HCl in Et$_2$O (10 mL). The resultant precipitate was filtered to give 0.45 g of N-ethyl-2,2,2-trifluoroethanamine hydrochloride, (yield: 75%).

C. Synthesis of 2-chloro-N-ethyl-N-(2,2,2-trifluoroethyl)acetamide

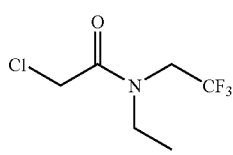

To a cooled (0° C.) solution of N-ethyl-2,2,2-trifluoroethanamine hydrochloride, (0.45 g, 2.8 mmol) in DCM (10 mL) was added triethylamine (1.6 mL, 11.2 mmol) followed by 2-chloroacetyl chloride (0.22 mL, 2.8 mmol). The reaction was warmed to RT and stirred for 2 h. The reaction mixture was concentrated, redissolved in EtOAc (20 mL) and washed with brine (25 mL). The organic layer was dried over anhydrous Na$_2$SO$_4$ and concentrated to yield 0.6 g of crude product which was further purified by flash column chromatography using 1:1 EtOAc:hexanes as the eluent. 0.5 g of 2-chloro-N-ethyl-N-(2,2,2-trifluoroethyl)acetamide, (yield: 88%) was isolated.

D. Synthesis of 2-(6-(4-(3-chlorophenyl)piperazine-1-carbonyl)-5-methyl-4-oxothieno[2,3-d]pyrimidin-3(4H)-yl)-N-ethyl-N-(2,2,2-trifluoroethyl)acetamide

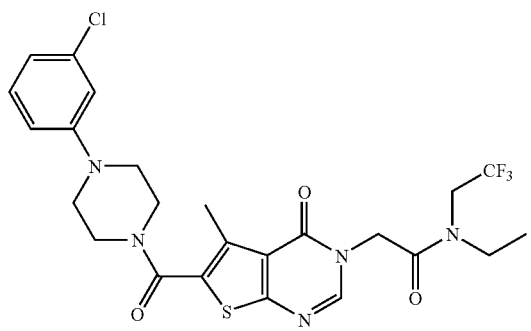

To a suspension of 6-(4-(3-chlorophenyl)piperazine-1-carbonyl)-5-methylthieno[2,3-d]pyrimidin-4(3H)-one, (0.1 g, 0.26 mmol) in CH$_3$CN (5 mL) was added K$_2$CO$_3$ (36 mg, 0.26 mmol), KI (43 mg, 0.26 mmol), and 2-chloro-N-ethyl-N-(2,2,2-trifluoroethyl)acetamide, (52 mg, 0.26 mmol). The reaction mixture was refluxed overnight and then quenched with H$_2$O (20 mL). The resultant precipitate was filtered and dried to provide a crude solid which was purified by flash chromatography (Et$_2$O:DCM, 1:1) providing 30 mg of pure 2-(6-(4-(3-chlorophenyl)piperazine-1-carbonyl)-5-methyl-4-oxothieno[2,3-d]pyrimidin-3 (4H)-yl)-N-ethyl-N-(2,2,2-trifluoroethyl)acetamide, (yield: 21%).

Example 9

Synthesis of Synthesis of 7-(4-(3-chlorophenyl)piperazine-1 Carbonyl)-3-(2-oxo-2-(-pyrrolidin-1-yl)ethyl)quinazolin-4(3H)-one (Compound 111)

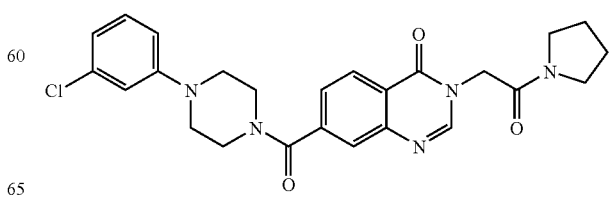

A. Synthesis of 2-Aminoterephthalic acid

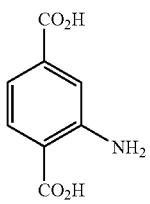

3-Amino-4-(methoxylcarbonyl)benzoic acid (2.5 g, 12.8 mmol) was dissolved in a mixture of THF-MeOH—H$_2$O (40 mL, 30:5:5) and then LiOH—H$_2$O (2 g, 64 mmol) was added. The mixture stirred at RT over night. The reaction mixture was concentrated and the residue was dissolved in 5 mL of water and then acidified with 6N HCl to pH~3. The solid was filtered and dried to give the desired product in 63% yield.

B. Synthesis of 4-Oxo-3,4-dihydroquinazoline-7-carboxylic acid

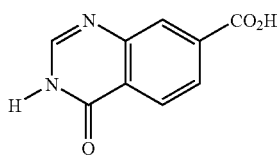

A mixture of 2-amino terephthalic acid (2 g, 11 mmol) and formamide (10 mL) was heated at 180° C. for 5 h. The reaction mixture was cooled to RT and acetone was added. The solid precipitated thus obtained was stirred for 2 h, filtered and dried to give 4-oxo-3,4-dihydroquinazoline-7-carboxylic acid in 80% yield.

C. Synthesis of Methyl 4-oxo-3,4-dihydroquinazoline-7-carboylate

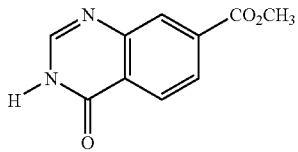

A mixture of 4-oxo-3,4-dihydroquinazoline-7-carboxylic acid (2.5 g, 13.15 mmol) in 80 mL of methanol was added thionyl chloride (2.5 mL) at 5° C. and then refluxed at 80° C. over night. The reaction mixture was concentrated under vacuum and the residue dissolved in ethyl acetate. The organic layer was washed with 10% aqueous NaHCO$_3$, water, brine and dried. The solvent was removed to give methyl 4-oxo-3,4-dihydroquinazoline7-carboxylate in 70% yield as solid.

D. Synthesis of methyl 4-oxo-3-(2-oxo-2-(pyrrolidin-1-yl)ethyl-3,4-dihydroquinazoline-7-carboxylate

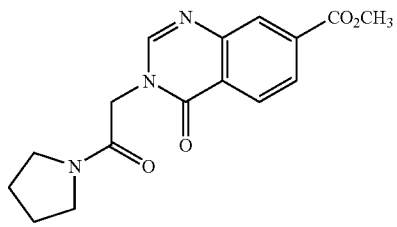

Methyl 4-oxo-3,4-dihydroquinazoline-7-caboxylate (50 mg, 0.23 mmol) dissolved in of acetonitrile (15 mL) and then K$_2$CO$_3$ (20 mg), KI (15 mg) was added followed by addition of 2-chloro-1-(pyrroldin-1-yl)ethanone (35 mg, 0.24 mmol). The mixture was refluxed over night. The reaction mixture was concentrated and the residue was purified by flash chromatography (Et$_2$O:DCM, 1:1) to give methyl 4-oxo-3-(2-oxo-2(pyrroldin-1-yl) ethyl-3,4-dihydroquinazoline-7-carboxlate in 70% yield.

E. Synthesis of 4-oxo-3-(2-oxo-2-(pyrrolidin-1-yl)ethyl-3,4-dihydroquinazoline-7-caboxylic acid

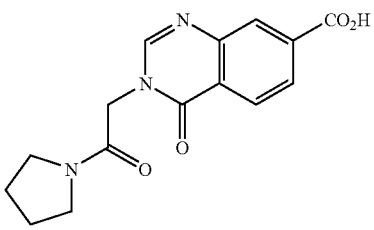

Methyl 4-oxo-3-(2-oxo-2-(pyrrolidin-1-yl)ethyl-3,4-dihydroquinazoline-7-carboxylate (100 mg, 0.32 mmol) was dissolved in a mixture of THF-MeOH—H$_2$O (12 mL, 10:1:1) followed by addition of LiOH—H$_2$O (53 mg). The mixture was stirred at RT over night. The solvent evaporated and the residue was dissolved in water (2 mL) and then acidified with 2N HCl to pH~3. The solid was filtered off and dried and gave 50 mg of acid in 60% yield.

F. Synthesis of 7-(4-(3-chlorophenyl)piperazine-1-carbonyl)-3-(2-oxo-2-(pyrrolidin-1-yl)ethyl)quinazolin-4(3H)-one

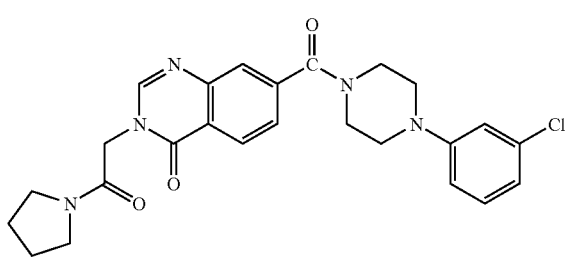

4-oxo-3-(2-oxo-2-(pyrrolidin-1-yl)ethyl-3,4-dihydro-quinazoline7-carboxylic acid (40 mg, 0.13 mmol) was dissolved in DCM (10 mL) followed by addition of DIEA (0.2 mL) HATU (100 mg) and 3-chlorophenyl piperazine (29 mg, 0.14 mmol). The mixture stirred at RT over night. The reaction mixture was concentrated and the residue was semi-purified by flash chromatography and then further purified by rotary prep TLC using DCM-Ether (1:1) to give 7-(4-(3-chlorophenyl)piperazine-1-carbonyl)-3-(2-oxo-2-(pyrrolidin-1-yl)ethyl)quinazolin-4(3H)-one in 40% yield with the HPLC purity of ≧95%.

Example 10

Synthesis of 6-(4-(3-chlorophenyl)piperazine-1-carbonyl)-3-(2-oxo-2-(pyrrolidin-1-yl)ethyl)quinazolin-4(3H)-one (Compound 115)

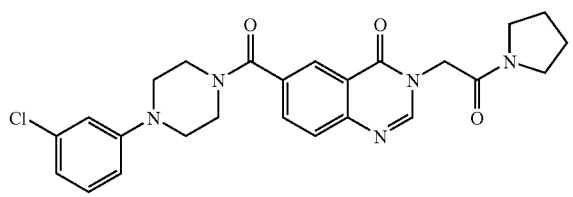

A. Synthesis of 4-Nitro isophthalic acid

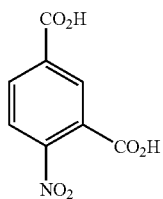

A mixture of 3-methyl-4-nitrobenzoic acid (6.3 g, 34.8 mmol), pyridine (100 mL) and water (100 mL) was heated to reflux. To the hot reaction mixture was added KMnO$_4$ (130 g) portion wise and refluxed for 72 h. The reaction mixture was filtered through celite and washed with hot water. The filtrate was concentrated under vacuum, residue diluted with water (50 mL) and acidified with concentrated HCl at 0° C. The solid obtained was filtered, washed with water and dried under vacuum to give 4-nitro isophthalic acid in 40% yield.

B. Synthesis of 4-Amino isophthalic acid

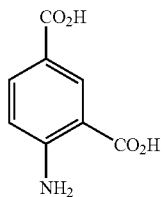

To a solution of 4-nitro isophthalic acid (4 g, 18.95 mmol) in MeOH (200 mL) was added Pd/C (20%) and the mixture was hydrogenated at RT over night. The reaction mixture was filtered through Celite and filtrate concentrated under vacuum to give 4-amino isophthalic acid in 60% as a solid.

C. Synthesis of 4-Oxo-3,4-dihydroquinazolin-6-carboxylic acid

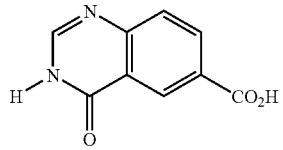

A mixture of 4-amino isophthalic acid (2 g, 11.04 mmol) and formamide (10 mL) was heated at 180° C. for 5 h. The reaction mixture was cooled to RT and acetone was added. The solid precipitate thus obtained was stirred for 2 h, filtered and dried to give 4-oxo-3,4-dihydroquinazoline-6-carboxylic acid in 50% yield.

D. Synthesis of Methyl 4-Oxo-3,4-dihydroquinazoline-6-carboxylate

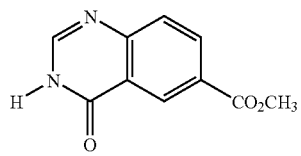

To a mixture of 4-oxo-3,4-dihydroquinazoline-6-carboxylic acid (2.5 g, 13.15 mmol) in methanol (80 mL) was added thionyl chloride (2.5 mL) at 5° C. The mixture was refluxed at 80° C. over night. The reaction mixture was concentrated under vacuum and crude taken in ethyl acetate. The organic layer was washed with 10% aqueous NaHCO$_3$, water, brine and dried. The solvent was removed to give methyl 4-oxo-3,4-dihydroquinazoline-6-carboxylate in 55% as solid.

E. Synthesis of methyl 4-oxo-3-(2-oxo-2-(pyrrolidin-1-yl) ethyl-3,4-dihydroquinazoline-6-carboxylate

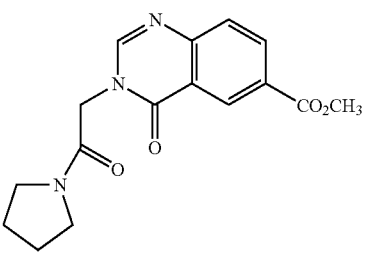

Methyl 4-oxo-3,4-dihydroquinazoline-6-caboxylate (50 mg), dissolved in acetonitrile (15 mL) and then K$_2$CO$_3$ (20 mg) KI (15 mg) was added followed by addition of 2-chloro-1-(pyrroldin-1-yl) ethanone (35 mg, 0.23 mmol). The mixture was refluxed over night. The resulting mixture was evaporated followed by purification using flash chromatography (Et₂O:DCM, 1:1) to give methyl 4-oxo-3-(2-oxo-2(pyrrolidin-1-yl))ethyl-3,4-dihydroquinazoline-6-carboxlate in 70% yield.

F. Synthesis of 4-oxo-3-(2-oxo-2-(pyrrolidin-1-yl)ethyl-3,4-dihydroquinazoline-6-caboxylic acid

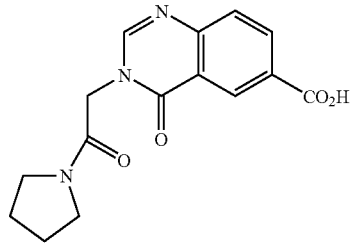

Methyl 4-oxo-3-(2-oxo-2-(pyrrolidin-1-yl)ethyl-3,4-dihydroquinazoline-6-carboxylate (100 mg, 0.31 mmol) was dissolved in a mixture of THF-MeOH—H₂O (12 mL, 10:1:1) followed by the addition of LiOH—H₂O (53 mg). The mixture was stirred at RT over night. The solvent evaporated and the residue was dissolved in 2 mL of water and then acidified with 2N HCl to pH~3. The solid was filtered off and dried and gave 50 mg of acid in 60% yield.

G. Synthesis of 6-(4-(3-chlorophenyl)piperazine-1-carbonyl)-3-(2-oxo-2-(pyrrolidin-1-yl)ethyl)quinazolin-4(3H)-one

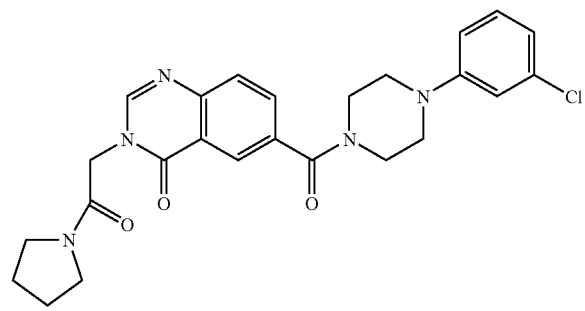

4-oxo-3-(2-oxo-2-(pyrrolidin-1-yl)ethyl-3,4-dihydroquinazoline-6-carboxylic acid (40 mg, 0.13 mmol) was dissolved in DCM (10 mL) followed by the addition of DIEA (0.2 mL), HATU (100 mg) and 3-chlorophenyl piperazine (29 mg, 0.14 mmol). The mixture stirred at RT over night. The residue was semi-purified by flash chromatography and then further purified by rotary prep TLC using DCM-Ether (1:1) to gave 6-(4-(3-chlorophenyl)piperazine-1-carbonyl)-3-(2-oxo-2-(pyrrolidin-1-yl)ethyl)quinazolin-4(3H)-one in 40% yield and HPLC purity of ≧95%.

Example 11

Synthesis of N-(4-chlorobenzyl)-3-(2-fluorobenzyl)-4-oxo-3,4-dihydroquinazoline-7-carboxamide (Compound 104)

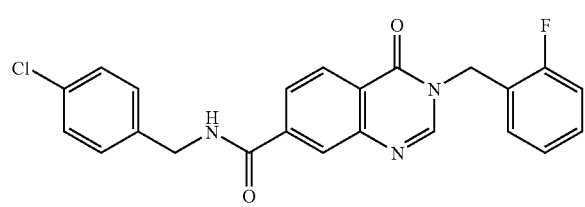

A. Synthesis of methyl 3-(-2-flourobenzyl)-4-oxo-3,4-dihydoquinazoline-7-carboxylate

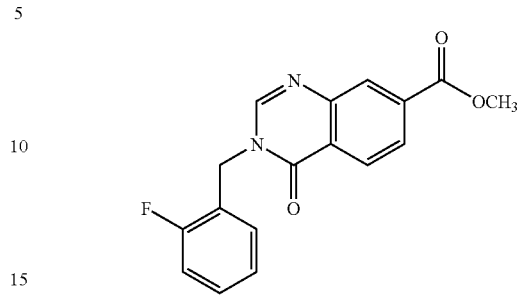

Methyl 4-oxo-3,4-dihydroquinazoline-7-carboxlate 300 mg (1.37 mmol) was dissolved in acetonitrile (20 mL) followed by addition of K₂CO₃ (100 mg), KI (80 mg) and 2-flourobenzyl chloride (0.2 mL, 1.65 mmol). The mixture was refluxed over night. The reaction mixture was concentrated and the residue was purified by flash chromatography (Et₂O:DCM, 1:1) to give methyl 3-(2-flourobenzyl)4-oxo-3,4-dihydroquinazoline-7-carboxylate in 70% yield.

B. Synthesis of 3-(2-fluorobenzyl)-4-oxo-3,4-dihydroquinazoline-7-carboxylic acid

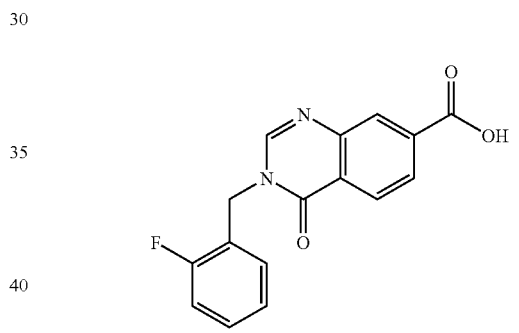

Methyl 3-(2-flourobenzyl)-4-oxo-3,4-dihydroquinazoline-7-carboylate 300 mg, 0.92 mmol) was dissolved In a mixture of THF-MeOH—H₂O (10 mL-3 mL-3 mL) followed by the addition of LiOH—H₂O (200 mg). The mixture was stirred at RT over night. The solvent evaporated and the residue was dissolved in 4 mL of water and then acidified with 2N HCl to pH~3. The solid was filtered off dried to gave 270 mg 3-(2-flourobenzyl)-4-oxo-3,4-dihydroquinazoline-7-carboxylic acid in 75% yield.

C. Synthesis of N-(3-chlorobenzyl)-3-(2-flourobenzyl)-4-oxo-3,4-dihydroquinazoline-7-carboxamide

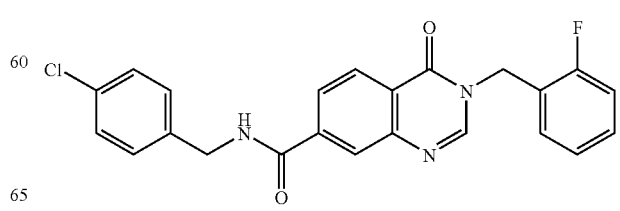

3-(2-flourobenzyl)-4-oxo-3,4-dihydroquinazoline-7-carboylate (65 mg, 0.218 mmol was dissolved in DCM (10 mL) followed by the addition of DIEA (0.1 mL), HATU (100 mg) and 4-chlorobenzylamine (34 mg, 0.239 mmol). The mixture was stirred at RT overnight. The residue was semi-purified by flash chromatography and then further purified by rotary prep TLC using DCM-Ether (1:1) to give the desired product in 65% yield with HPLC purity of ≧95%.

Example 12

Synthesis of 5-methyl-3-(2-(2-oxopyrrolidin-1-yl)ethyl)-6-(4-phenylpiperazine-1-carbonyl)thieno[2,3-d]pyrimidin-4(3H)-one (Compound 92)

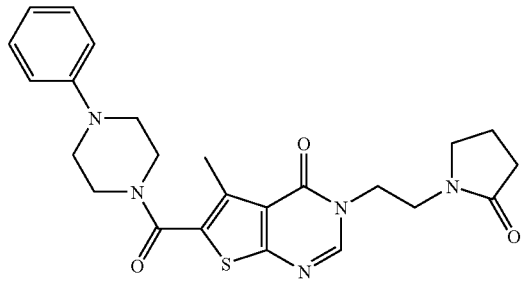

A. Synthesis of 2-(2-oxopyrrolidin-1-yl)ethyl methanesulfonate

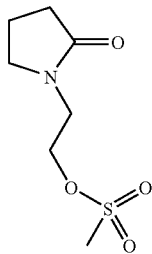

To a Stirred solution of 1-(2-hydroxyethyl)pyrrolidin-2-one (2.6 g, 20 mmol) in pyridine (15 ml) was added methanesulfonyl chloride (2.28 g, 20 mmol) and the reaction mixture was stirred at RT overnight. Solution was concentrated and diluted with ethyl acetate (50 ml) and washed with water (50 ml). Ethyl acetate layer was separated, dried over anhydrous sodium sulfate and evaporated to yield 3.0 g of 2-(2-oxopyrrolidin-1-yl)ethyl methanesulfonate, as an oil (yield: 75%).

B. Synthesis of methyl 5-methyl-4-oxo-3-(2-(2-oxopyrrolidin-1-yl)ethyl)-3,4-dihydrothieno[2,3-d]pyrimidine-6-carboxylate

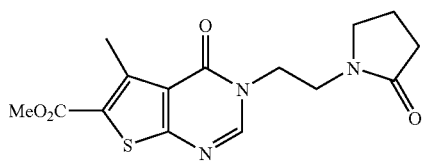

To a solution of methyl 5-methyl-4-oxo-3,4-dihydrothieno[2,3-d]pyrimidine-6-carboxylate (0.8 g, 3.5 mmol) in DMF (10 ml) was added NaH (0.28 g, 7 mmol) followed by the addition of 2-(2-oxopyrrolidin-1-yl)ethyl methanesulfonate (0.7 g, 3.5 mmol). The mixture was then stirred overnight at RT. Reaction was quenched with water (10 ml) and mixture extracted with ethyl acetate. Ethyl acetate layer was separated, dried over anhydrous sodium sulfate and evaporated to yield 0.5 g of methyl 5-methyl-4-oxo-3-(2-(2-oxopyrrolidin-1-yl)ethyl)-3,4-dihydrothieno[2,3-d]pyrimidine-6-carboxylate, as an oil (yield: 42.8%).

C. Synthesis of 5-methyl-4-oxo-3-(2-(2-oxopyrrolidin-1-yl)ethyl)-3,4-dihydrothieno[2,3-d]pyrimidine-6-carboxylic acid

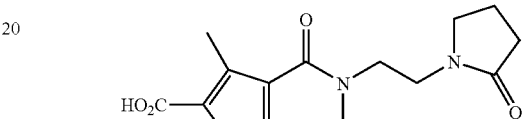

Methyl 5-methyl-4-oxo-3-(2-(2-oxopyrrolidin-1-yl)ethyl)-3,4-dihydrothieno[2,3-d]pyrimidine-6-carboxylate (0.5 g, 1.5 mmol) was dissolved in a mixture of THF-MeOH—H₂O (10 mL-3 mL-3 mL) followed by the addition of LiOH—H₂O (0.250 g). The mixture was stirred at RT over night. The solvent evaporated and the residue was dissolved in 4 mL of water and then acidified with 2N HCl to pH~3. The solid was filtered off, dried to gave 0.290 g of 5-methyl-4-oxo-3-(2-(2-oxopyrrolidin-1-yl)ethyl)-3,4-dihydrothieno[2,3-d]pyrimidine-6-carboxylic acid, in 60% yield.

D. Synthesis of 5-methyl-3-(2-(2-oxopyrrolidin-1-yl)ethyl)-6-(4-phenylpiperazine-1-carbonyl)thieno[2,3-d]pyrimidin-4(3H)-one

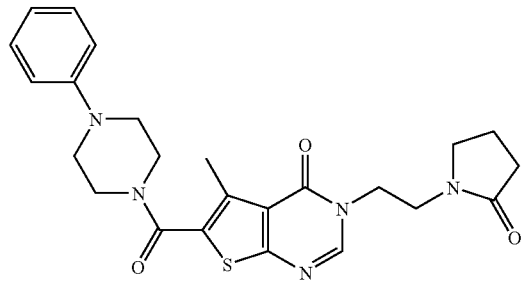

To a solution of 5-methyl-4-oxo-3-(2-(2-oxopyrrolidin-1-yl)ethyl)-3,4-dihydrothieno[2,3-d]pyrimidine-6-carboxylic acid, (0.128 g, 0.4 mmol) in DCM (5 mL) was added DIEA (0.37 mL, 1.2 mmol), 1-(4-phenyl)piperazine (0.061 ml, 0.4 mmol), and HATU (0.197 g, 0.52 mmol). The reaction mixture was stirred at RT overnight. The reaction mixture was diluted with DCM (20 mL) and the organic layer was washed with sat. NaHCO₃ aq. (20 mL) and brine (20 mL). The organic layer was separated, dried over Na₂SO₄, and concentrated to give crude product as a gummy solid. Purification by flash column chromatography using 2% Methanol in DCM as the eluent afforded the 0.093 g of pure 5-methyl-3-(2-(2-oxopyrrolidin-1-yl)ethyl)-6-(4-phenylpiperazine-1-carbonyl) thieno[2,3-d]pyrimidin-4(3H)-one, (yield: 50%).

Example 13

Following the general procedures set forth in Examples 1-12, the following compounds listed in Table 1 below were prepared. Mass spectrometry was employed with the final compound and at various stages throughout the synthesis as a confirmation of the identity of the product obtained (M+1). For the mass spectrometric analysis, samples were prepared at an approximate concentration of 1 μg/mL in acetonitrile with 0.1% formic acid. Samples were then manually infused into an Applied Biosystems API3000 triple quadrupole mass spectrometer and scanned in Q1 in the range of 50 to 700 m/z.

TABLE 1

| Cmpd No. | Name | Structure | Mass Spec (m/z) |
|---|---|---|---|
| 1 | 2-(6-(4-(3-chlorophenyl)piperazine-1-carbonyl)-5-methyl-4-oxothieno[2,3-d]pyrimidin-3(4H)-yl)-N,N-diethylacetamide | 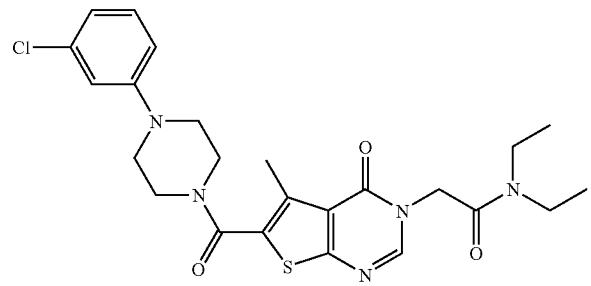 | 502.1 |
| 2 | N,N-diethyl-2-(6-(4-(2-fluorophenyl)piperazine-1-carbonyl)-5-methyl-4-oxothieno[2,3-d]pyrimidin-3(4H)-yl)acetamide | 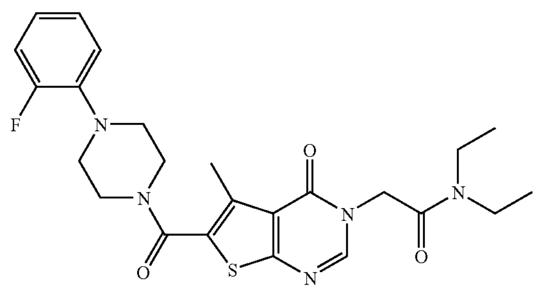 | 486.1 |
| 3 | N,N-diethyl-2-(5-methyl-4-oxo-6-(4-phenylpiperazine-1-carbonyl)thieno[2,3-d]pyrimidin-3(4H)-yl)acetamide | 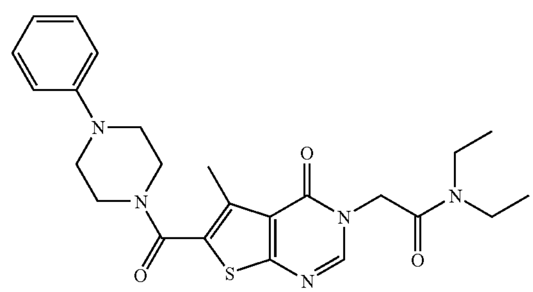 | 468.3 |
| 4 | 2-(6-(4-(2-chlorophenyl)piperazine-1-carbonyl)-5-methyl-4-oxothieno[2,3-d]pyrimidin-3(4H)-yl)-N,N-diethylacetamide | 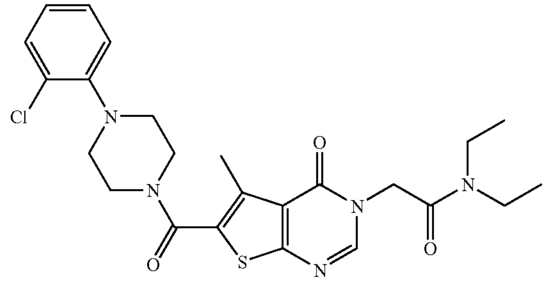 | 502.3 |

TABLE 1-continued

| Cmpd No. | Name | Structure | Mass Spec (m/z) |
|---|---|---|---|
| 5 | 2-(6-(4-(4-chlorophenyl)piperazine-1-carbonyl)-5-methyl-4-oxothieno[2,3-d]pyrimidin-3(4H)-yl)-N,N-diethylacetamide | 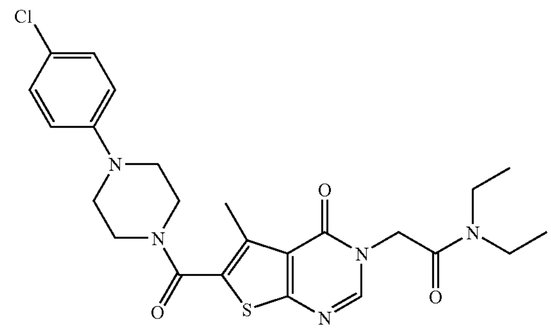 | 502.3 |
| 6 | 2-(6-(4-(3,4-dichlorophenyl)piperazine-1-carbonyl)-5-methyl-4-oxothieno[2,3-d]pyrimidin-3(4H)-yl)-N,N-diethylacetamide | 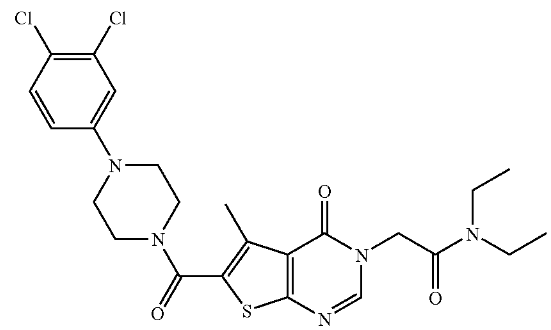 | 536.1 |
| 7 | N,N-diethyl-2-(6-(4-(3-fluorophenyl)piperazine-1-carbonyl)-5-methyl-4-oxothieno[2,3-d]pyrimidin-3(4H)-yl)acetamide | 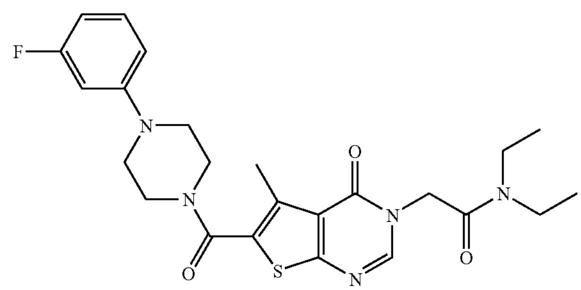 | 486.5 |
| 8 | 2-(6-(4-(4-chloro-3-(trifluoromethyl)phenyl)piperazine-1-carbonyl)-5-methyl-4-oxothieno[2,3-d]pyrimidin-3(4H)-yl)-N,N-diethylacetamide | 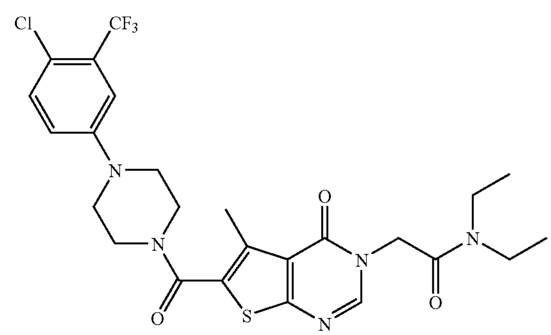 | 570.4 |
| 9 | N,N-diethyl-2-(5-methyl-4-oxo-6-(4-(2-(trifluoromethyl)phenyl)piperazine-1-carbonyl)thieno[2,3-d]pyrimidin-3(4H)-yl)acetamide | 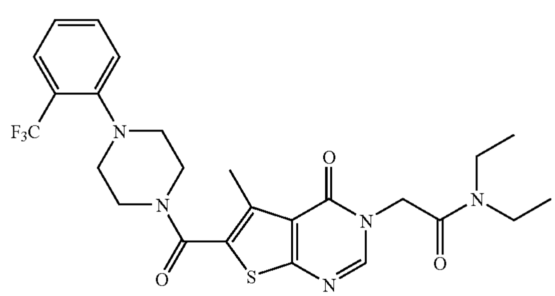 | 536.1 |

TABLE 1-continued

| Cmpd No. | Name | Structure | Mass Spec (m/z) |
|---|---|---|---|
| 10 | N,N-diethyl-2-(5-methyl-4-oxo-6-(4-(4-(trifluoromethyl)phenyl)piperazine-1-carbonyl)thieno[2,3-d]pyrimidin-3(4H)-yl)acetamide | 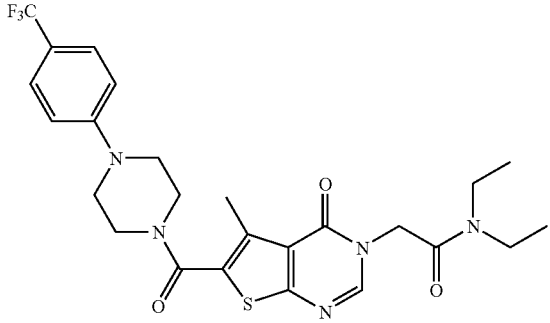 | 536.3 |
| 11 | N-tert-butyl-2-(6-(4-(4-fluorophenyl)piperazine-1-carbonyl)-5-methyl-4-oxothieno[2,3-d]pyrimidin-3(4H)-yl)acetamide | 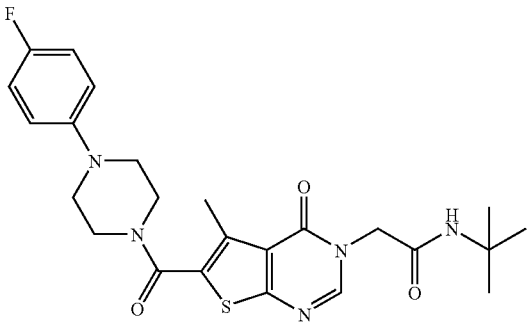 | 486.2 |
| 12 | N-tert-butyl-2-(5-methyl-4-oxo-6-(4-(3-(trifluoromethyl)phenyl)piperazine-1-carbonyl)thieno[2,3-d]pyrimidin-3(4H)-yl)acetamide | 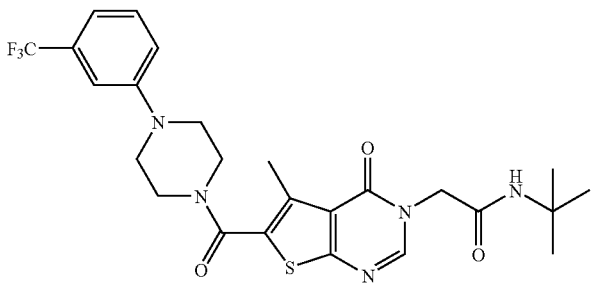 | 536.2 |
| 13 | N-tert-butyl-2-(5-methyl-4-oxo-6-(4-phenylpiperazine-1-carbonyl)thieno[2,3-d]pyrimidin-3(4H)-yl)acetamide | 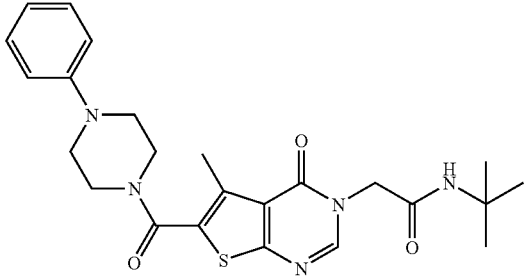 | 468.2 |
| 14 | N-tert-butyl-2-(6-(4-(2-fluorophenyl)piperazine-1-carbonyl)-5-methyl-4-oxothieno[2,3-d]pyrimidin-3(4H)-yl)acetamide | 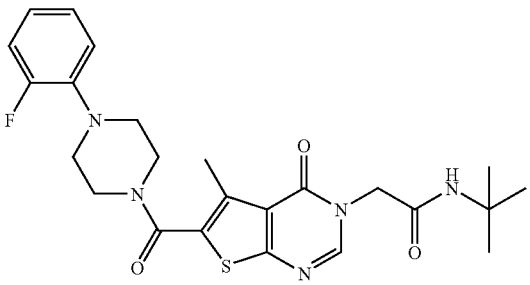 | 486.2 |

TABLE 1-continued

| Cmpd No. | Name | Structure | Mass Spec (m/z) |
|---|---|---|---|
| 15 | N-tert-butyl-2-(6-(4-(4-chlorophenyl)piperazine-1-carbonyl)-5-methyl-4-oxothieno[2,3-d]pyrimidin-3(4H)-yl)acetamide | 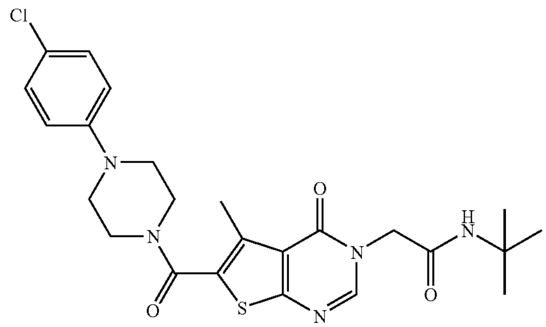 | 502.2 |
| 16 | N-tert-butyl-2-(6-(4-(3-chlorophenyl)piperazine-1-carbonyl)-5-methyl-4-oxothieno[2,3-d]pyrimidin-3(4H)-yl)acetamide | 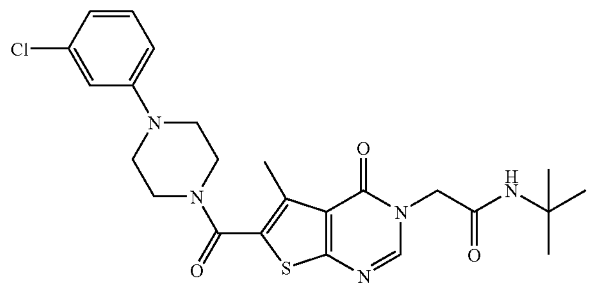 | 502.3 |
| 17 | 2-(6-(4-(3,5-bis(trifluoromethyl)phenyl)piperazine-1-carbonyl)-5-methyl-4-oxothieno[2,3-d]pyrimidin-3(4H)-yl)-N-tert-butylacetamide | 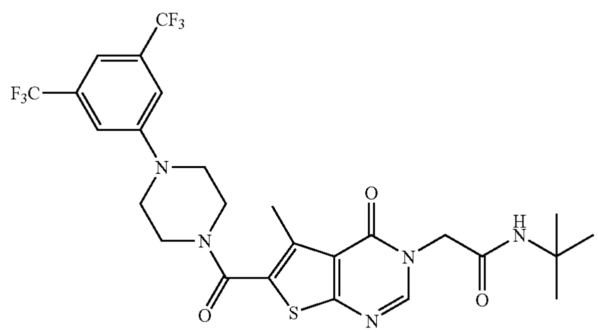 | 604.3 |
| 18 | N-cyclohexyl-2-(5-methyl-4-oxo-6-(4-tertbutylpiperazine-1-carbonyl)thieno[2,3-d]pyrimidin-3(4H)-yl)acetamide | 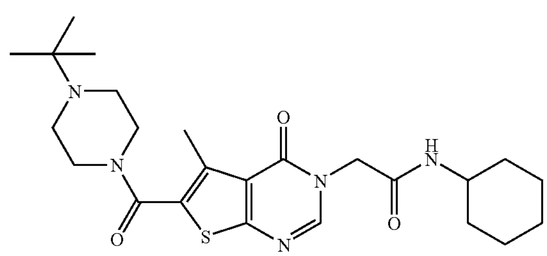 | 474.3 |
| 19 | N-cyclohexyl-2-(5-methyl-4-oxo-6-(4-phenylpiperazine-1-carbonyl)thieno[2,3-d]pyrimidin-3(4H)-yl)acetamide | 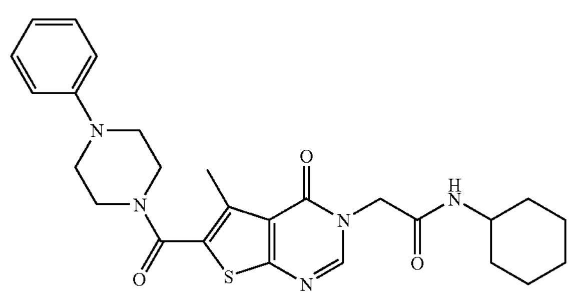 | 494.3 |

TABLE 1-continued

| Cmpd No. | Name | Structure | Mass Spec (m/z) |
|---|---|---|---|
| 20 | 2-(6-(4-(4-chlorophenyl)piperazine-1-carbonyl)-5-methyl-4-oxothieno[2,3-d]pyrimidin-3(4H)-yl)-N-cyclohexylacetamide | 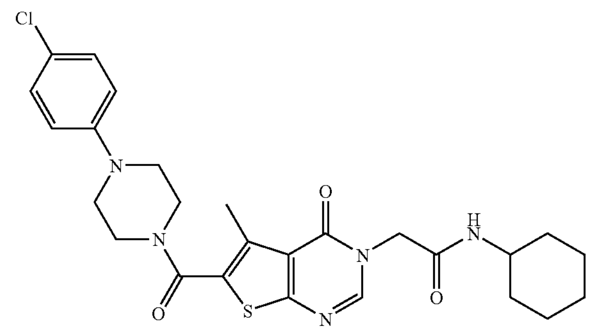 | 528.2 |
| 21 | N-cyclohexyl-2-(6-(4-(3-fluorophenyl)piperazine-1-carbonyl)-5-methyl-4-oxothieno[2,3-d]pyrimidin-3(4H)-yl)acetamide | 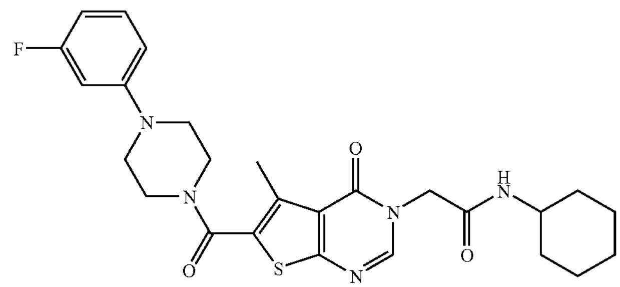 | 512.3 |
| 22 | N-cyclohexyl-2-(6-(4-(4-fluorophenyl)piperazine-1-carbonyl)-5-methyl-4-oxothieno[2,3-d]pyrimidin-3(4H)-yl)acetamide | 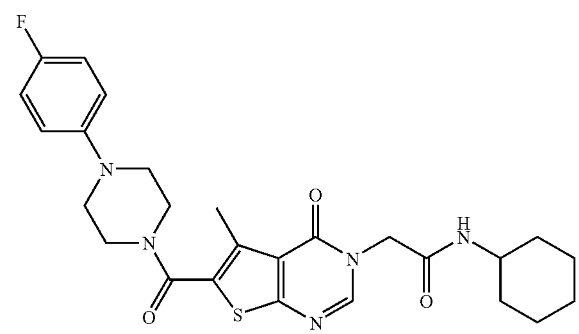 | 512.2 |
| 23 | N-cyclohexyl-2-(6-(4-(2-fluorophenyl)piperazine-1-carbonyl)-5-methyl-4-oxothieno[2,3-d]pyrimidin-3(4H)-yl)acetamide | 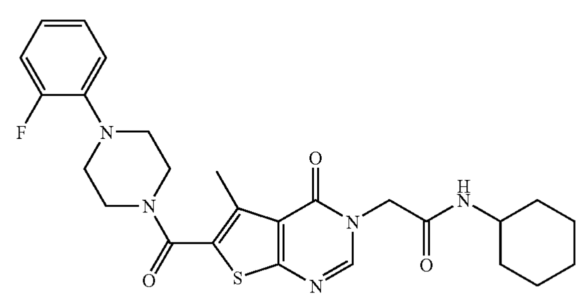 | 512.3 |
| 24 | 2-(6-(4-(3-chlorophenyl)piperazine-1-carbonyl)-5-methyl-4-oxothieno[2,3-d]pyrimidin-3(4H)-yl)-N-cyclohexylacetamide | 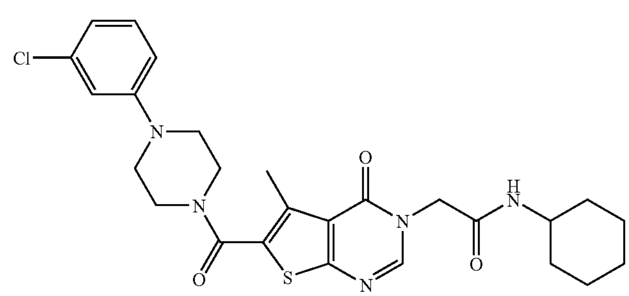 | 528.3 |

TABLE 1-continued

| Cmpd No. | Name | Structure | Mass Spec (m/z) |
|---|---|---|---|
| 25 | N-cyclohexyl-2-(6-(4-(3,4-dichlorophenyl)piperazine-1-carbonyl)-5-methyl-4-oxothieno[2,3-d]pyrimidin-3(4H)-yl)acetamide | 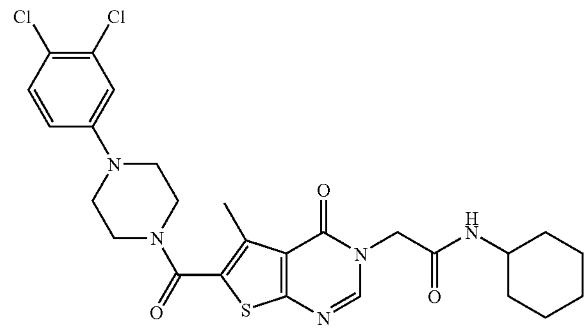 | 562.0 |
| 26 | N-cyclohexyl-2-(5-methyl-4-oxo-6-(piperidine-1-carbonyl)thieno[2,3-d]pyrimidin-3(4H)-yl)acetamide | 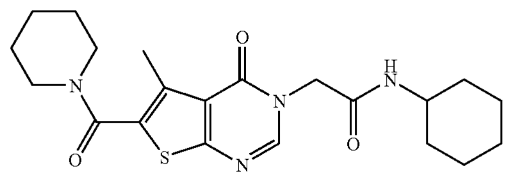 | 417.1 |
| 27 | N-cyclohexyl-2-(6-(4-(3-methoxyphenyl)piperazine-1-carbonyl)-5-methyl-4-oxothieno[2,3-d]pyrimidin-3(4H)-yl)acetamide | 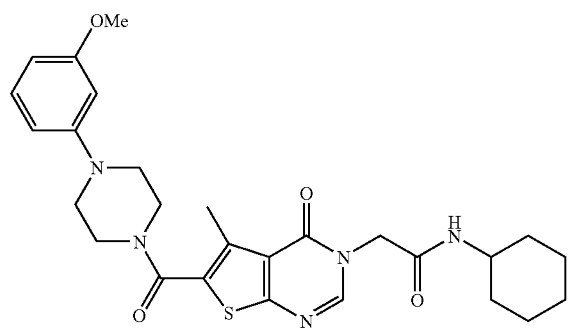 | 524.4 |
| 28 | N-cyclohexyl-2-(5-methyl-6-(4-(4-methoxy phenyl)piperazine-1-carbonyl)-4-oxothieno[2,3-d]pyrimidin-3(4H)-yl)acetamide | 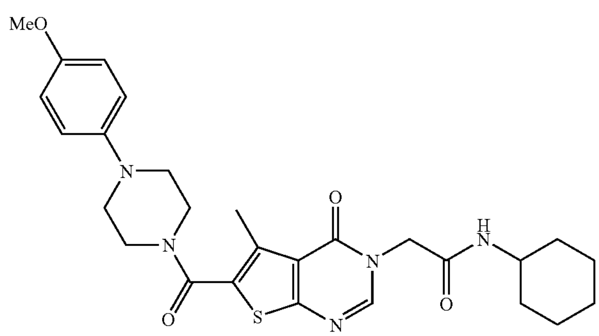 | 523.3 |
| 29 | N-cyclohexyl-2-(5-methyl-6-(4-(3-nitrophenyl)piperazine-1-carbonyl)-4-oxothieno[2,3-d]pyrimidin-3(4H)-yl)acetamide | 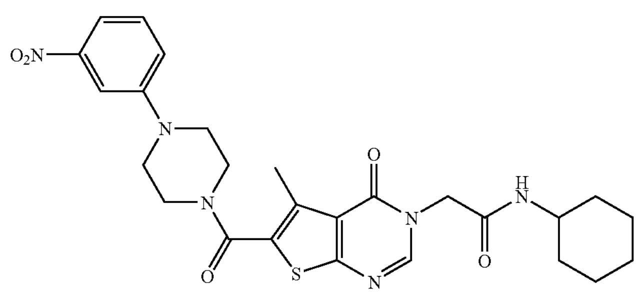 | 539.5 |

TABLE 1-continued

| Cmpd No. | Name | Structure | Mass Spec (m/z) |
|---|---|---|---|
| 30 | N-(4,4-difluorocyclohexyl)-2-(5-methyl-4-oxo-6-(4-(phenyl piperazine-1-carbonyl)thieno[2,3-d]pyrimidin-3-(4H)-yl)acetamide | 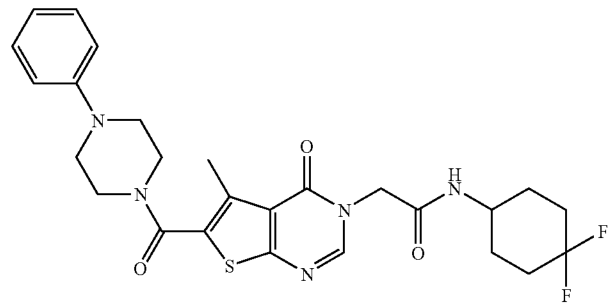 | 530.1 |
| 31 | N-(4,4-difluorocyclohexyl)-2-(5-methyl-4-oxo-6-(4-(2-fluorophenyl)piperazine-1-carbonyl)thieno[2,3-d]pyrimidin-3-(4H)-yl)acetamide | 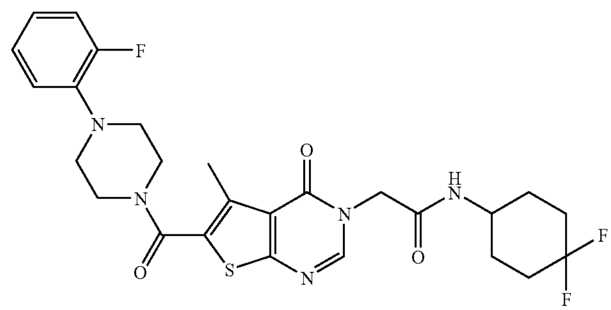 | 548.0 |
| 32 | N-(4,4-difluorocyclohexyl)-2-(5-methyl-4-oxo-6-(4-(3-chlorophenyl)piperazine-1-carbonyl)thieno[2,3-d]pyrimidin-3-(4H)-yl)acetamide | 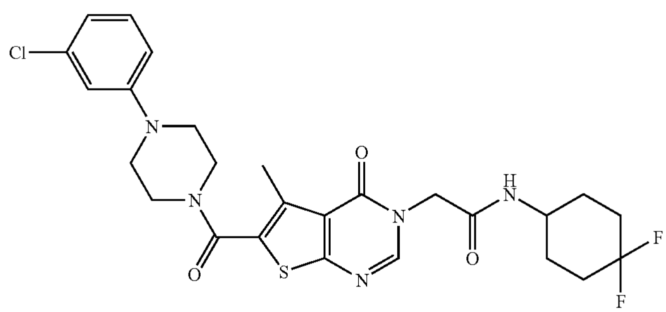 | 564.2 |
| 33 | N-cyclohexyl-2-(5-methyl-4-oxo-6-(4-phenylpiperazine-1-carbonyl)thieno[2,3-d]pyrimidin-3(4H)-yl)propanamide | 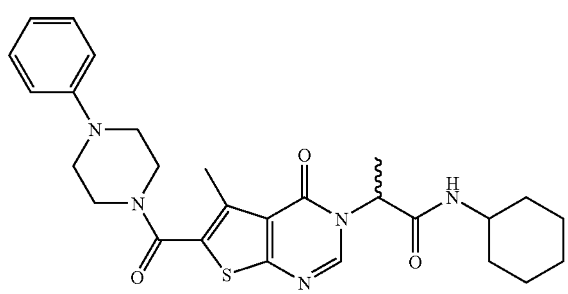 | 508.1 |
| 34 | N-cyclohexyl-2-(6-(4-(2-fluorophenyl)piperazine-1-carbonyl)-5-methyl-4-oxothieno[2,3-d]pyrimidin-3(4H)-yl)propanamide | 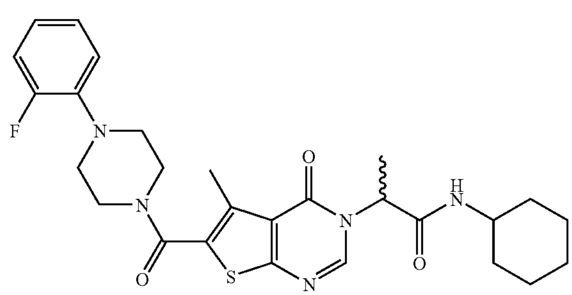 | 526.3 |

TABLE 1-continued

| Cmpd No. | Name | Structure | Mass Spec (m/z) |
|---|---|---|---|
| 35 | N-cyclohexyl-2-(6-(4-(3-chlorophenyl)piperazine-1-carbonyl)-5-methyl-4-oxothieno[2,3-d]pyrimidin-3(4H)-yl)propanamide | 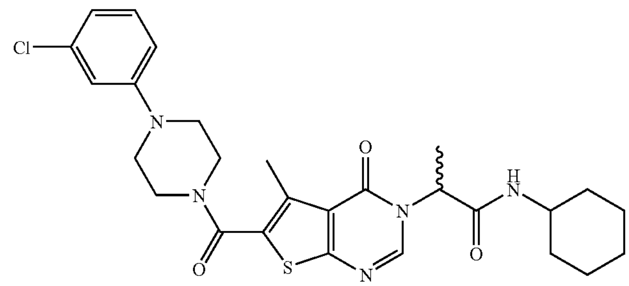 | 542.2 |
| 36 | N-cyclopentyl-2-(6-(4-(2-fluorophenyl)piperazine-1-carbonyl)-5-methyl-4-oxothieno[2,3-d]pyrimidin-3(4H)-yl)acetamide | 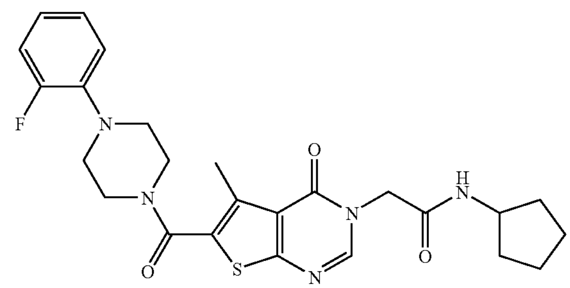 | 498.4 |
| 37 | 2-(6-(4-(3-chlorophenyl)piperazine-1-carbonyl)-5-methyl-4-oxothieno[2,3-d]pyrimidin-3(4H)-yl)-N-cyclopentylacetamide | 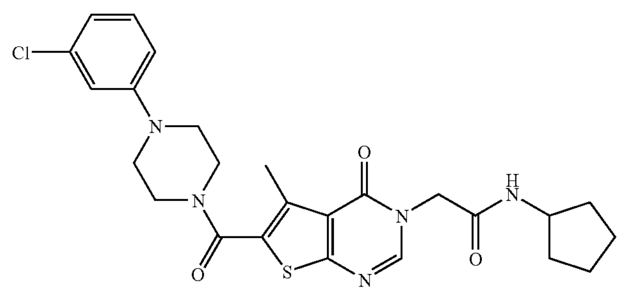 | 514.0 |
| 38 | 2-(6-(4-(4-chloro-3-(trifluoromethyl)phenyl)piperazine-1-carbonyl)-5-methyl-4-oxothieno[2,3-d]pyrimidin-3(4H)-yl)-N-cyclopentylacetamide | 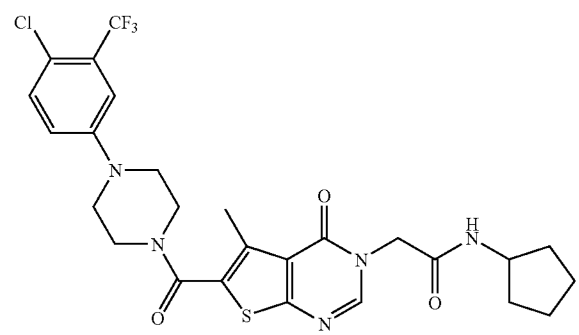 | 582.3 |
| 39 | N-cyclopentyl-2-(5-methyl-6-(4-methylpiperazine-1-carbonyl)-4-oxothieno[2,3-d]pyrimidin-3(4H)-yl)acetamide | 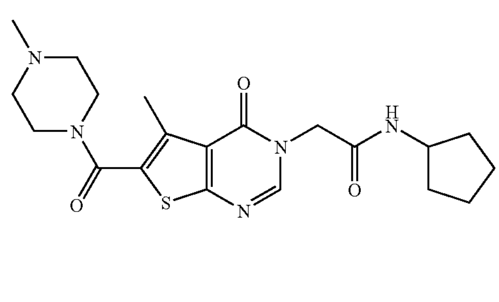 | 418.3 |

TABLE 1-continued

| Cmpd No. | Name | Structure | Mass Spec (m/z) |
|---|---|---|---|
| 40 | N-cyclopentyl-2-(5-methyl-6-(4-tertbutylpiperazine-1-carbonyl)-4-oxothieno[2,3-d]pyrimidin-3(4H)-yl)acetamide | 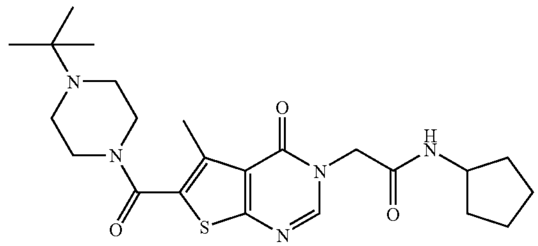 | 460.2 |
| 41 | N-cyclopentyl-2-(5-methyl-4-oxo-6-(4-phenylpiperazine-1-carbonyl)thieno[2,3-d]pyrimidin-3(4H)-yl)acetamide | 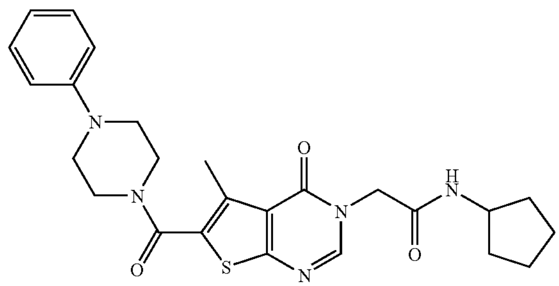 | 480.3 |
| 42 | 2-(6-(4-(4-chlorophenyl)piperazine-1-carbonyl)-5-methyl-4-oxothieno[2,3-d]pyrimidin-3(4H)-yl)-N-cyclopentylacetamide | 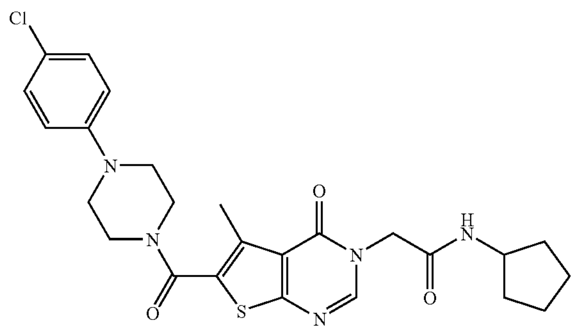 | 514.3 |
| 43 | N-cyclopentyl-2-(6-(4-(3-methoxyphenyl)piperazine-1-carbonyl)-5-methyl-4-oxothieno[2,3-d]pyrimidin-3(4H)-yl)acetamide | 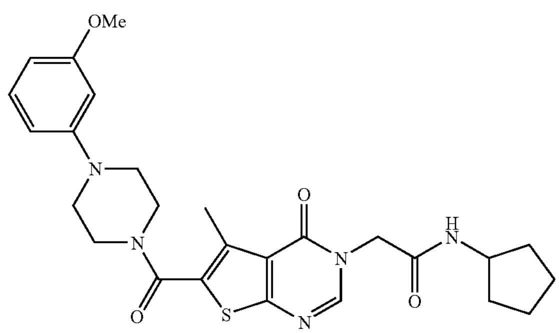 | 510.3 |
| 44 | N-cyclopentyl-2-(6-(4-(4-methoxyphenyl)piperazine-1-carbonyl)-5-methyl-4-oxothieno[2,3-d]pyrimidin-3(4H)-yl)acetamide | 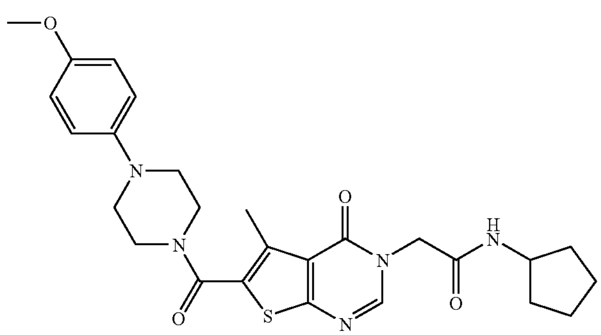 | 510.2 |

TABLE 1-continued

| Cmpd No. | Name | Structure | Mass Spec (m/z) |
|---|---|---|---|
| 45 | N-cyclopentyl-2-(6-(4-(3-nitrophenyl)piperazine-1-carbonyl)-5-methyl-4-oxothieno[2,3-d]pyrimidin-3(4H)-yl)acetamide | 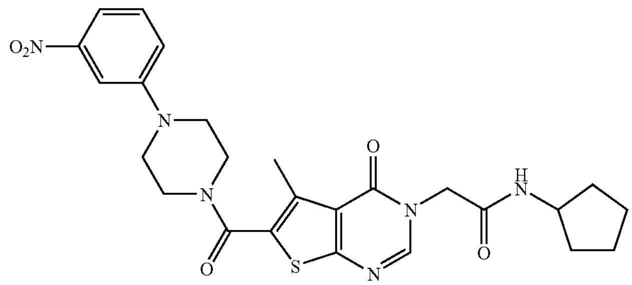 | 525.2 |
| 46 | N-cyclopentyl-2-(5-methyl-4-oxo-6-(4-phenylpiperazine-1-carbonyl)thieno[2,3-d]pyrimidin-3(4H)-yl)propanamide | 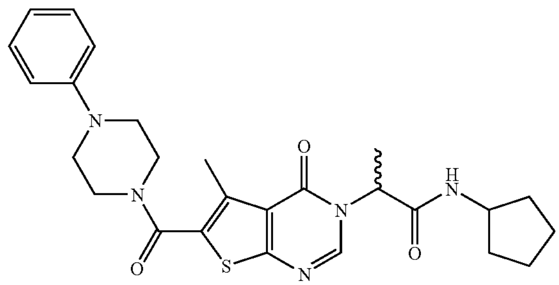 | 494.3 |
| 47 | N-cyclopentyl-2-(6-(4-(2-fluorophenyl)piperazine-1-carbonyl)-5-methyl-4-oxothieno[2,3-d]pyrimidin-3(4H)-yl)propanamide | 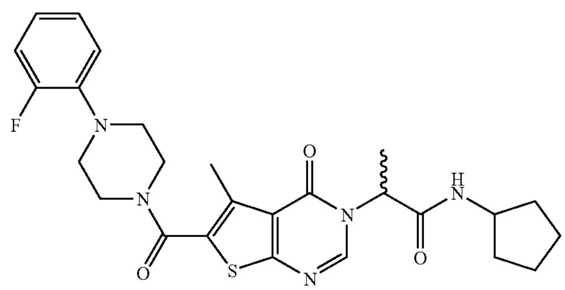 | 512.3 |
| 48 | N-cyclopentyl-2-(6-(4-(4-fluorophenyl)piperazine-1-carbonyl)-5-methyl-4-oxothieno[2,3-d]pyrimidin-3(4H)-yl)propanamide | 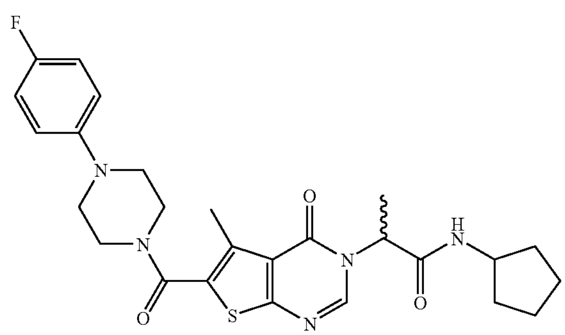 | 512.4 |
| 49 | N-cyclopropyl-2-(5-methyl-4-oxo-6-(4-phenylpiperazine-1-carbonyl)thieno[2,3-d]pyrimidin-3(4H)-yl)acetamide | 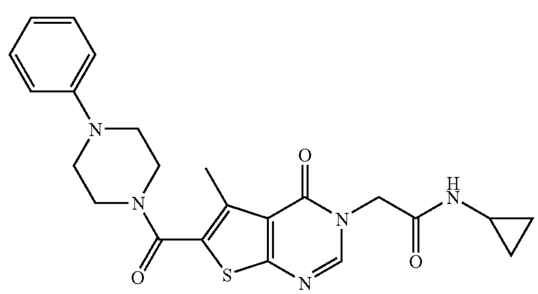 | 452.2 |

TABLE 1-continued

| Cmpd No. | Name | Structure | Mass Spec (m/z) |
|---|---|---|---|
| 50 | N-cyclopropyl-2-(6-(4-(2-fluorophenyl)piperazine-1-carbonyl)-5-methyl-4-oxothieno[2,3-d]pyrimidin-3(4H)-yl)acetamide | 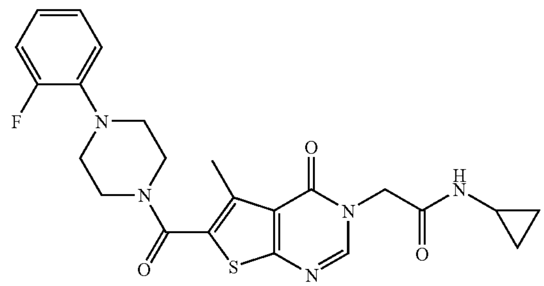 | 470.2 |
| 51 | 2-(6-(4-(2-fluorophenyl)piperazine-1-carbonyl)-5-methyl-4-oxothieno[2,3-d]pyrimidin-3(4H)-yl)-N-phenylacetamide | 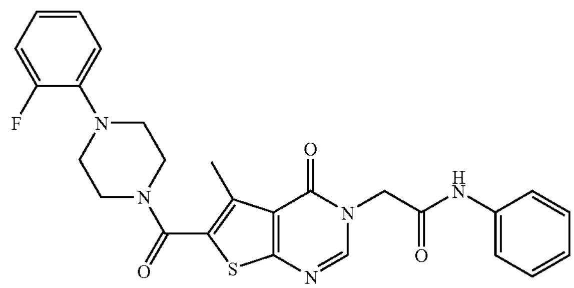 | 506.4 |
| 52 | 2-(5-methyl-4-oxo-6-(4-phenylpiperazine-1-carbonyl)thieno[2,3-d]pyrimidin-3(4H)-yl)-N-phenylacetamide | 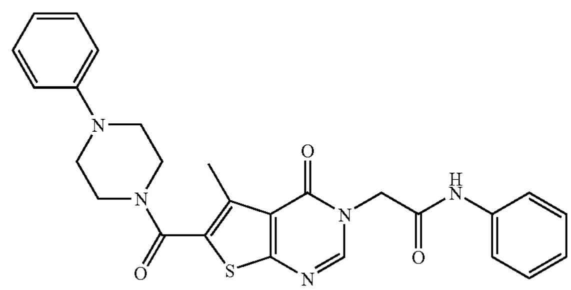 | 488.2 |
| 53 | 2-(6-(4-(3,5-bis(trifluoromethyl)phenyl)piperazine-1-carbonyl)-5-methyl-4-oxothieno[2,3-d]pyrimidin-3(4H)-yl)-N-phenylacetamide | 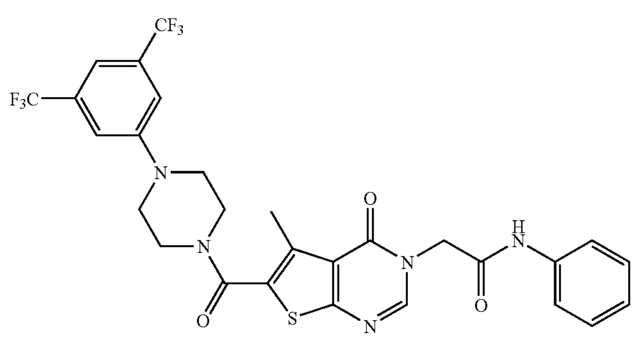 | 624.3 |
| 54 | 2-(5-methyl-6-(4-methylpiperazine-1-carbonyl)-4-oxothieno[2,3-d]pyrimidin-3(4H)-yl)-N-phenylacetamide | 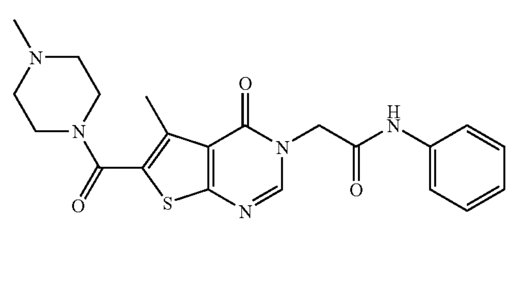 | 426.2 |

TABLE 1-continued

| Cmpd No. | Name | Structure | Mass Spec (m/z) |
|---|---|---|---|
| 55 | 2-(6-(4-phenylpiperazine-1-carbonyl)-5-methyl-4-oxothieno[2,3-d]pyrimidin-3(4H)-yl)-N-(3,5-difluorophenyl)acetamide | 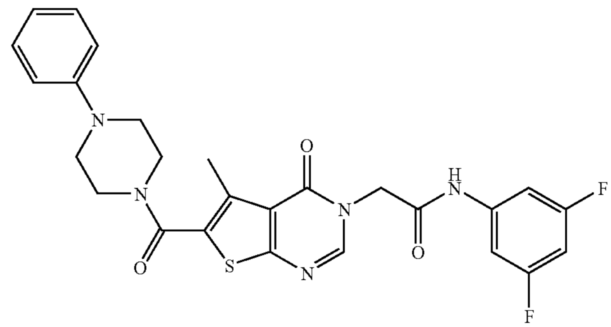 | 524.2 |
| 56 | 2-(6-(4-(3-chlorophenyl)piperazine-1-carbonyl)-5-methyl-4-oxothieno[2,3-d]pyrimidin-3(4H)-yl)-N-(3,5-difluorophenyl)acetamide | 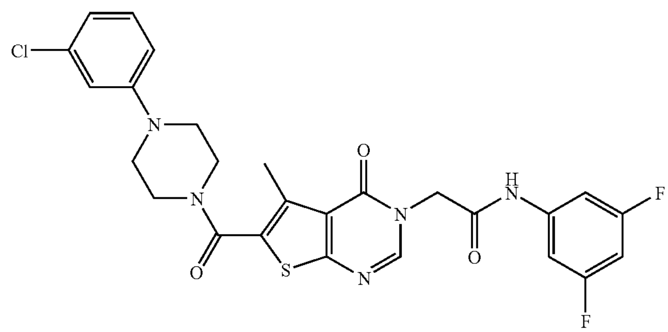 | 558.0 |
| 57 | (S)-N-(3,5-difluorophenyl)-2-(6-(3-fluoropyrrolidin-1-carbonyl)-5-methyl-4-oxothieno[2,3-d]pyrimidin-3(4H)-yl)acetamide | 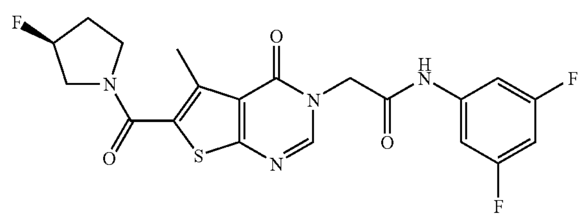 | 451.5 |
| 58 | (S)-N-(3,5-difluorophenyl)-2-(6-(3,3-difluoropyrrolidin-1-carbonyl)-5-methyl-4-oxothieno[2,3-d]pyrimidin-3(4H)-yl)acetamide | 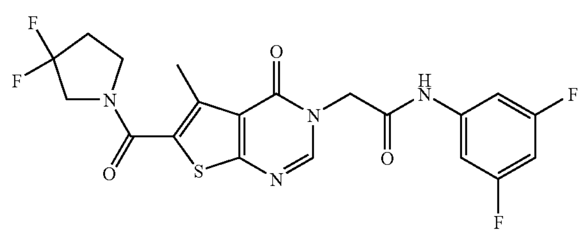 | 469.0 |
| 59 | N-(3,5-difluorophenyl)-2-(6-(4-fluoropiperidin-1-carbonyl)-5-methyl-4-oxothieno[2,3-d]pyrimidin-3(4H)-yl)acetamide | 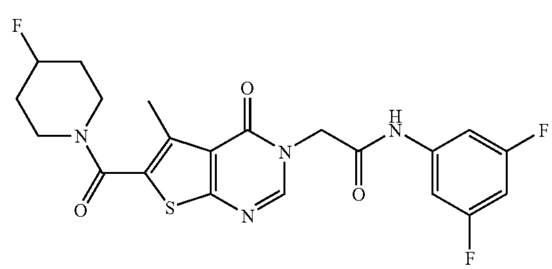 | 465.4 |

TABLE 1-continued

| Cmpd No. | Name | Structure | Mass Spec (m/z) |
|---|---|---|---|
| 60 | N-(3,5-difluorophenyl)-2-(6-(4,4-difluoropiperidin-1-carbonyl)-5-methyl-4-oxothieno[2,3-d]pyrimidin-3(4H)-yl)acetamide | 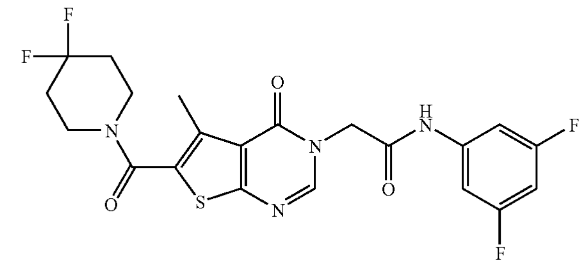 | 483.0 |
| 61 | N-(3,5-difluorophenyl)-2-(6-(3,3-difluoropiperidin-1-carbonyl)-5-methyl-4-oxothieno[2,3-d]pyrimidin-3(4H)-yl)acetamide | 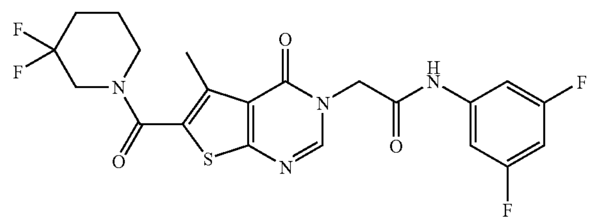 | 483.5 |
| 62 | 2-(6-(4-(2-fluorophenyl)piperazine-1-carbonyl)-5-methyl-4-oxothieno[2,3-d]pyrimidin-3(4H)-yl)-N-(3-(trifluoromethyl)phenyl)acetamide | 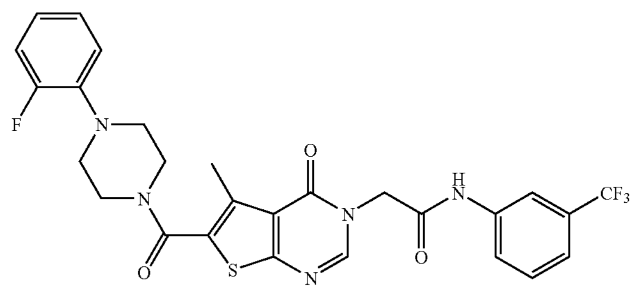 | 574.1 |
| 63 | 2-(5-methyl-(4-oxo-6-(4-(trifluoromethyl)piperidin-1-carbonyl)thieno[2,3-d]pyrimidin-3(4H)-yl)-N-(3-(trifluoromethyl)phenyl)acetamide | 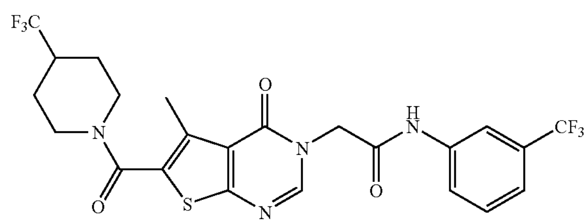 | 546.6 |
| 64 | N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide | 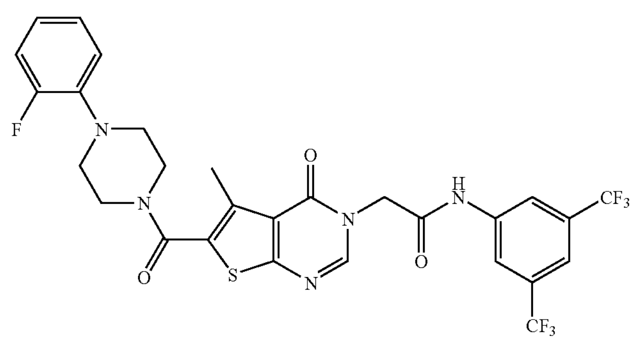 | 642.5 |
| 65 | N-(3,5-bis(trifluoromethyl)phenyl)-2-(5-methyl-4-oxo-6-(piperazine-1-carbonyl)thieno[2,3-d]pyrimidin-3(4H)-yl)acetamide | 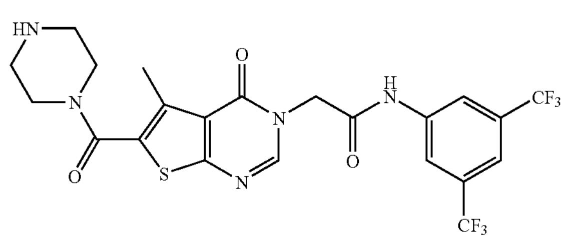 | 548.4 |

TABLE 1-continued

| Cmpd No. | Name | Structure | Mass Spec (m/z) |
|---|---|---|---|
| 66 | 3-(2-(3,5-bis(trifluoromethyl)phenylamino)-2-oxoethyl)-N,5-dimethyl-4-oxo-3,4-dihydrothieno[2,3-d]pyrimidine-6-carboxamide | 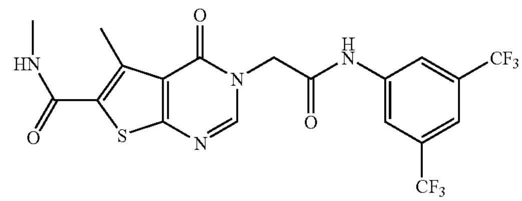 | 493.2 |
| 67 | 3-(2-(3,5-bis(trifluoromethyl)phenylamino)-2-oxoethyl)-5-methyl-4-oxo-3,4-dihydrothieno[2,3-d]pyrimidine-6-carboxamide | 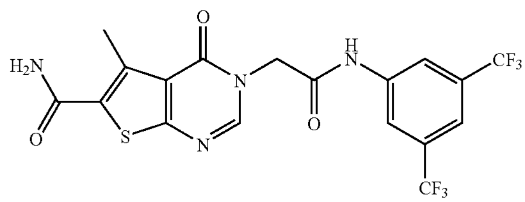 | 479.0 |
| 68 | 3-(2-(3,5-bis(trifluoromethyl)phenylamino)-2-oxoethyl)-N-tert-butyl-5-methyl-4-oxo-3,4-dihydrothieno[2,3-d]pyrimidine-6-carboxamide | 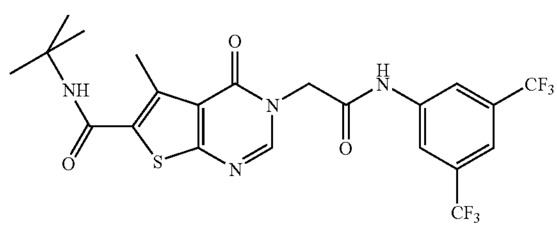 | 535.0 |
| 69 | N-(3,5-bis(trifluoromethyl)phenyl)-2-(5-methyl-4-oxo-6-(piperidine-1-carbonyl)thieno[2,3-d]pyrimidin-3(4H)-yl)acetamide | 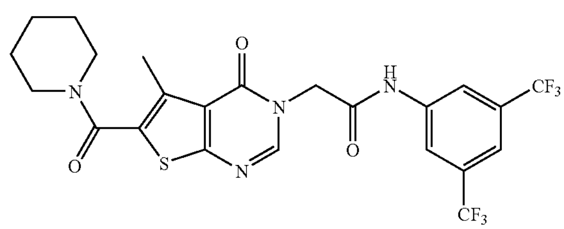 | 547.2 |
| 70 | N-(3,5-bis(trifluoromethyl)phenyl)-2-(5-methyl-4-oxo-6-(pyrrolidine-1-carbonyl)thieno[2,3-d]pyrimidin-3(4H)-yl)acetamide | 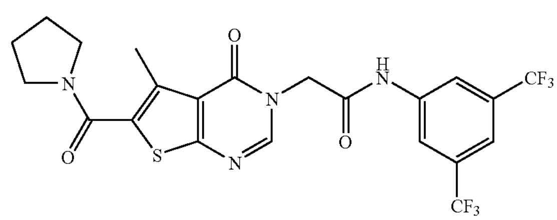 | 533.2 |
| 71 | (S)-N-(3,5-bis(trifluoromethyl)phenyl)-2-(5-methyl-4-oxo-6-(3-fluoropyrrolidine-1-carbonyl)thieno[2,3-d]pyrimidin-3(4H)-yl)acetamide | 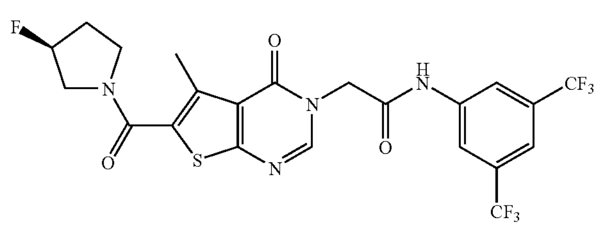 | 551.1 |

TABLE 1-continued

| Cmpd No. | Name | Structure | Mass Spec (m/z) |
|---|---|---|---|
| 72 | N-(3,5-bis(trifluoromethyl)phenyl)-2-(5-methyl-4-oxo-6-(4-fluoropiperidine-1-carbonyl)thieno[2,3-d]pyrimidin-3(4H)-yl)acetamide | 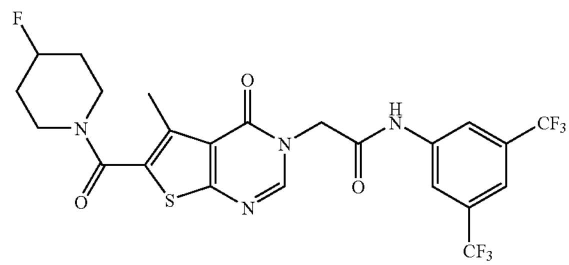 | 565.2 |
| 73 | 6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one | 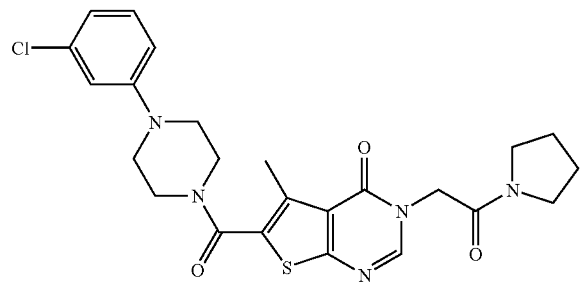 | 500.1 |
| 74 | 5-methyl-3-(2-oxo-2-(pyrrolidin-1-yl)ethyl)-6-(4-phenylpiperazine-1-carbonyl)thieno[2,3-d]pyrimidin-4(3H)-one | 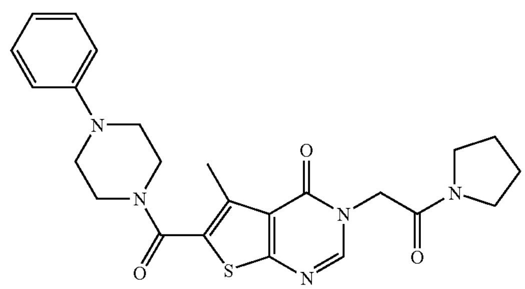 | 466.3 |
| 75 | (R)-6-(4-(3-chlorophenyl)-piperazine-1-carbonyl)-3-(2-(3-fluoropyrrolidin-1-yl)-2-oxoethyl)-5-methylthieno[2,3-d]pyrimidin-4(3H)-one | 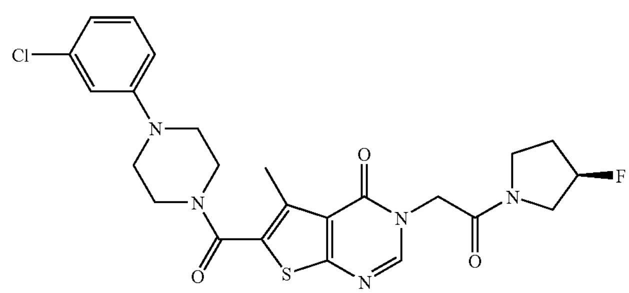 | 518.2 |
| 76 | (S)-6-(4-(3-chlorophenyl)-piperazine-1-carbonyl)-3-(2-(3-fluoropyrrolidin-1-yl)-2-oxoethyl)-5-methylthieno[2,3-d]pyrimidin-4(3H)-one | 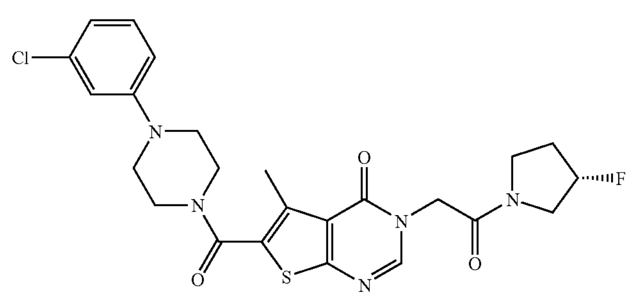 | 518.3 |

TABLE 1-continued

| Cmpd No. | Name | Structure | Mass Spec (m/z) |
|---|---|---|---|
| 77 | (S)-6-(4-(2-fluorophenyl)-piperazine-1-carbonyl)-3-(2-(3-fluoropyrrolidin-1-yl)-2-oxoethyl)-5-methylthieno[2,3-d]pyrimidin-4(3H)-one | 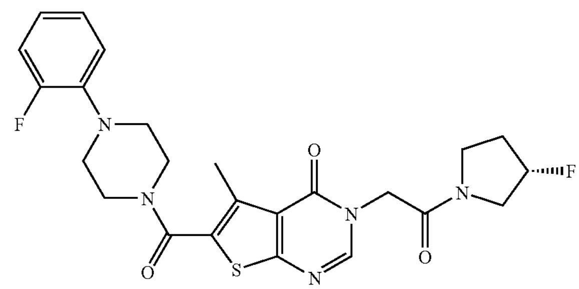 | 502.2 |
| 78 | 6-(4-(3-chlorophenyl)-piperazine-1-carbonyl)-3-(2-(3,3-difluoropyrrolidin-1-yl)-2-oxoethyl)-5-methylthieno[2,3-d]pyrimidin-4(3H)-one | 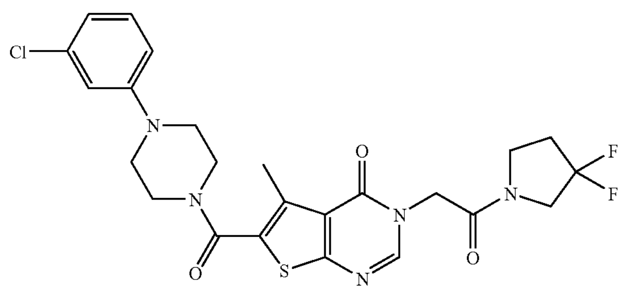 | 536.1 |
| 79 | 3-(2-(3,3-difluoropyrrolidin-1-yl)-2-oxoethyl)-6-(4-(2-fluorophenyl)piperazine-1-carbonyl)-5-methylthieno[2,3-d]pyrimidin-4(3H)-one | 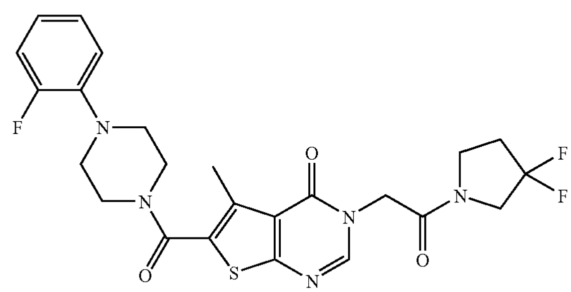 | 520.4 |
| 80 | 6-(4-(3-chlorophenyl)piperazine-1-carbonyl)-5-methyl-3-(2-oxo-2-(2-trifluoromethyl)pyrrolidin-1-yl)ethyl)thieno[2,3-d]pyrimidin-4(3H)-one | 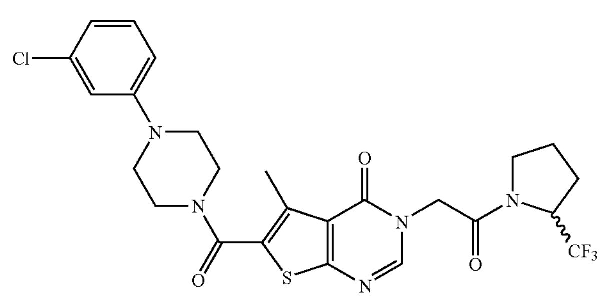 | 568.3 |
| 81 | 6-(4-(2-fluorophenyl)piperazine-1-carbonyl)-5-methyl-3-(2-oxo-2-(piperidin-1-yl)ethyl)thieno[2,3-d]pyrimidin-4(3H)-one | 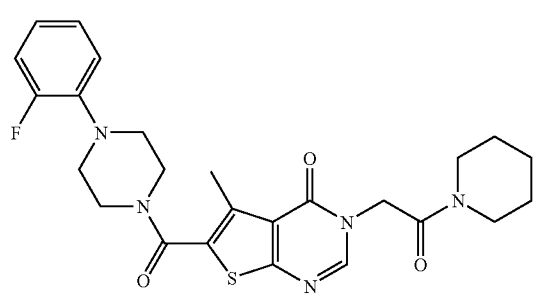 | 498.2 |

TABLE 1-continued

| Cmpd No. | Name | Structure | Mass Spec (m/z) |
|---|---|---|---|
| 82 | 6-(4-(3-chlorophenyl)piperazine-1-carbonyl)-5-methyl-3-(2-(3-methylpiperidin-1-yl)-2-oxoethyl)thieno[2,3-d]pyrimidin-4(3H)-one | 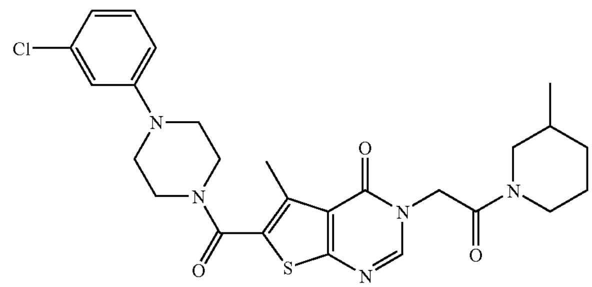 | 528.4 |
| 83 | 6-(4-(2-fluorophenyl)piperazine-1-carbonyl)-5-methyl-3-(2-(4-methylpiperidin-1-yl)-2-oxoethyl)thieno[2,3-d]pyrimidin-4(3H)-one | 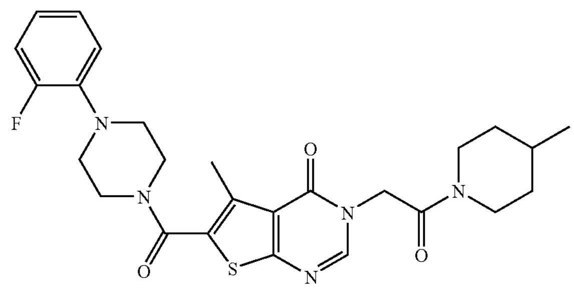 | 512.4 |
| 84 | 4-(2-(4-fluoropiperidin-1-yl)-2-oxoethyl)-6-(4-(3-chloro phenyl)piperazine-1-carbonyl)-5-methylthieno[2,3-d]pyrimidin-4(3H)-one | 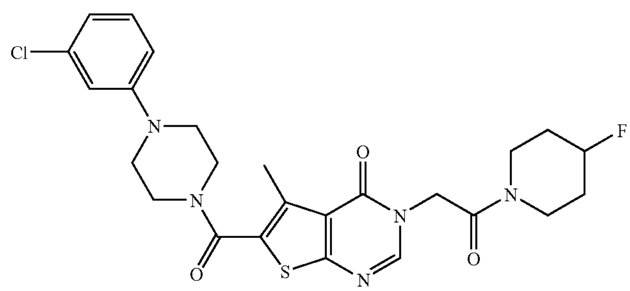 | 531.8 |
| 85 | 3-(2-(3,3-difluoropiperidin-1-yl)-2-oxoethyl)-6-(4-(2-fluorophenyl)piperazine-1-carbonyl)-5-mehtylthieno[2,3-d]pyrimidin-4(3H)-one | 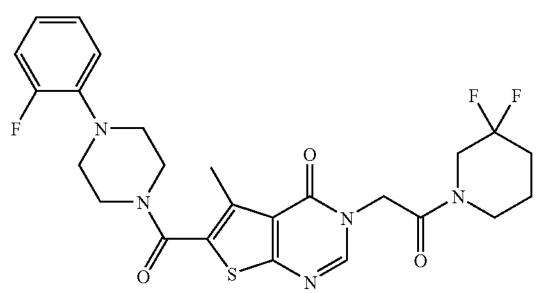 | 534.2 |
| 86 | 3-(2-(3,3-difluoropiperidin-1-yl)-2-oxoethyl)-6-(4-(3-chlorophenyl)piperazine-1-carbonyl)-5-methylthieno[2,3-d]pyrimidin-4(3H)-one | 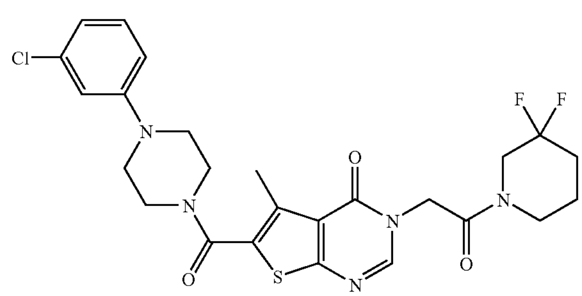 | 550.4 |

TABLE 1-continued

| Cmpd No. | Name | Structure | Mass Spec (m/z) |
|---|---|---|---|
| 87 | 6-(4-(3-chlorophenyl)piperazine-1-carbonyl)-3-(2-(4,4-difluoropiperidin-1-yl)-2-oxoethyl)-5-methylthieno[2,3-d]pyrimidin-4(3H)-one | 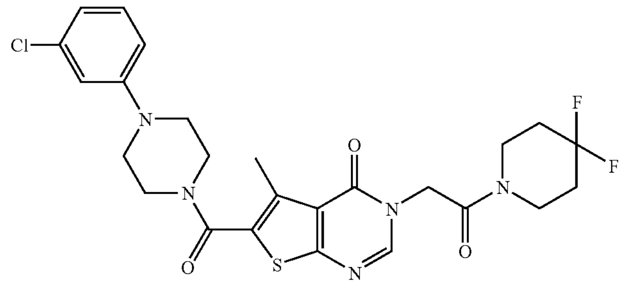 | 550.5 |
| 88 | 3-(2-(4,4-difluoropiperidin-1-yl)-2-oxoethyl)-6-(4-(2-fluorophenyl)piperazine-1-carbonyl)-5-methylthieno[2,3-d]pyrimidin-4(3H)-one | 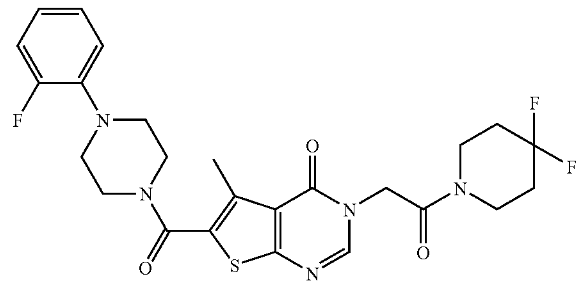 | 534.1 |
| 89 | 6-(4-(2-fluorophenyl)piperazine-1-carbonyl)-5-methyl-3-(2-oxo-2-((4-trifluoromethyl)piperidin-1-yl)ethyl)thieno[2,3-d]pyrimidin-4(3H)-one | 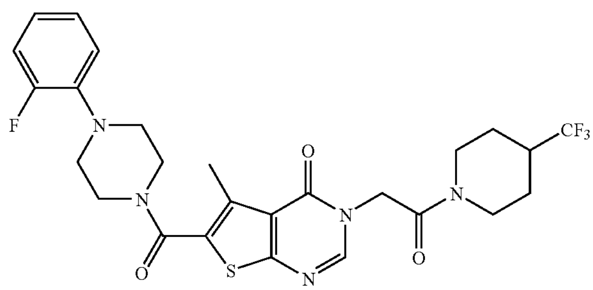 | 566.4 |
| 90 | 3-(2-(3,3-difluoropiperidin-1-yl)-2-oxoethyl)-6-(4-(4-fluorophenyl)piperazine-1-carbonyl)-5-methylthieno[2,3-d]pyrimidin-4(3H)-one | 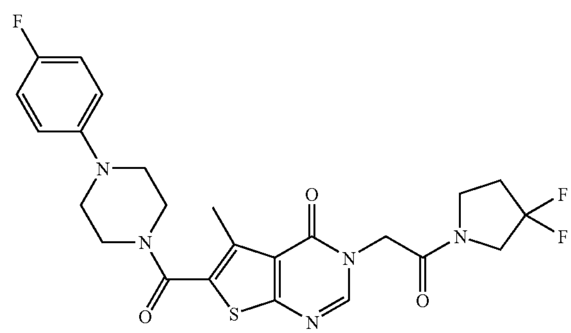 | 520.1 |
| 91 | (S)-6-(4-(4-fluorophenyl)-piperazine-1-carbonyl)-3-(2-(3-fluoropyrrolidin-1-yl)-2-oxoethyl)-5-methylthieno[2,3-d]pyrimidin-4(3H)-one | 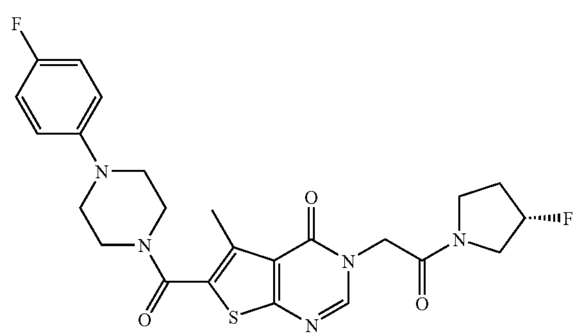 | 502.2 |

TABLE 1-continued

| Cmpd No. | Name | Structure | Mass Spec (m/z) |
|---|---|---|---|
| 92 | 5-methyl-3-(2-(2-oxopyrrolidin-1-yl)ethyl)-6-(4-phenylpiperazine-1-carbonyl)thieno[2,3-d]pyrimidin-4(3H)-one | 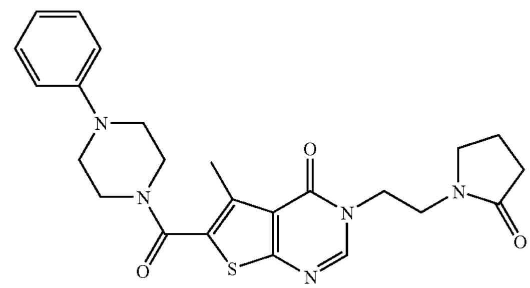 | 466.4 |
| 93 | 6-(4-(3,5-bis(trifluoromethyl)phenyl)piperazine-1-carbonyl)-5-methyl-3-(2-(2-oxopyrrolidin-1-yl)ethyl)thieno[2,3-d]pyrimidin-4(3H)-one | 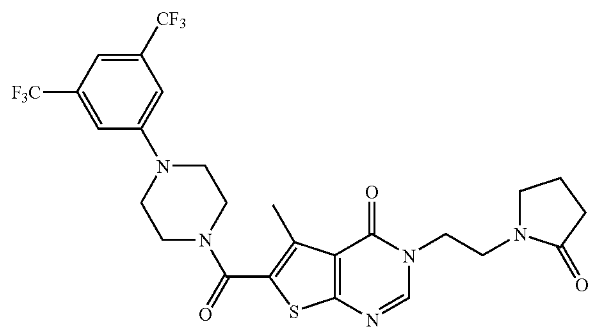 | 602.2 |
| 94 | 6-(4-(4-chlorophenyl)piperazine-1-carbonyl)-5-methyl-3-(2-(2-oxopyrrolidin-1-yl)ethyl)thieno[2,3-d]pyrimidin-4(3H)-one | 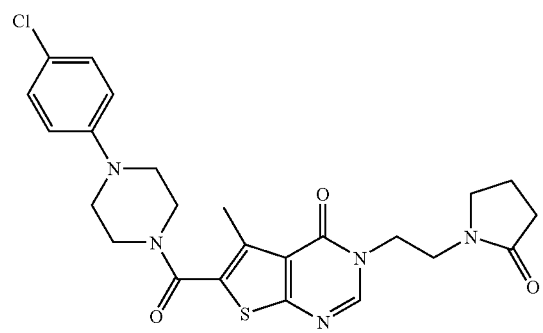 | 500.4 |
| 95 | 6-(4-(2-fluorophenyl)piperazine-1-carbonyl)-5-methyl-3-(2-(2-oxopyrrolidin-1-yl)ethyl)thieno[2,3-d]pyrimidin-4(3H)-one | 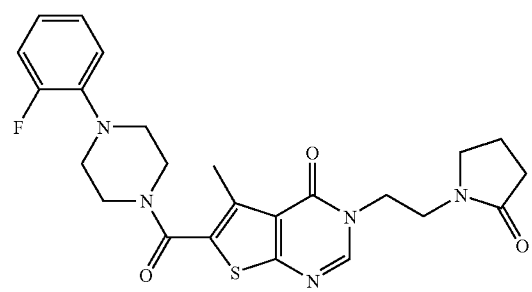 | 484.2 |
| 96 | 2-(5-methyl-4-oxo-6-(4-phenylpiperazine-1-carbonyl)thieno[2,3-d]pyrimidin-3(4H)-yl)-N-(2,2,2-trifluoroethyl)acetamide | 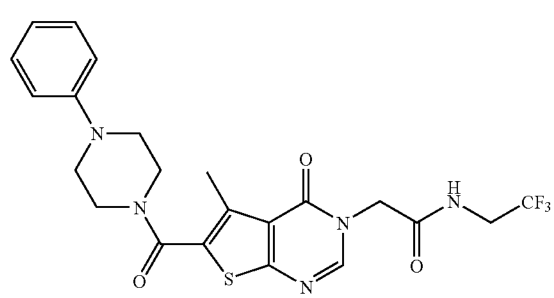 | 494.4 |

TABLE 1-continued

| Cmpd No. | Name | Structure | Mass Spec (m/z) |
|---|---|---|---|
| 97 | 3-benzyl-N,N,5-trimethyl-4-oxo-3,4-dihydrothieno[2,3-d]pyrimidine-6-carboxamide | 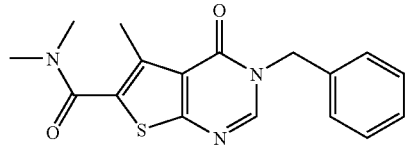 | 328.0 |
| 98 | 3-(2-fluorobenzyl)-N,N,5-trimethyl-4-oxo-3,4-dihydrothieno[2,3-d]pyrimidine-6-carboxamide | 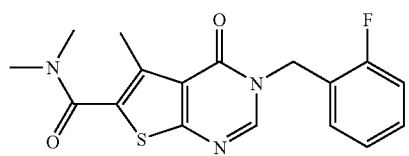 | 346.3 |
| 99 | 6-(3,5-dimethylpiperazine-1-carbonyl)-3-(2-fluorobenzyl)-5-methylthieno[2,3-d]pyrimidin-4(3H)-one | 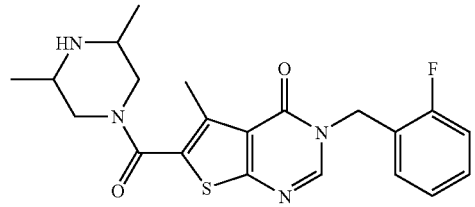 | 415.2 |
| 100 | 3-(2-fluorobenzyl)-5-methyl-6-(piperazine-1-carbonyl)thieno[2,3-d]pyrimidin-4(3H)-one | 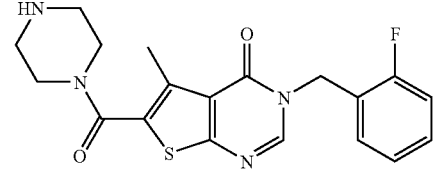 | 387.2 |
| 101 | 6-(4-(3-chlorophenyl)piperazine-1-carbonyl)-3-(2-fluorobenzyl)-5-methyl thieno[2,3-d]pyrimidin-4(3H)-one | 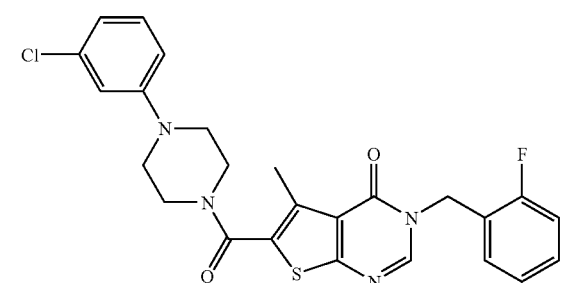 | 477.3 |
| 102 | 6-(4-(4-fluorobenzoyl)piperazine-1-carbonyl)-3-(2-fluorobenzyl)-5-methylthieno[2,3-d]pyrimidin-4(3H)-one | 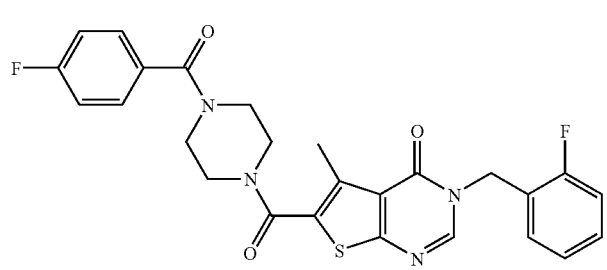 | 509.1 |

TABLE 1-continued

| Cmpd No. | Name | Structure | Mass Spec (m/z) |
|---|---|---|---|
| 103 | 3-(2-fluorobenzyl)-5-methyl-6-(4-(3,4,5-trimethoxybenzoyl)piperazine-1-carbonyl)thieno[2,3-d]pyrimidin-4(3H)-one | 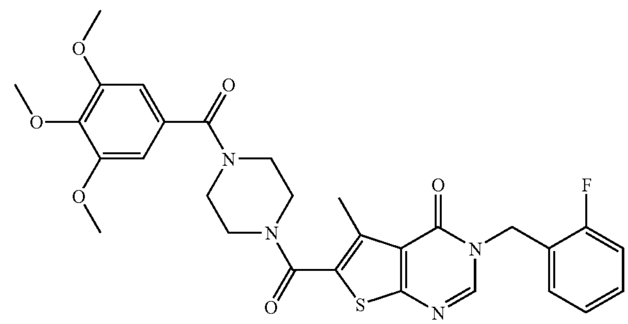 | 581.9 |
| 104 | N-(4-chlorobenzyl)-3-(2-fluorobenzyl)-4-oxo-3,4-dihydroquinazoline-7-carboxamide | 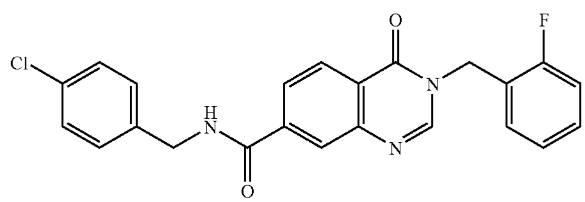 | 422.4 |
| 105 | N-benzyl-3-(2-fluorobenzyl)-4-oxo-3,4-dihydroquinazoline-7-carboxamide | 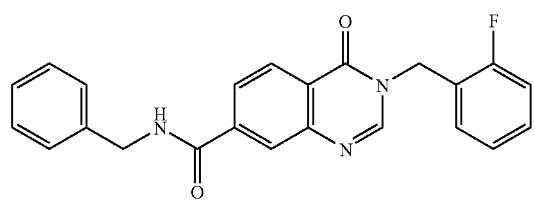 | 388.1 |
| 106 | 3-(2-(4-methylpiperidin-1-yl)-2-oxoethyl)-7-(4-morpholinopiperidine-1-carbonyl)quinazolin-4(3H)-one | 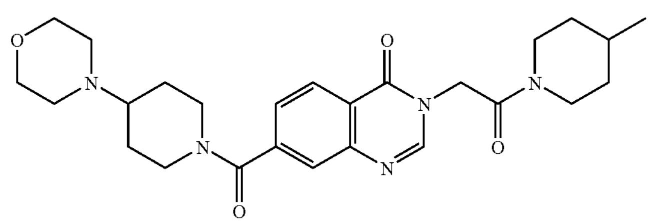 | 482.3 |
| 107 | 3-(2-fluorobenzyl)-7-(4-(2-fluorophenyl)piperazine-1-carbonyl)quinazolin-4(3H)-one | 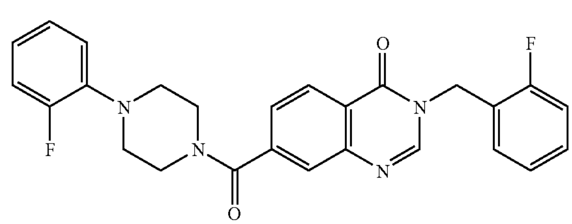 | 461.4 |
| 108 | 7-(3,5-dimethylpiperazine-1-carbonyl)-3-(2-(4-methylpiperidin-1-yl)-2-oxoethyl)quinazolin-4(3H)-one | 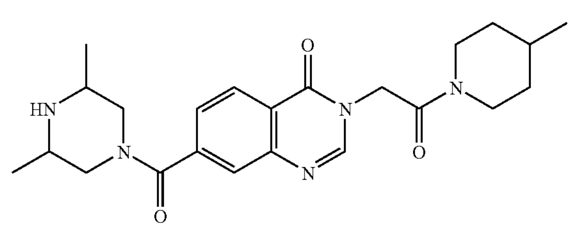 | 426.2 |

TABLE 1-continued

| Cmpd No. | Name | Mass Spec (m/z) |
|---|---|---|
| 109 | 3-(2-(4-methylpiperidin-1-yl)-2-oxoethyl)-7-(4-morpholinopiperidine-1-carbonyl)quinazolin-4(3H)-one | 482.3 |
| 110 | 7-(4-(3-chlorophenyl)piperazine-1-carbonyl)-3-(2-(4-fluoropiperidin-1-yl)-2-oxoethyl)quinazolin-4(3H)-one | 512.4 |
| 111 | 7-(4-(3-chlorophenyl)piperazine-1-carbonyl)-3-(2-oxo-2-(pyrrolidin-1-yl)ethyl)quinazolin-4(3H)-one | 480.4 |
| 112 | 2-(7-(4-(3-chlorophenyl)piperazine-1-carbonyl)-4-oxoquinazolin-3(4H)-yl)-N,N-diethylacetamide | 482.4 |
| 113 | N,N-diethyl-2-(7-(4-(2-fluorophenyl)piperazine-1-carbonyl)-4-oxoquinazolin-3(4H)-yl)acetamide | 466.3 |
| 114 | 2-(7-(4-(3-chlorophenyl)piperazine-1-carbonyl)-4-oxoquinazolin-3(4H)-yl)-N-cyclohexylacetamide | 508.2 |
| 115 | 6-(4-(3-chlorophenyl)piperazine-1-carbonyl)-3-(2-oxo-2-(pyrrolidin-1-yl)ethyl)quinazolin-4(3H)-one | 480.4 |

TABLE 1-continued

| Cmpd No. | Name | Structure | Mass Spec (m/z) |
|---|---|---|---|
| 116 | 2-(6-(4-(3-chlorophenyl)piperazine-1-carbonyl)-4-oxoquinazolin-3(4H)-yl)-N-cyclohexylacetamide | 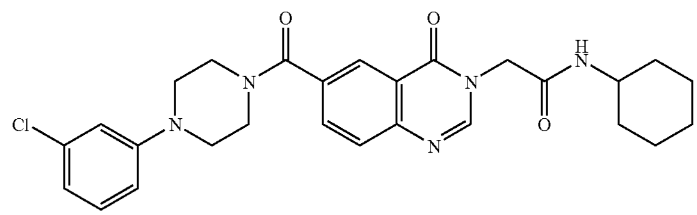 | 508.1 |
| 117 | 2-(6-(4-(3-chlorophenyl)piperazine-1-carbonyl)-4-oxoquinazolin-3(4H)-yl)-N-(pentan-3-yl)acetamide | 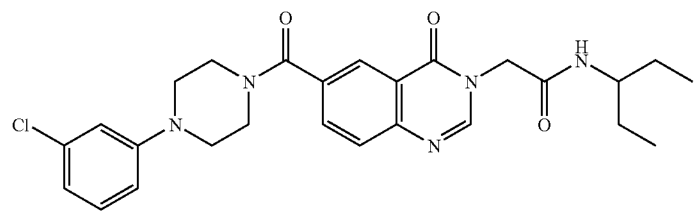 | 482.2 |
| 118 | 6-(4-(3-chlorophenyl)piperazine-1-carbonyl)-3-(2-(4-fluoropiperidin-1-yl)-2-oxoethyl)quinazolin-4(3H)-one | 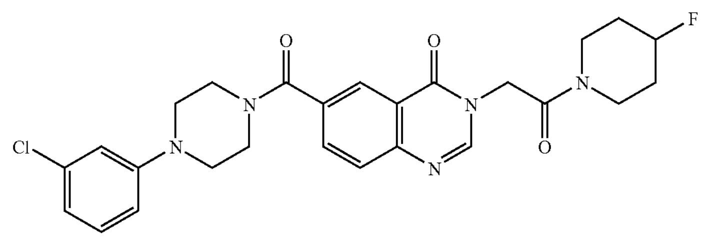 | 512.3 |
| 119 | 3-(2-(4-(3-chlorophenyl)piperazine-1-yl)-2-oxoethyl)-5-methyl-6-(pyrrolidine-1-carbonyl)thieno[2,3-d]pyrimidin-4(3H)-one | 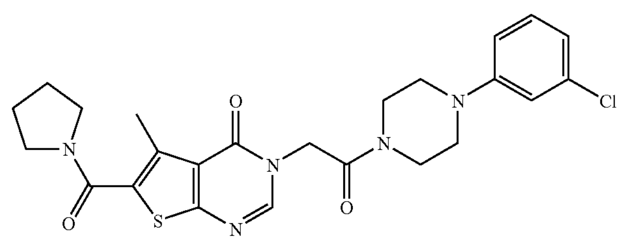 | 500.0 |
| 120 | (S)-3-(2-(4-(3-chlorophenyl)piperazine-1-yl)-2-oxoethyl)-5-methyl-6-(3-fluoro pyrrolidine-1-carbonyl)thieno[2,3-d]pyrimidin-4(3H)-one | 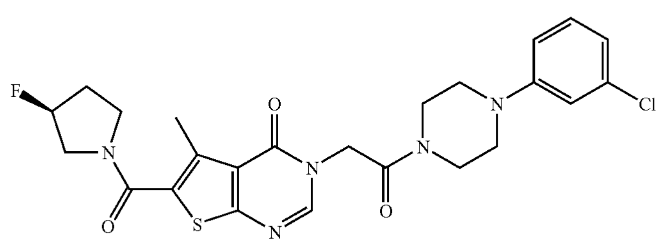 | 518.4 |
| 121 | 3-(2-(4-(3-chlorophenyl)piperazine-1-yl)-2-oxoethyl)-6-(3,3-difluoro pyrrolidine-1-carbonyl)-5-methylthieno[2,3-d]pyrimidin-4(3H)-one | 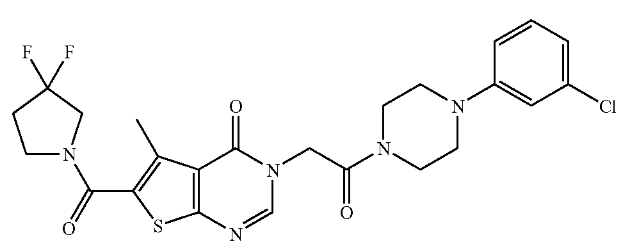 | 536.3 |

TABLE 1-continued

| Cmpd No. | Name | Structure | Mass Spec (m/z) |
|---|---|---|---|
| 122 | 3-(2-(4-(3-chlorophenyl)piperazine-1-yl)-2-oxoethyl)-6-(3,3-difluoro piperidine-1-carbonyl)-5-methylthieno[2,3-d]pyrimidin-4(3H)-one | 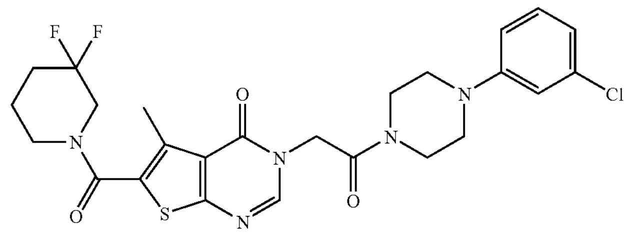 | 550.2 |
| 123 | 6-(4,4-difluoropiperidine-1-carbonyl)-3-(2-(4-(2-fluorophenyl)piperazin-1-yl)-2-oxoethyl)-5-methylthieno[2,3-d]pyrimidin-4(3H)-one | 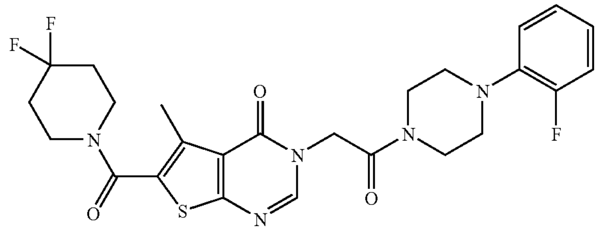 | 534.5 |
| 124 | N-ethyl-2-(6-(4-(2-fluorophenyl)piperazine-1-carbonyl)-5-methyl-4-oxothieno[2,3-d]pyrimidin-3(4H)-yl)-N-(2,2,2-trifluroethyl)acetamide | 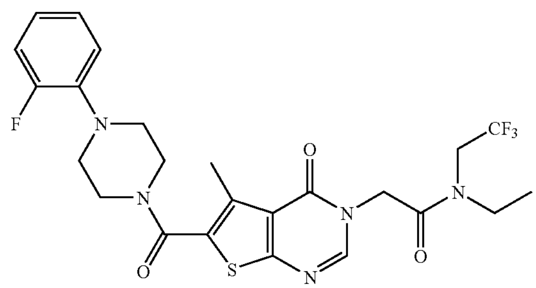 | 540.1 |
| 125 | N-ethyl-2-(6-(4-(phenyl piperazine-1-carbonyl)-5-methyl-4-oxothieno[2,3-d]pyrimidin-3(4H)-yl)-N-(2,2,2-trifluoroethyl)acetamide | 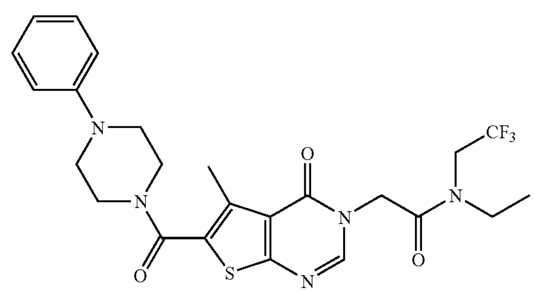 | 522.3 |
| 126 | N-ethyl-2-(6-(4-(3-chlorophenyl)piperazine-1-carbonyl)-5-methyl-4-oxothieno[2,3-d]pyrimidin-3(4H)-yl)-N-(2,2,2-trifluoroethyl)acetamide | 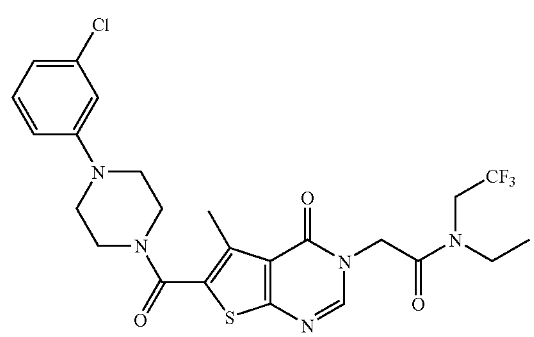 | 556.2 |

TABLE 1-continued

| Cmpd No. | Name | Structure | Mass Spec (m/z) |
|---|---|---|---|
| 127 | 2-(6-(4-(3-chlorophenyl)piperazine-1-carbonyl)-5-methyl-4-oxothieno[2,3-d]pyrimidin-3(4H)-yl)-N-ethyl-N-(2,2,2-trifluoroethyl)acetamide | 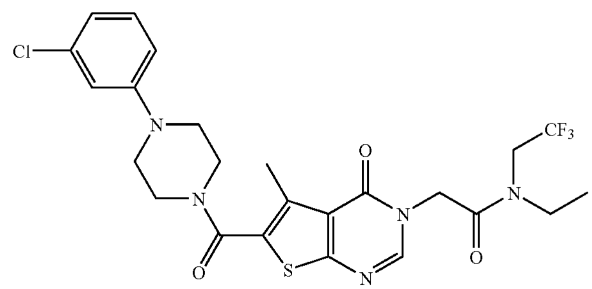 | 556.2 |
| 128 | N-ethyl-2-(6-(4-(2-fluoro-phenyl)piperazine-1-carbonyl)-5-methyl-4-oxothieno[2,3-d]pyrimidin-3(4H)-yl)-N-(2,2,2-trifluoroethyl)acetamide | 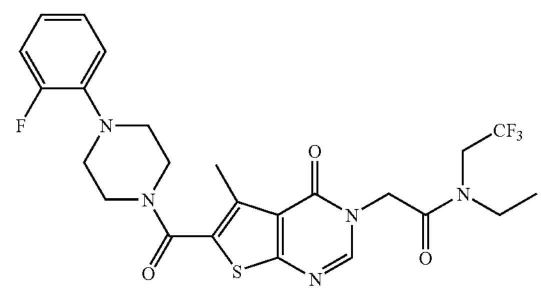 | 540.1 |
| 129 | N-ethyl-2-(5-methyl-4-oxo-6-(4-phenylpiperazine-1-carbonyl)thieno[2,3-d]pyrimidin-3(4H)-yl)-N-(2,2,2-trifluoroethyl)acetamide | 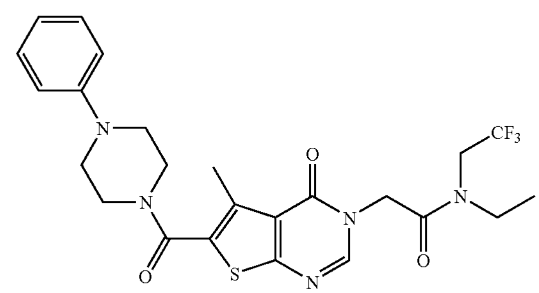 | 522.3 |
| 130 | N-ethyl-2-(5-methyl-4-oxo-6-(4-(4-(trifluromethyl)phenyl)piperazine-1-carbonyl)thieno[2,3-d]pyrimidin-3(4H)-yl)-N-(2,2,2-trifluoroethyl)acetamide | 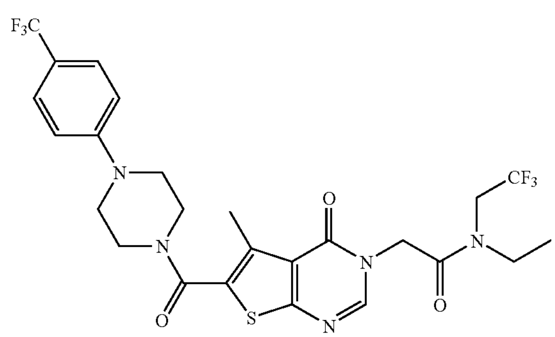 | 590.3 |
| 131 | N-tert-butyl-2-(6-(4-(3-chloro-4-fluorophenyl)piperazine-1-carbonyl)-5-methyl-4-oxo-thieno[2,3-d]pyrimidin-3(4H)-yl)acetamide | 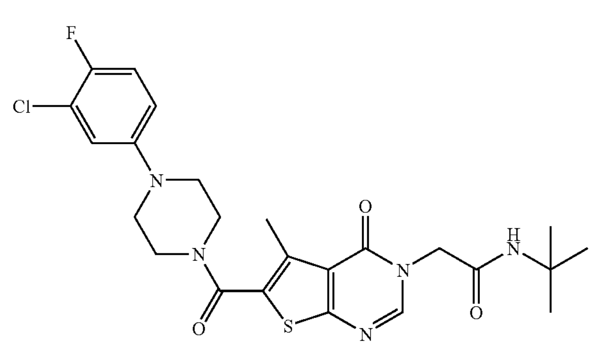 | 520.3 |

TABLE 1-continued

| Cmpd No. | Name | Structure | Mass Spec (m/z) |
|---|---|---|---|
| 132 | N-tert-butyl-2-(6-(4-(3,4-dichlorophenyl)piperazine-1-carbonyl)-5-methyl-4-oxo-thieno[2,3-d]pyrimidin-3(4H)-yl)acetamide | 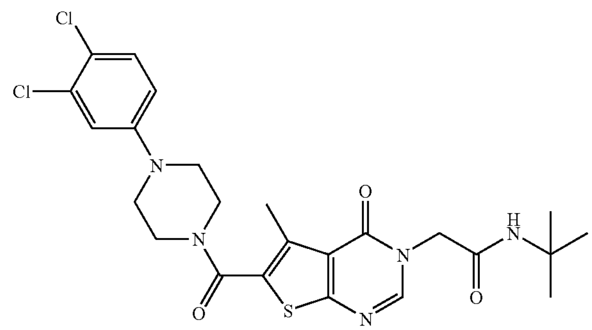 | 536.9 |
| 133 | 2-(6-(4-(3-chloro-4-fluoro-phenyl)piperazine-1-carbonyl)-5-methyl-4-oxothieno[2,3-d]pyrimidin-3(4H)-yl)-N-cyclohexylacetamide | 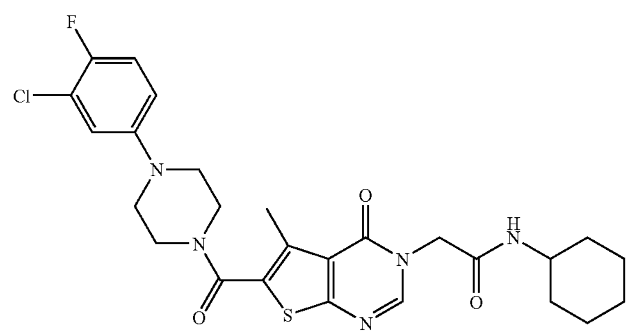 | 546.1 |
| 134 | 6-(4-(3-chloro-4-fluoro-phenyl)piperazine-1-carbonyl)-5-methyl-3-(2-oxo-2-(pyrrolidin-1-yl)ethyl)thieno[2,3-d]pyrimidin-4(3H)-one | 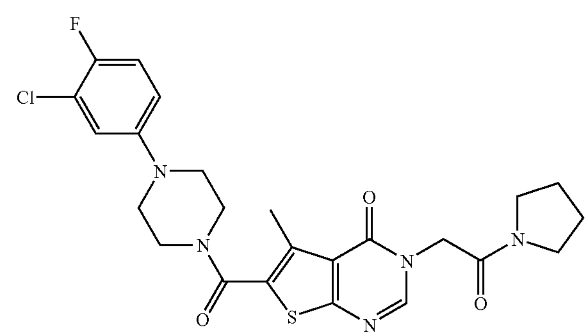 | 518.1 |
| 135 | 6-(4-(3,4-dichlorophenyl)piperazine-1-carbonyl)-5-methyl-3-(2-oxo-2-(pyrrolidin-1-yl)ethyl)thieno[2,3-d]pyrimidin-4(3H)-one | 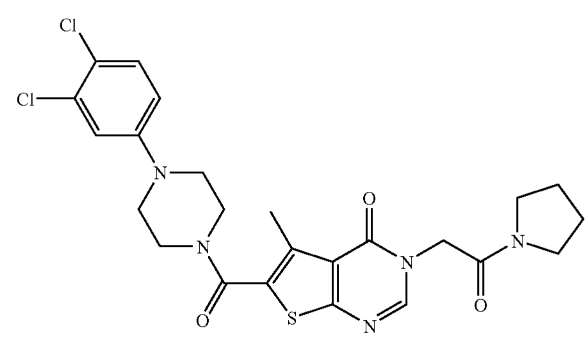 | 534.0 |

TABLE 1-continued

| Cmpd No. | Name | Structure | Mass Spec (m/z) |
|---|---|---|---|
| 136 | 6-(4-(3-chloro-phenyl)piperazine-1-carbonyl)-5-methyl-3-(2-oxo-2-(pyrrolidin-1-yl)ethyl)thieno[2,3-d]pyrimidin-4(3H)-one | 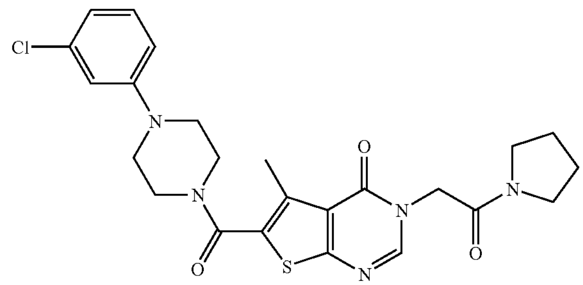 | 499.1 |
| 137 | (S)-6-(4-(3-chloro-4-fluoro-phenyl)piperazine-1-carbonyl)-3-(2-(3-fluoro-pyrrolidin-1-yl)-2-oxoethyl)-5-methyl-thieno[2,3-d]pyrimidin-4(3H)-one | 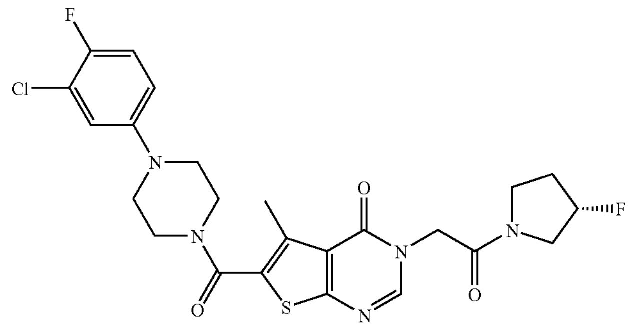 | 536.2 |
| 138 | 6-(4-(3,5-dichlorophenyl)piperazine-1-carbonyl)-5-methyl-3-(2-oxo-2-(pyrrolidin-1-yl)ethyl)thieno[2,3-d]pyrimidin-4(3H)-one | 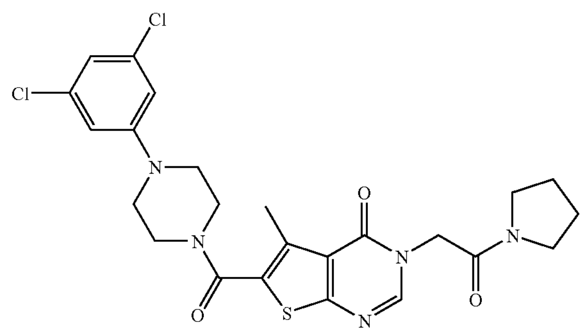 | 534.1 |
| 139 | N-(2,4-difluorophenyl)-2-(6-(4-(2-fluorophenyl)piperazine-1-carbonyl)-5-methyl-4-oxo-thieno[2,3-d]pyrimidin-3(4H)-yl)acetamide | 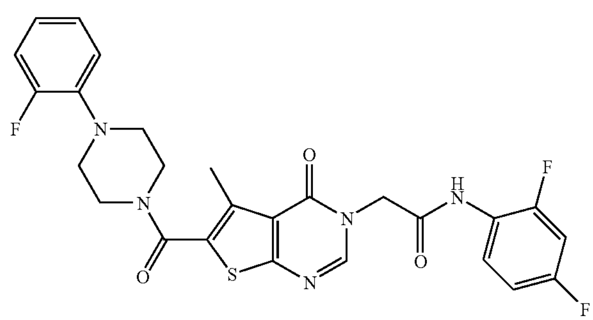 | 542.6 |
| 140 | 2-(6-(4-(3-chlorophenyl)piperazine-1-carbonyl)-5-methyl-4-oxothieno[2,3-d]pyrimidin-3(4H)-yl)-N-(2,4 difluoro phenyl)acetamide | 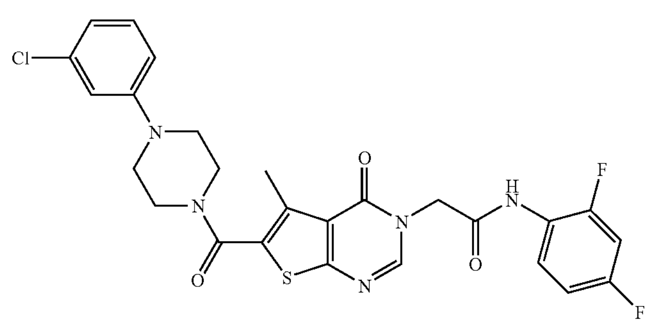 | 558.0 |

TABLE 1-continued

| Cmpd No. | Name | Structure | Mass Spec (m/z) |
|---|---|---|---|
| 141 | (S)-N-(3,5-difluorophenyl)-2-(6-(3-fluoropyrrolidine-1-carbonyl)-5-methyl-4-oxothieno[2,3-d]pyrimidin-3(4H)-yl)acetamide | 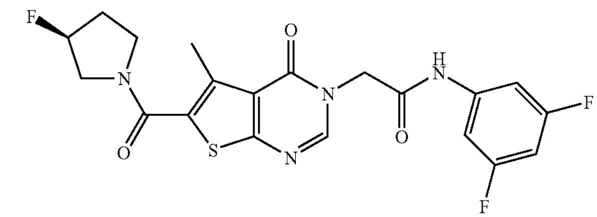 | 451.5 |
| 142 | 2-(6-(4-(2-fluorophenyl)piperazine-1-carbonyl)-5-methyl-4-oxothieno[2,3-d]pyrimidin-3(4H)-yl)-N-(4-(trifluoromethyl)phenyl)acetamide | 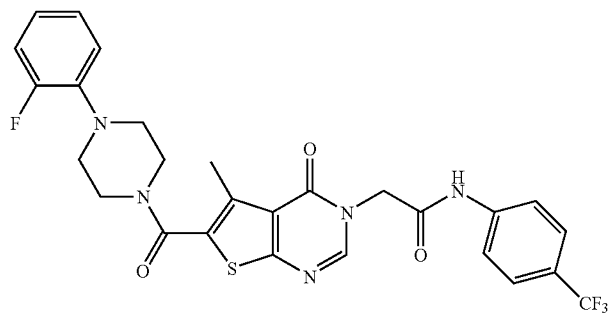 | 574.2 |

Example 14

T-Type Channel Blocking Activities of Various Invention Compounds

A. Transformation of HEK Cells:

T-type calcium channel blocking activity was assayed in human embryonic kidney cells, HEK 293, stably transfected with the T-type calcium channel subunits. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells stably transfected using a standard calcium phosphate protocol and the appropriate calcium channel cDNA's. Fresh DMEM was supplied and the cells transferred to 28° C./5% $CO_2$. Cells were incubated for 1 to 2 days prior to whole cell recording.

Standard patch-clamp techniques were employed to identify blockers of T-type currents. Briefly, previously described HEK cell lines stably expressing human $\alpha_{1G}$, $\alpha_{1H}$ and $\alpha_{1I}$ T-type channels were used for all the recordings (passage #: 4-20, 37° C., 5% $CO_2$). Whole cell patch clamp experiments were performed using an Axopatch 200B amplifier (Axon Instruments, Burlingame, Calif.) linked to a personal computer equipped with pCLAMP software. Data were analyzed using Clampfit (Axon Instruments) and SigmaPlot 4.0 (Jandel Scientific). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal solution).

TABLE 2

External Solution 500 ml - pH 7.4, 265.5 mOsm

| Salt | Final mM | Stock M | Final ml |
|---|---|---|---|
| CsCl | 142 | 1 | 71 |
| $CaCl_2$ | 2 | 1 | 1 |
| $MgCl_2$ | 1 | 1 | 0.5 |
| HEPES | 10 | 0.5 | 10 |
| glucose | 10 | — | 0.9 grams |

TABLE 3

Internal Solution 50 ml - pH 7.3 with CsOH, 270 mOsm

| Salt | Final mM | Stock M | Final ml |
|---|---|---|---|
| Cs-Methanesulfonate | 126.5 | — | 1.442 gr/50 ml |
| MgCl2 | 2 | 1 | 0.1 |
| HEPES | 10 | 0.5 | 1 |
| EGTA-Cs | 11 | 0.25 | 2.2 |
| ATP | 2 | 0.2 | 0.025 (1 aliquot/2.5 ml) |

T-type currents were reliably obtained by using two voltage protocols: (1) "non-inactivating", and (2) "inactivation"

In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about 15% of the T-type channels.

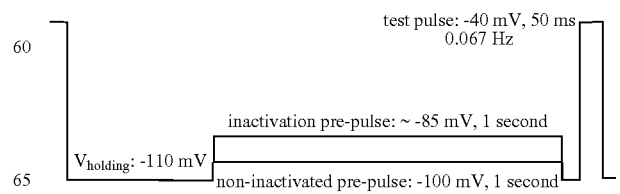

Test compounds were dissolved in external solution, 0.1-0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. $K_d$ values are shown for various compounds of the invention in Table 4 measured at 1 μM for the drug of interest except for compound 18 which was measured at 200 nM.

TABLE 4

| T-type Calcium Channel Block | | | |
|---|---|---|---|
| Compound | $\alpha_{1G}$ (μM) | $\alpha_{1H}$ (μM) | $\alpha_{1I}$ (μM) |
| 1 | 2.44 | 0.89 | |
| 4 | 4.12 | | |
| 5 | 1.23 | 0.62 | |
| 6 | 0.95 | 0.34 | 9.67 |
| 7 | | 1.14 | |
| 8 | 0.45 | 0.54 | |
| 9 | 3.73 | | |
| 10 | 1.22 | 0.30 | >31.30 |
| 12 | 1.96 | 1.06 | |
| 13 | | 2.14 | |
| 15 | 2.37 | 0.87 | |
| 16 | 1.37 | 0.63 | |
| 17 | 0.51 | 0.50 | |
| 19 | 3.60 | 0.36 | 2.38 |
| 20 | 0.33 | 0.18 | 2.10 |
| 21 | 0.61 | 0.19 | 5.20 |
| 22 | 1.36 | 0.43 | |
| 23 | 1.26 | 0.28 | 3.27 |
| 24 | 0.30 | 0.09 | 1.52 |
| 29 | | 0.95 | |
| 33 | 16.50 | 0.35 | 5.13 |
| 34 | | 0.44 | |
| 36 | 1.72 | 0.75 | |
| 37 | 0.30 | 0.17 | 3.29 |
| 38 | 0.10 | 0.10 | 2.14 |
| 41 | | 0.83 | |
| 42 | 0.57 | 0.28 | 3.84 |
| 46 | | 0.52 | |
| 47 | | 0.56 | |
| 51 | | 0.57 | |
| 52 | 1.01 | 0.35 | 8.79 |
| 53 | 0.19 | 1.04 | 0.58 |
| 55 | 0.24 | 0.38 | >0.95 |
| 62 | 0.29 | 0.80 | 0.34 |
| 63 | 1.84 | | |
| 64 | 0.20 | 0.70 | 0.08 |
| 66 | 0.35 | 7.59 | 1.04 |
| 67 | 2.80 | | |
| 68 | 0.40 | | |
| 69 | 0.23 | 2.73 | 0.71 |
| 70 | 5.31 | | |
| 71 | >74.30 | | |
| 73 | 1.46 | 0.22 | 8.80 |
| 78 | 0.62 | 0.40 | |
| 79 | | 4.64 | |
| 81 | 1.68 | 0.72 | |
| 89 | 0.63 | 0.42 | |
| 90 | | 2.44 | |
| 91 | | 6.31 | |
| 93 | 2.70 | | |
| 94 | 20.30 | | |
| 95 | 2.66 | | |
| 115 | 4.28 | | |
| 127 | 1.15 | 0.63 | |
| 128 | 3.60 | | |
| 130 | 3.47 | 0.39 | |
| 134 | 0.51 | 18.20 | |
| 135 | 9.90 | 0.33 | 1.38 |
| 136 | 1.56 | | |
| 137 | 1.80 | >8.44 | |

TABLE 4-continued

| T-type Calcium Channel Block | | | |
|---|---|---|---|
| Compound | $\alpha_{1G}$ (μM) | $\alpha_{1H}$ (μM) | $\alpha_{1I}$ (μM) |
| 140 | 0.36 | 0.18 | 4.99 |
| 142 | 1.16 | 0.70 | |

The invention claimed is:

1. A pharmaceutical composition comprising a compound of the formula:

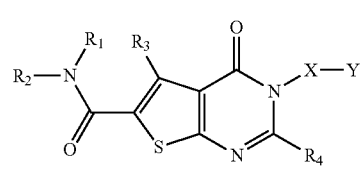

(1)

or a pharmaceutically acceptable salt or conjugate thereof in admixture with a pharmaceutically acceptable excipient, wherein each $R_1$ and $R_2$ is, independently, H, or an optionally substituted $C_{1-6}$ alkyl, $C_{2-6}$ alkenyl, $C_{2-6}$ alkynyl, $C_{2-6}$ heteroalkyl, $C_{2-6}$ heteroalkenyl, $C_{2-6}$ heteroalkynyl, $C_{6-10}$ aryl, $C_{5-12}$ heteroaryl, or $C_{6-12}$ aryl-$C_{1-6}$ alkyl; or $R_1$ and $R_2$ together form an optionally substituted 3-8 membered heterocyclic ring or 5-12 membered heteroaromatic ring;

each $R_3$ and $R_4$ is, independently, H, halo or an optionally substituted $C_{1-3}$ alkyl or $C_{1-3}$ heteroalkyl;

X is an optionally substituted $C_{1-3}$ alkylene or $C_{1-3}$ heteroalkylene;

Y is Ar or $N(R_5)(R_6)$, wherein Ar is an optionally substituted $C_{6-10}$ aryl or $C_{5-12}$ heteroaryl and $R_5$ and $R_6$ are independently, H, or an optionally substituted $C_{1-6}$ alkyl, $C_{2-6}$ alkenyl, $C_{2-6}$ alkynyl, $C_{2-6}$ heteroalkyl, $C_{2-6}$ heteroalkenyl, $C_{2-6}$ heteroalkynyl, $C_{6-10}$ aryl, $C_{5-12}$ heteroaryl, or $C_{6-12}$ aryl-$C_{1-6}$ alkyl; or $R_5$ and $R_6$ together form an optionally substituted 3-8 membered heterocyclic ring or 5-12 membered heteroaromatic ring;

wherein the optional substituents on each X, Ar, $R_1$, $R_2$, $R_3$, $R_4$ and $R_5$ is, independently, selected from the group consisting of halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from the group consisting of $C_{1-6}$ alkyl, $C_{2-6}$ alkenyl, $C_{2-6}$ alkynyl, $C_{2-6}$ heteroalkyl, $C_{2-6}$ heteroalkenyl, and $C_{2-6}$ heteroalkynyl; or the optional substituents may be one or more optionally substituted groups selected from the group consisting of $C_{1-6}$ alkyl, $C_{2-6}$ alkenyl, $C_{2-6}$ alkynyl, $C_{2-6}$ heteroalkyl, $C_{2-6}$ heteroalkenyl, and $C_{2-6}$ heteroalkynyl; and wherein the optional substituent on X, $R_1$, $R_2$, $R_5$ and $R_6$ may further be selected from =O or =NOR';

and wherein optional substituents on a heterocyclic ring formed with $R_1$ and $R_2$ or $R_5$ and $R_6$ may independently be selected from the group consisting of =O, =NOR', halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from the group consisting of $C_{1-6}$ alkyl, $C_{2-6}$ alkenyl, $C_{2-6}$ alkynyl, $C_{2-6}$ heteroalkyl, $C_{2-6}$ heteroalkenyl, and $C_{2-6}$ heteroalkynyl; or the optional substituents may be one or more optionally substituted groups selected from the group consisting of $C_{1-6}$ alkyl, $C_{2-6}$ alkenyl, $C_{2-6}$ alkynyl, $C_{2-6}$ heteroalkyl, $C_{2-6}$ heteroalkenyl, and $C_{2-6}$ heteroalkynyl, $C_{6-10}$ aryl, $C_{5-12}$ heteroaryl, and $C_{6-12}$ aryl-$C_{1-6}$ alkyl;

with the following two provisos that for compounds of formula (I): when Y is $N(R_5)(R_6)$, a carbon atom in X or Y that is adjacent to the N in Y is substituted by =O; and when Y is Ar, then neither $R_1$ nor $R_2$ are arylalkyl.

2. The pharmaceutical composition of claim 1, wherein X is an optionally substituted ethylene or an optionally substituted methylene.

3. The pharmaceutical composition of claim 2, wherein X is $CH_2C=O$, $CH_2CH_2$, $CH(CH_3)C=O$ or $CH_2$.

4. The pharmaceutical composition of claim 1, wherein Y is an optionally substituted phenyl.

5. The pharmaceutical composition of claim 4, wherein Y is phenyl, 2-fluorophenyl, 3-fluorophenyl or 4-fluorophenyl.

6. The pharmaceutical composition of claim 1, wherein Y is $N(R_5)(R_6)$.

7. The pharmaceutical composition of claim 6, wherein $R_5$ and $R_6$ are independently H, or an optionally substituted $C_{1-6}$ alkyl, $C_{1-6}$ heteroalkyl or $C_{6-10}$ aryl.

8. The pharmaceutical composition of claim 7, wherein $R_5$ and $R_6$ are independently H, or an optionally substituted methyl, ethyl, butyl, cyclohexyl, cyclopentyl, cyclopropyl or phenyl.

9. The pharmaceutical composition of claim 6, wherein $R_5$ and $R_6$ together with N to which they are attached form an optionally substituted 3-8 membered heterocyclic or 5-12 membered heteroaromatic ring.

10. The pharmaceutical composition of claim 9, wherein $R_5$ and $R_6$ together with N to which they are attached form a 5-6 membered heterocyclic ring.

11. The pharmaceutical composition of claim 1, wherein $R_1$ and $R_2$ together with N to which they are attached form an optionally substituted 3-8 membered heterocyclic or 5-12 membered heteroaromatic ring.

12. The pharmaceutical composition of claim 11, wherein $R_1$ and $R_2$ together with N to which they are attached form an optionally substituted pyrrolidinyl, piperidinyl, piperazinyl, morpholino, pyridinyl or pyrrolyl.

13. The pharmaceutical composition of claim 1, wherein $R_1$ and $R_2$ are independently H or an optionally substituted $C_{1-6}$ alkyl, $C_{1-6}$ heteroalkyl, $C_{5-12}$ heteroaryl or $C_{6-12}$ aryl-$C_{1-6}$ alkyl.

14. The pharmaceutical composition of claim 13, wherein $R_1$ and $R_2$ are independently H, methyl, butyl, phenyl or benzyl.

15. The pharmaceutical composition of claim 1, wherein $R_4$ is H.

16. The pharmaceutical composition of claim 1, wherein $R_3$ is H or methyl.

17. The pharmaceutical composition of claim 16, wherein the compound is of formula 1 and $R_3$ is methyl.

18. The pharmaceutical composition of claim 16, wherein the compound is of formula 2 and $R_3$ is H.

19. The pharmaceutical composition of claim 1, wherein the compound is:

2-(6-(4-(3-chlorophenyl)piperazine-1-carbonyl)-5-methyl-4-oxothieno[2,3-d]pyrimidin-3(4H)-yl)-N,N-diethylacetamide;

N,N-diethyl-2-(6-(4-(2-fluorophenyl)piperazine-1-carbonyl)-5-methyl-4-oxothieno[2,3-d]pyrimidin-3(4H)-yl) acetamide;

N,N-diethyl-2-(5-methyl-4-oxo-6-(4-phenylpiperazine-1-carbonyl)thieno[2,3-d]pyrimidin-3(4H)-yl)acetamide;

2-(6-(4-(2-chlorophenyl)piperazine-1-carbonyl)-5-methyl-4-oxothieno[2,3-d]pyrimidin-3(4H)-yl)-N,N-diethylacetamide;

2-(6-(4-(4-chlorophenyl)piperazine-1-carbonyl)-5-methyl-4-oxothieno[2,3-d]pyrimidin-3(4H)-yl)-N,N-diethylacetamide;

2-(6-(4-(3,4-dichlorophenyl)piperazine-1-carbonyl)-5-methyl-4-oxothieno[2,3-d]pyrimidin-3(4H)-yl)-N,N-diethylacetamide;

N,N-diethyl-2-(6-(4-(3-fluorophenyl)piperazine-1-carbonyl)-5-methyl-4-oxothieno[2,3-d]pyrimidin-3(4H)-yl) acetamide;

2-(6-(4-(4-chloro-3-(trifluoromethyl)phenyl)piperazine-1-carbonyl)-5-methyl-4-oxothieno[2,3-d]pyrimidin-3 (4H)-yl)-N,N-diethylacetamide;

N,N-diethyl-2-(5-methyl-4-oxo-6-(4-(2-(trifluoromethyl) phenyl)piperazine-1-carbonyl)thieno[2,3-d]pyrimidin-3(4H)-yl)acetamide;

N,N-diethyl-2-(5-methyl-4-oxo-6-(4-(4-(trifluoromethyl) phenyl)piperazine-1-carbonyl)thieno[2,3-d]pyrimidin-3(4H)-yl)acetamide;

N-tert-butyl-2-(6-(4-(4-fluorophenyl)piperazine-1-carbonyl)-5-methyl-4-oxothieno[2,3-d]pyrimidin-3(4H)-yl) acetamide;

N-tert-butyl-2-(5-methyl-4-oxo-6-(4-(3-(trifluoromethyl) phenyl)piperazine-1-carbonyl)thieno[2,3-d]pyrimidin-3(4H)-yl)acetamide;

N-tert-butyl-2-(5-methyl-4-oxo-6-(4-phenylpiperazine-1-carbonyl)thieno[2,3-d]pyrimidin-3(4H)-yl)acetamide;

N-tert-butyl-2-(6-(4-(2-fluorophenyl)piperazine-1-carbonyl)-5-methyl-4-oxothieno[2,3-d]pyrimidin-3(4H)-yl) acetamide;

N-tert-butyl-2-(6-(4-(4-chlorophenyl)piperazine-1-carbonyl)-5-methyl-4-oxothieno[2,3-d]pyrimidin-3(4H)-yl) acetamide;

N-tert-butyl-2-(6-(4-(3-chlorophenyl)piperazine-1-carbonyl)-5-methyl-4-oxothieno[2,3-d]pyrimidin-3(4H)-yl) acetamide;

2-(6-(4-(3,5-bis(trifluoromethyl)phenyl)piperazine-1-carbonyl)-5-methyl-4-oxothieno[2,3-d]pyrimidin-3(4H)-yl)-N-tert-butylacetamide;

N-cyclohexyl-2-(5-methyl-4-oxo-6-(4-tertbutylpiperazine-1-carbonyl)thieno[2,3-d]pyrimidin-3(4H)-yl)acetamide;

N-cyclohexyl-2-(5-methyl-4-oxo-6-(4-phenylpiperazine-1-carbonyl)thieno[2,3-d]pyrimidin-3(4H)-yl)acetamide;

2-(6-(4-(4-chlorophenyl)piperazine-1-carbonyl)-5-methyl-4-oxothieno[2,3-d]pyrimidin-3(4H)-yl)-N-cyclohexylacetamide;

N-cyclohexyl-2-(6-(4-(3-fluorophenyl)piperazine-1-carbonyl)-5-methyl-4-oxothieno[2,3-d]pyrimidin-3(4H)-yl)acetamide;

N-cyclohexyl-2-(6-(4-(4-fluorophenyl)piperazine-1-carbonyl)-5-methyl-4-oxothieno[2,3-d]pyrimidin-3(4H)-yl)acetamide;

N-cyclohexyl-2-(6-(4-(2-fluorophenyl)piperazine-1-carbonyl)-5-methyl-4-oxothieno[2,3-d]pyrimidin-3(4H)-yl)acetamide;

2-(6-(4-(3-chlorophenyl)piperazine-1-carbonyl)-5-methyl-4-oxothieno[2,3-d]pyrimidin-3(4H)-yl)-N-cyclohexylacetamide;

N-cyclohexyl-2-(6-(4-(3,4-dichlorophenyl)piperazine-1-carbonyl)-5-methyl-4-oxothieno[2,3-d]pyrimidin-3 (4H)-yl)acetamide;

N-cyclohexyl-2-(5-methyl-4-oxo-6-(piperidine-1-carbonyl)thieno[2,3-d]pyrimidin-3(4H)-yl)acetamide;

N-cyclohexyl-2-(6-(4-(3-methoxyphenyl)piperazine-1-carbonyl)-5-methyl-4-oxothieno[2,3-d]pyrimidin-3(4H)-yl)acetamide;

N-cyclohexyl-2-(5-methyl-6-(4-(4-methoxy phenyl)piperazine-1-carbonyl)-4-oxothieno[2,3-d]pyrimidin-3(4H)-yl)acetamide;

N-cyclohexyl-2-(5-methyl-6-(4-(3-nitrophenyl)piperazine-1-carbonyl)-4-oxothieno[2,3-d]pyrimidin-3(4H)-yl)acetamide;

N-(4,4-difluorocyclohexyl)-2-(5-methyl-4-oxo-6-(4-(phenyl)piperazine-1-carbonyl)thieno[2,3-d]pyrimidin-3(4H)-yl)acetamide;

N-(4,4-difluorocyclohexyl)-2-(5-methyl-4-oxo-6-(4-(2-fluorophenyl)piperazine-1-carbonyl)thieno[2,3-d]pyrimidin-3(4H)-yl)acetamide;

N-(4,4-difluorocyclohexyl)-2-(5-methyl-4-oxo-6-(4-(3-chlorophenyl)piperazine-1-carbonyl)thieno[2,3-d]pyrimidin-3(4H)-yl)acetamide;

N-cyclohexyl-2-(5-methyl-4-oxo-6-(4-phenylpiperazine-1-carbonyl)thieno[2,3-d]pyrimidin-3(4H)-yl)propanamide;

N-cyclohexyl-2-(6-(4-(2-fluorophenyl)piperazine-1-carbonyl)-5-methyl-4-oxothieno[2,3-d]pyrimidin-3(4H)-yl)propanamide;

N-cyclohexyl-2-(6-(4-(3-chlorophenyl)piperazine-1-carbonyl)-5-methyl-4-oxothieno[2,3-d]pyrimidin-3(4H)-yl)propanamide;

N-cyclopentyl-2-(6-(4-(2-fluorophenyl)piperazine-1-carbonyl)-5-methyl-4-oxothieno[2,3-d]pyrimidin-3(4H)-yl)acetamide;

2-(6-(4-(3-chlorophenyl)piperazine-1-carbonyl)-5-methyl-4-oxothieno[2,3-d]pyrimidin-3(4H)-yl)-N-cyclopentylacetamide;

2-(6-(4-(4-chloro-3-(trifluoromethyl)phenyl)piperazine-1-carbonyl)-5-methyl-4-oxothieno[2,3-d]pyrimidin-3(4H)-yl)-N-cyclopentylacetamide;

N-cyclopentyl-2-(5-methyl-6-(4-methylpiperazine-1-carbonyl)-4-oxothieno[2,3-d]pyrimidin-3(4H)-yl)acetamide;

N-cyclopentyl-2-(5-methyl-6-(4-tertbutylpiperazine-1-carbonyl)-4-oxothieno[2,3-d]pyrimidin-3(4H)-yl)acetamide;

N-cyclopentyl-2-(5-methyl-4-oxo-6-(4-phenylpiperazine-1-carbonyl)thieno[2,3-d]pyrimidin-3(4H)-yl)acetamide;

2-(6-(4-(4-chlorophenyl)piperazine-1-carbonyl)-5-methyl-4-oxothieno[2,3-d]pyrimidin-3(4H)-yl)-N-cyclopentylacetamide;

N-cyclopentyl-2-(6-(4-(3-methoxyphenyl)piperazine-1-carbonyl)-5-methyl-4-oxothieno[2,3-d]pyrimidin-3(4H)-yl)acetamide;

N-cyclopentyl-2-(6-(4-(4-methoxyphenyl)piperazine-1-carbonyl)-5-methyl-4-oxothieno[2,3-d]pyrimidin-3(4H)-yl)acetamide;

N-cyclopentyl-2-(6-(4-(3-nitrophenyl)piperazine-1-carbonyl)-5-methyl-4-oxothieno[2,3-d]pyrimidin-3(4H)-yl)acetamide;

N-cyclopentyl-2-(5-methyl-4-oxo-6-(4-phenylpiperazine-1-carbonyl)thieno[2,3-d]pyrimidin-3(4H)-yl)propanamide;

N-cyclopentyl-2-(6-(4-(2-fluorophenyl)piperazine-1-carbonyl)-5-methyl-4-oxothieno[2,3-d]pyrimidin-3(4H)-yl)propanamide;

N-cyclopentyl-2-(6-(4-(4-fluorophenyl)piperazine-1-carbonyl)-5-methyl-4-oxothieno[2,3-d]pyrimidin-3(4H)-yl)propanamide;

N-cyclopropyl-2-(5-methyl-4-oxo-6-(4-phenylpiperazine-1-carbonyl)thieno[2,3-d]pyrimidin-3(4H)-yl)acetamide;

N-cyclopropyl-2-(6-(4-(2-fluorophenyl)piperazine-1-carbonyl)-5-methyl-4-oxothieno[2,3-d]pyrimidin-3(4H)-yl)acetamide;

2-(6-(4-(2-fluorophenyl)piperazine-1-carbonyl)-5-methyl-4-oxothieno[2,3-d]pyrimidin-3(4H)-yl)-N-phenylacetamide;

2-(5-methyl-4-oxo-6-(4-phenylpiperazine-1-carbonyl)thieno[2,3-d]pyrimidin-3(4H)-yl)-N-phenylacetamide;

2-(6-(4-(3,5-bis(trifluoromethyl)phenyl)piperazine-1-carbonyl)-5-methyl-4-oxothieno[2,3-d]pyrimidin-3(4H)-yl)-N-phenylacetamide;

2-(5-methyl-6-(4-methylpiperazine-1-carbonyl)-4-oxothieno[2,3-d]pyrimidin-3(4H)-yl)-N-phenylacetamide;

2-(6-(4-phenylpiperazine-1-carbonyl)-5-methyl-4-oxothieno[2,3-d]pyrimidin-3(4H)-yl)-N-(3,5-difluorophenyl)acetamide;

2-(6-(4-(3-chlorophenyl)piperazine-1-carbonyl)-5-methyl-4-oxothieno[2,3-d]pyrimidin-3(4H)-yl)-N-(3,5-difluorophenyl)acetamide;

(S)-N-(3,5-difluorophenyl)-2-(6-(3-fluoropyrrolidin-1-carbonyl)-5-methyl-4-oxothieno[2,3-d]pyrimidin-3(4H)-yl)acetamide;

(S)-N-(3,5-difluorophenyl)-2-(6-(3,3-difluoropyrrolidin-1-carbonyl)-5-methyl-4-oxothieno[2,3-d]pyrimidin-3(4H)-yl)acetamide;

N-(3,5-difluorophenyl)-2-(6-(4-fluoropiperidin-1-carbonyl)-5-methyl-4-oxothieno[2,3-d]pyrimidin-3(4H)-yl)acetamide;

N-(3,5-difluorophenyl)-2-(6-(4,4-difluoropiperidin-1-carbonyl)-5-methyl-4-oxothieno[2,3-d]pyrimidin-3(4H)-yl)acetamide;

N-(3,5-difluorophenyl)-2-(6-(3,3-difluoropiperidin-1-carbonyl)-5-methyl-4-oxothieno[2,3-d]pyrimidin-3(4H)-yl)acetamide;

2-(6-(4-(2-fluorophenyl)piperazine-1-carbonyl)-5-methyl-4-oxothieno[2,3-d]pyrimidin-3(4H)-yl)-N-(3-(trifluoromethyl)phenyl)acetamide;

2-(5-methyl-(4-oxo-6-(4-(trifluoromethyl)piperidin-1-carbonyl)thieno[2,3-d]pyrimidin-3(4H)-yl)-N-(3-(trifluoromethyl)phenyl)acetamide;

N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide;

N-(3,5-bis(trifluoromethyl)phenyl)-2-(5-methyl-4-oxo-6-(piperazine-1-carbonyl)thieno[2,3-d]pyrimidin-3(4H)-yl)acetamide;

3-(2-(3,5-bis(trifluoromethyl)phenylamino)-2-oxoethyl)-N,5-dimethyl-4-oxo-3,4-dihydrothieno[2,3-d]pyrimidine-6-carboxamide;

3-(2-(3,5-bis(trifluoromethyl)phenylamino)-2-oxoethyl)-5-methyl-4-oxo-3,4-dihydrothieno[2,3-d]pyrimidine-6-carboxamide;

3-(2-(3,5-bis(trifluoromethyl)phenylamino)-2-oxoethyl)-N-tert-butyl-5-methyl-4-oxo-3,4-dihydrothieno[2,3-d]pyrimidine-6-carboxamide;

N-(3,5-bis(trifluoromethyl)phenyl)-2-(5-methyl-4-oxo-6-(piperidine-1-carbonyl)thieno[2,3-d]pyrimidin-3(4H)-yl)acetamide;

N-(3,5-bis(trifluoromethyl)phenyl)-2-(5-methyl-4-oxo-6-(pyrrolidine-1-carbonyl)thieno[2,3-d]pyrimidin-3(4H)-yl)acetamide;

(S)-N-(3,5-bis(trifluoromethyl)phenyl)-2-(5-methyl-4-oxo-6-(3-fluoropyrrolidine-1-carbonyl)thieno[2,3-d]pyrimidin-3(4H)-yl)acetamide;

N-(3,5-bis(trifluoromethyl)phenyl)-2-(5-methyl-4-oxo-6-(4-fluoropiperidine-1-carbonyl)thieno[2,3-d]pyrimidin-3(4H)-yl)acetamide;

6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one;

5-methyl-3-(2-oxo-2-(pyrrolidin-1-yl)ethyl)-6-(4-phenylpiperazine-1-carbonyl)thieno[2,3-d]pyrimidin-4(3H)-one;

(R)-6-(4-(3-chlorophenyl)-piperazine-1-carbonyl)-3-(2-(3-fluoropyrrolidin-1-yl)-2-oxoethyl)-5-methylthieno[2,3-d]pyrimidin-4(3H)-one;

(S)-6-(4-(3-chlorophenyl)-piperazine-1-carbonyl)-3-(2-(3-fluoropyrrolidin-1-yl)-2-oxoethyl)-5-methylthieno[2,3-d]pyrimidin-4(3H)-one;

(S)-6-(4-(2-fluorophenyl)-piperazine-1-carbonyl)-3-(2-(3-fluoropyrrolidin-1-yl)-2-oxoethyl)-5-methylthieno[2,3-d]pyrimidin-4(3H)-one;

6-(4-(3-chlorophenyl)-piperazine-1-carbonyl)-3-(2-(3,3-difluoropyrrolidin-1-yl)-2-oxoethyl)-5-methylthieno[2,3-d]pyrimidin-4(3H)-one;

3-(2-(3,3-difluoropyrrolidin-1-yl)-2-oxoethyl)-6-(4-(2-fluorophenyl)piperazine-1-carbonyl)-5-methylthieno[2,3-d]pyrimidin-4(3H)-one;

6-(4-(3-chlororophenyl)piperazine-1-carbonyl)-5-methyl-3-(2-oxo-2-(2-trifluoromethyl)pyrrolidin-1-yl)ethyl)thieno[2,3-d]pyrimidin-4(3H)-one;

6-(4-(2-fluorophenyl)piperazine-1-carbonyl)-5-methyl-3-(2-oxo-2-(piperidin-1-yl)ethyl)thieno[2,3-d]pyrimidin-4(3H)-one;

6-(4-(3-chlorophenyl)piperazine-1-carbonyl)-5-methyl-3-(2-(3-methylpiperidin-1-yl)-2-oxoethyl)thieno[2,3-d]pyrimidin-4(3H)-one;

6-(4-(2-fluorophenyl)piperazine-1-carbonyl)-5-methyl-3-(2-(4-methylpiperidin-1-yl)-2-oxoethyl)thieno[2,3-d]pyrimidin-4(3H)-one;

4-(2-(4-fluoropiperidin-1-yl)-2-oxoethyl)-6-(4-(3-chlorophenyl)piperazine-1-carbonyl)-5-methylthieno[2,3-d]pyrimidin-4(3H)-one;

3-(2-(3,3-difluoropiperidin-1-yl)-2-oxoethyl)-6-(4-(2-fluorophenyl)piperazine-1-carbonyl)-5-methylthieno[2,3-d]pyrimidin-4(3H)-one;

3-(2-(3,3-difluoropiperidin-1-yl)-2-oxoethyl)-6-(4-(3-chlorophenyl)piperazine-1-carbonyl)-5-methylthieno[2,3-d]pyrimidin-4(3H)-one;

6-(4-(3-chlorophenyl)piperazine-1-carbonyl)-3-(2-(4,4-difluoropiperidin-1-yl)-2-oxoethyl)-5-methylthieno[2,3-d]pyrimidin-4(3H)-one;

3-(2-(4,4-difluoropiperidin-1-yl)-2-oxoethyl)-6-(4-(2-fluorophenyl)piperazine-1-carbonyl)-5-methylthieno[2,3-d]pyrimidin-4(3H)-one;

6-(4-(2-fluorophenyl)piperazine-1-carbonyl)-5-methyl-3-(2-oxo-2-((4-trifluoromethyl)piperidin-1-yl)ethyl)thieno[2,3-d]pyrimidin-4(3H)-one;

3-(2-(3,3-difluoropiperidin-1-yl)-2-oxoethyl)-6-(4-(4-fluorophenyl)piperazine-1-carbonyl)-5-methylthieno[2,3-d]pyrimidin-4(3H)-one;

(S)-6-(4-(4-fluorophenyl)-piperazine-1-carbonyl)-3-(2-(3-fluoropyrrolidin-1-yl)-2-oxoethyl)-5-methylthieno[2,3-d]pyrimidin-4(3H)-one;

5-methyl-3-(2-(2-oxopyrrolidin-1-yl)ethyl)-6-(4-phenylpiperazine-1-carbonyl)thieno[2,3-d]pyrimidin-4(3H)-one;

6-(4-(3,5-bis(trifluoromethyl)phenyl)piperazine-1-carbonyl)-5-methyl-3-(2-(2-oxopyrrolidin-1-yl)ethyl)thieno[2,3-d]pyrimidin-4(3H)-one;

6-(4-(4-chlorophenyl)piperazine-1-carbonyl)-5-methyl-3-(2-(2-oxopyrrolidin-1-yl)ethyl)thieno[2,3-d]pyrimidin-4(3H)-one;

6-(4-(2-fluorophenyl)piperazine-1-carbonyl)-5-methyl-3-(2-(2-oxopyrrolidin-1-yl)ethyl)thieno[2,3-d]pyrimidin-4(3H)-one;

2-(5-methyl-4-oxo-6-(4-phenylpiperazine-1-carbonyl)thieno[2,3-d]pyrimidin-3(4H)-yl)-N-(2,2,2-trifluoroethyl)acetamide;

3-benzyl-N,N,5-trimethyl-4-oxo-3,4-dihydrothieno[2,3-d]pyrimidine-6-carboxamide;

3-(2-fluorobenzyl)-N,N,5-trimethyl-4-oxo-3,4-dihydrothieno[2,3-d]pyrimidine-6-carboxamide;

6-(3,5-dimethylpiperazine-1-carbonyl)-3-(2-fluorobenzyl)-5-methylthieno[2,3-d]pyrimidin-4(3H)-one;

3-(2-fluorobenzyl)-5-methyl-6-(piperazine-1-carbonyl)thieno[2,3-d]pyrimidin-4(3H)-one;

6-(4-(3-chlorophenyl)piperazine-1-carbonyl)-3-(2-fluorobenzyl)-5-methyl thieno[2,3-d]pyrimidin-4(3H)-one;

6-(4-(4-fluorobenzoyl)piperazine-1-carbonyl)-3-(2-fluorobenzyl)-5-methylthieno[2,3-d]pyrimidin-4(3H)-one;

3-(2-fluorobenzyl)-5-methyl-6-(4-(3,4,5-trimethoxybenzoyl)piperazine-1-carbonyl)thieno[2,3-d]pyrimidin-4(3H)-one;

3-(2-(4-(3-chlorophenyl)piperazine-1-yl)-2-oxoethyl)-5-methyl-6-(pyrrolidine-1-carbonyl)thieno[2,3-d]pyrimidin-4(3H)-one;

(S)-3-(2-(4-(3-chlorophenyl)piperazine-1-yl)-2-oxoethyl)-5-methyl-6-(3-fluoro pyrrolidine-1-carbonyl)thieno[2,3-d]pyrimidin-4(3H)-one;

3-(2-(4-(3-chlorophenyl)piperazine-1-yl)-2-oxoethyl)-6-(3,3-difluoro pyrrolidine-1-carbonyl)-5-methylthieno[2,3-d]pyrimidin-4(3H)-one;

3-(2-(4-(3-chlorophenyl)piperazine-1-yl)-2-oxoethyl)-6-(3,3-difluoro piperidine-1-carbonyl)-5-methylthieno[2,3-d]pyrimidin-4(3H)-one;

6-(4,4-difluoropiperidine-1-carbonyl)-3-(2-(4-(2-fluorophenyl)piperazin-1-yl)-2-oxoethyl)-5-methylthieno[2,3-d]pyrimidin-4(3H)-one;

N-ethyl-2-(6-(4-(2-fluorophenyl)piperazine-1-carbonyl)-5-methyl-4-oxothieno[2,3-d]pyrimidin-3(4H)-yl)-N-(2,2,2-trifluoroethyl)acetamide;

N-ethyl-2-(6-(4-(phenyl piperazine-1-carbonyl)-5-methyl-4-oxothieno[2,3-d]pyrimidin-3(4H)-yl)-N-(2,2,2-trifluoroethyl)acetamide;

N-ethyl-2-(6-(4-(3-chlorophenyl)piperazine-1-carbonyl)-5-methyl-4-oxothieno[2,3-d]pyrimidin-3(4H)-yl)-N-(2,2,2-trifluoroethyl)acetamide;

2-(6-(4-(3-chlorophenyl)piperazine-1-carbonyl)-5-methyl-4-oxothieno[2,3-d]pyrimidin-3(4H)-yl)-N-ethyl-N-(2,2,2-trifluoroethyl)acetamide;

N-ethyl-2-(6-(4-(2-fluorophenyl)piperazine-1-carbonyl)-5-methyl-4-oxothieno[2,3-d]pyrimidin-3(4H)-yl)-N-(2,2,2-trifluoroethyl)acetamide;

N-ethyl-2-(5-methyl-4-oxo-6-(4-phenylpiperazine-1-carbonyl)thieno[2,3-d]pyrimidin-3(4H)-yl)-N-(2,2,2-trifluoroethyl)acetamide;

N-ethyl-2-(5-methyl-4-oxo-6-(4-(4-(trifluoromethyl)phenyl)piperazine-1-carbonyl)thieno[2,3-d]pyrimidin-3(4H)-yl)-N-(2,2,2-trifluoroethyl)acetamide;

N-tert-butyl-2-(6-(4-(3-chloro-4-fluorophenyl)piperazine-1-carbonyl)-5-methyl-4-oxothieno[2,3-d]pyrimidin-3(4H)-yl)acetamide;

N-tert-butyl-2-(6-(4-(3,4-dichlorophenyl)piperazine-1-carbonyl)-5-methyl-4-oxothieno[2,3-d]pyrimidin-3 (4H)-yl)acetamide;
2-(6-(4-(3-chloro-4-fluorophenyl)piperazine-1-carbonyl)-5-methyl-4-oxothieno[2,3-d]pyrimidin-3(4H)-yl)-N-cyclohexylacetamide;
6-(4-(3-chloro-4-fluorophenyl)piperazine-1-carbonyl)-5-methyl-3-(2-oxo-2-(pyrrolidin-1-yl)ethyl)thieno[2,3-d]pyrimidin-4(3H)-one;
6-(4-(3,4-dichlorophenyl)piperazine-1-carbonyl)-5-methyl-3-(2-oxo-2-(pyrrolidin-1-yl)ethyl)thieno[2,3-d]pyrimidin-4(3H)-one;
6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one;
(S)-6-(4-(3-chloro-4-fluorophenyl)piperazine-1-carbonyl)-3-(2-(3-fluoropyrrolidin-1-yl)-2-oxoethyl)-5-methylthieno[2,3-d]pyrimidin-4(3H)-one;
6-(4-(3,5-dichlorophenyl)piperazine-1-carbonyl)-5-methyl-3-(2-oxo-2-(pyrrolidin-1-yl)ethyl)thieno[2,3-d]pyrimidin-4(3H)-one;
N-(2,4-difluorophenyl)-2-(6-(4-(2-fluorophenyl)piperazine-1-carbonyl)-5-methyl-4-oxothieno[2,3-d]pyrimidin-3(4H)-yl)acetamide;
2-(6-(4-(3-chlorophenyl)piperazine-1-carbonyl)-5-methyl-4-oxothieno[2,3-d]pyrimidin-3(4H)-yl)-N-(2,4-difluorophenyl)acetamide;
(S)-N-(3,5-difluorophenyl)-2-(6-(3-fluoropyrrolidine-1-carbonyl)-5-methyl-4-oxothieno[2,3-d]pyrimidin-3 (4H)-yl)acetamide; or
2-(6-(4-(2-fluorophenyl)piperazine-1-carbonyl)-5-methyl-4-oxothieno[2,3-d]pyrimidin-3(4H)-yl)-N-(4-(trifluoromethyl)phenyl)acetamide;
or a pharmaceutically acceptable salt of one of these.

20. The pharmaceutical composition of claim 1, wherein the compound is:
2-(6-(4-(3-chlorophenyl)piperazine-1-carbonyl)-5-methyl-4-oxothieno[2,3-d]pyrimidin-3(4H)-yl)-N,N-diethylacetamide;
2-(6-(4-(4-chlorophenyl)piperazine-1-carbonyl)-5-methyl-4-oxothieno[2,3-d]pyrimidin-3(4H)-yl)-N,N-diethylacetamide;
2-(6-(4-(3,4-dichlorophenyl)piperazine-1-carbonyl)-5-methyl-4-oxothieno[2,3-d]pyrimidin-3(4H)-yl)-N,N-diethylacetamide;
2-(6-(4-(4-chloro-3-(trifluoromethyl)phenyl)piperazine-1-carbonyl)-5-methyl-4-oxothieno[2,3-d]pyrimidin-3 (4H)-yl)-N,N-diethylacetamide;
N,N-diethyl-2-(5-methyl-4-oxo-6-(4-(4-(trifluoromethyl)phenyl)piperazine-1-carbonyl)thieno[2,3-d]pyrimidin-3(4H)-yl)acetamide;
N-tert-butyl-2-(6-(4-(4-chlorophenyl)piperazine-1-carbonyl)-5-methyl-4-oxothieno[2,3-d]pyrimidin-3(4H)-yl)acetamide;
N-tert-butyl-2-(6-(4-(3-chlorophenyl)piperazine-1-carbonyl)-5-methyl-4-oxothieno[2,3-d]pyrimidin-3(4H)-yl)acetamide;
2-(6-(4-(3,5-bis(trifluoromethyl)phenyl)piperazine-1-carbonyl)-5-methyl-4-oxothieno[2,3-d]pyrimidin-3(4H)-yl)-N-tert-butylacetamide;
N-cyclohexyl-2-(5-methyl-4-oxo-6-(4-phenylpiperazine-1-carbonyl)thieno[2,3-d]pyrimidin-3(4H)-yl)acetamide;
2-(6-(4-(4-chlorophenyl)piperazine-1-carbonyl)-5-methyl-4-oxothieno[2,3-d]pyrimidin-3(4H)-yl)-N-cyclohexylacetamide;
N-cyclohexyl-2-(6-(4-(3-fluorophenyl)piperazine-1-carbonyl)-5-methyl-4-oxothieno[2,3-d]pyrimidin-3(4H)-yl)acetamide;
N-cyclohexyl-2-(6-(4-(4-fluorophenyl)piperazine-1-carbonyl)-5-methyl-4-oxothieno[2,3-d]pyrimidin-3(4H)-yl)acetamide;
N-cyclohexyl-2-(6-(4-(2-fluorophenyl)piperazine-1-carbonyl)-5-methyl-4-oxothieno[2,3-d]pyrimidin-3(4H)-yl)acetamide;
2-(6-(4-(3-chlorophenyl)piperazine-1-carbonyl)-5-methyl-4-oxothieno[2,3-d]pyrimidin-3(4H)-yl)-N-cyclohexylacetamide;
N-cyclohexyl-2-(5-methyl-6-(4-(3-nitrophenyl)piperazine-1-carbonyl)-4-oxothieno[2,3-d]pyrimidin-3(4H)-yl)acetamide;
N-cyclohexyl-2-(5-methyl-4-oxo-6-(4-phenylpiperazine-1-carbonyl)thieno[2,3-d]pyrimidin-3(4H)-yl)propanamide;
N-cyclohexyl-2-(6-(4-(2-fluorophenyl)piperazine-1-carbonyl)-5-methyl-4-oxothieno[2,3-d]pyrimidin-3(4H)-yl)propanamide;
N-cyclopentyl-2-(6-(4-(2-fluorophenyl)piperazine-1-carbonyl)-5-methyl-4-oxothieno[2,3-d]pyrimidin-3(4H)-yl)acetamide;
2-(6-(4-(3-chlorophenyl)piperazine-1-carbonyl)-5-methyl-4-oxothieno[2,3-d]pyrimidin-3(4H)-yl)-N-cyclopentylacetamide;
2-(6-(4-(4-chloro-3-(trifluoromethyl)phenyl)piperazine-1-carbonyl)-5-methyl-4-oxothieno[2,3-d]pyrimidin-3 (4H)-yl)-N-cyclopentylacetamide;
N-cyclopentyl-2-(5-methyl-4-oxo-6-(4-phenylpiperazine-1-carbonyl)thieno[2,3-d]pyrimidin-3(4H)-yl)acetamide;
2-(6-(4-(4-chlorophenyl)piperazine-1-carbonyl)-5-methyl-4-oxothieno[2,3-d]pyrimidin-3(4H)-yl)-N-cyclopentylacetamide;
N-cyclopentyl-2-(5-methyl-4-oxo-6-(4-phenylpiperazine-1-carbonyl)thieno[2,3-d]pyrimidin-3(4H)-yl)propanamide;
N-cyclopentyl-2-(6-(4-(2-fluorophenyl)piperazine-1-carbonyl)-5-methyl-4-oxothieno[2,3-d]pyrimidin-3(4H)-yl)propanamide;
2-(6-(4-(2-fluorophenyl)piperazine-1-carbonyl)-5-methyl-4-oxothieno[2,3-d]pyrimidin-3(4H)-yl)-N-phenylacetamide;
2-(5-methyl-4-oxo-6-(4-phenylpiperazine-1-carbonyl)thieno[2,3-d]pyrimidin-3(4H)-yl)-N-phenylacetamide;
2-(6-(4-(3,5-bis(trifluoromethyl)phenyl)piperazine-1-carbonyl)-5-methyl-4-oxothieno[2,3-d]pyrimidin-3(4H)-yl)-N-phenylacetamide;
2-(6-(4-phenylpiperazine-1-carbonyl)-5-methyl-4-oxothieno[2,3-d]pyrimidin-3(4H)-yl)-N-(3,5-difluorophenyl)acetamide;
2-(6-(4-(2-fluorophenyl)piperazine-1-carbonyl)-5-methyl-4-oxothieno[2,3-d]pyrimidin-3(4H)-yl)-N-(3-(trifluoromethyl)phenyl)acetamide;
N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide;
3-(2-(3,5-bis(trifluoromethyl)phenylamino)-2-oxoethyl)-N,5-dimethyl-4-oxo-3,4-dihydrothieno[2,3-d]pyrimidine-6-carboxamide;
3-(2-(3,5-bis(trifluoromethyl)phenylamino)-2-oxoethyl)-N-tert-butyl-5-methyl-4-oxo-3,4-dihydrothieno[2,3-d]pyrimidine-6-carboxamide;

N-(3,5-bis(trifluoromethyl)phenyl)-2-(5-methyl-4-oxo-6-(piperidine-1-carbonyl)thieno[2,3-d]pyrimidin-3(4H)-yl)acetamide;

6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one;

6-(4-(3-chlorophenyl)-piperazine-1-carbonyl)-3-(2-(3,3-difluoropyrrolidin-1-yl)-2-oxoethyl)-5-methylthieno[2,3-d]pyrimidin-4(3H)-one; 6-(4-(2-fluorophenyl)piperazine-1-carbonyl)-5-methyl-3-(2-oxo-2-(piperidin-1-yl)ethyl)thieno[2,3-d]pyrimidin-4(3H)-one; or 6-(4-(2-fluorophenyl)piperazine-1-carbonyl)-5-methyl-3-(2-oxo-2-((4-trifluoromethyl)piperidin-1-yl)ethyl)thieno[2,3-d]pyrimidin-4(3H)-one;

or a pharmaceutically acceptable salt of one of these.

21. The method of claim 1, wherein Y is an optionally substituted phenyl.

22. A method to treat a condition treatable by inhibiting T-type by calcium channel activity, which method comprises administering to a subject in need of such treatment an amount of A pharmaceutical composition of claim 1 effective to ameliorate said condition.

23. The method of claim 1, wherein said condition is cardiovascular disease, epilepsy, or chronic or acute pain.

24. The method of claim 1, wherein X is an optionally substituted ethylene or an optionally substituted methylene.

25. The method of claim 24, wherein X is $CH_2C=O$, $CH_2CH_2$, $CH(CH_3)C=O$ or $CH_2$.

26. The method of claim 2, wherein said condition is chronic or acute pain.

27. The method of claim 21, wherein Y is phenyl, 2-fluorophenyl, 3-fluorophenyl or 4-fluorophenyl.

28. The method of claim 1, wherein Y is $N(R_5)(R_6)$.

29. The method of claim 28, wherein $R_5$ and $R_6$ are independently H, or an optionally substituted $C_{1-6}$ alkyl, $C_{1-6}$ heteroalkyl or $C_{6-10}$ aryl.

30. The method of claim 29, wherein $R_5$ and $R_6$ are independently H, or an optionally substituted methyl, ethyl, butyl, cyclohexyl, cyclopentyl, cyclopropyl or phenyl.

31. The method of claim 28, wherein $R_5$ and $R_6$ together with N to which they are attached form an optionally substituted 3-8 membered heterocyclic or 5-12 membered heteroaromatic ring.

32. The method of claim 31, wherein $R_5$ and $R_6$ together with N to which they are attached form a 5-6 membered heterocyclic ring.

33. The method of claim 1, wherein $R_1$ and $R_2$ together with N to which they are attached form an optionally substituted 3-8 membered heterocyclic or 5-12 membered heteroaromatic ring.

34. The method of claim 33, wherein $R_1$ and $R_2$ together with N to which they are attached form an optionally substituted pyrrolidinyl, piperidinyl, piperazinyl, morpholino, pyridinyl or pyrrolyl.

35. The method of claim 1, wherein $R_1$ and $R_2$ are independently H or an optionally substituted $C_{1-6}$ alkyl, $C_{1-6}$ heteroalkyl, $C_{5-12}$ heteroaryl or $C_{6-12}$ aryl-$C_{1-6}$ alkyl.

36. The method of claim 35, wherein $R_1$ and $R_2$ are independently H, methyl, butyl, phenyl or benzyl.

37. The method of claim 1, wherein $R_4$ is H.

38. The method of claim 1, wherein $R_3$ is H or methyl.

39. The method of claim 38, wherein the compound is of formula 1 and $R_3$ is methyl.

40. The method of claim 17, wherein the compound is of formula 2 and $R_3$ is H.

41. The method of claim 1, wherein the compound is:

2-(6-(4-(3-chlorophenyl)piperazine-1-carbonyl)-5-methyl-4-oxothieno[2,3-d]pyrimidin-3(4H)-yl)-N,N-diethylacetamide;

N,N-diethyl-2-(6-(4-(2-fluorophenyl)piperazine-1-carbonyl)-5-methyl-4-oxothieno[2,3-d]pyrimidin-3(4H)-yl)acetamide;

N,N-diethyl-2-(5-methyl-4-oxo-6-(4-phenylpiperazine-1-carbonyl)thieno[2,3-d]pyrimidin-3(4H)-yl)acetamide;

2-(6-(4-(2-chlorophenyl)piperazine-1-carbonyl)-5-methyl-4-oxothieno[2,3-d]pyrimidin-3(4H)-yl)-N,N-diethylacetamide;

2-(6-(4-(4-chlorophenyl)piperazine-1-carbonyl)-5-methyl-4-oxothieno[2,3-d]pyrimidin-3(4H)-yl)-N,N-diethylacetamide;

2-(6-(4-(3,4-dichlorophenyl)piperazine-1-carbonyl)-5-methyl-4-oxothieno[2,3-d]pyrimidin-3(4H)-yl)-N,N-diethylacetamide;

N,N-diethyl-2-(6-(4-(3-fluorophenyl)piperazine-1-carbonyl)-5-methyl-4-oxothieno[2,3-d]pyrimidin-3(4H)-yl)acetamide;

2-(6-(4-(4-chloro-3-(trifluoromethyl)phenyl)piperazine-1-carbonyl)-5-methyl-4-oxothieno[2,3-d]pyrimidin-3(4H)-yl)-N,N-diethylacetamide;

N,N-diethyl-2-(5-methyl-4-oxo-6-(4-(2-(trifluoromethyl)phenyl)piperazine-1-carbonyl)thieno[2,3-d]pyrimidin-3(4H)-yl)acetamide;

N,N-diethyl-2-(5-methyl-4-oxo-6-(4-(4-(trifluoromethyl)phenyl)piperazine-1-carbonyl)thieno[2,3-d]pyrimidin-3(4H)-yl)acetamide;

N-tert-butyl-2-(6-(4-(4-fluorophenyl)piperazine-1-carbonyl)-5-methyl-4-oxothieno[2,3-d]pyrimidin-3(4H)-yl)acetamide;

N-tert-butyl-2-(5-methyl-4-oxo-6-(4-(3-(trifluoromethyl)phenyl)piperazine-1-carbonyl)thieno[2,3-d]pyrimidin-3(4H)-yl)acetamide;

N-tert-butyl-2-(5-methyl-4-oxo-6-(4-phenylpiperazine-1-carbonyl)thieno[2,3-d]pyrimidin-3(4H)-yl)acetamide;

N-tert-butyl-2-(6-(4-(2-fluorophenyl)piperazine-1-carbonyl)-5-methyl-4-oxothieno[2,3-d]pyrimidin-3(4H)-yl)acetamide;

N-tert-butyl-2-(6-(4-(4-chlorophenyl)piperazine-1-carbonyl)-5-methyl-4-oxothieno[2,3-d]pyrimidin-3(4H)-yl)acetamide;

N-tert-butyl-2-(6-(4-(3-chlorophenyl)piperazine-1-carbonyl)-5-methyl-4-oxothieno[2,3-d]pyrimidin-3(4H)-yl)acetamide;

2-(6-(4-(3,5-bis(trifluoromethyl)phenyl)piperazine-1-carbonyl)-5-methyl-4-oxothieno[2,3-d]pyrimidin-3(4H)-yl)-N-tert-butylacetamide;

N-cyclohexyl-2-(5-methyl-4-oxo-6-(4-tertbutylpiperazine-1-carbonyl)thieno[2,3-d]pyrimidin-3(4H)-yl)acetamide;

N-cyclohexyl-2-(5-methyl-4-oxo-6-(4-phenylpiperazine-1-carbonyl)thieno[2,3-d]pyrimidin-3(4H)-yl)acetamide;

2-(6-(4-(4-chlorophenyl)piperazine-1-carbonyl)-5-methyl-4-oxothieno[2,3-d]pyrimidin-3(4H)-yl)-N-cyclohexylacetamide;

N-cyclohexyl-2-(6-(4-(3-fluorophenyl)piperazine-1-carbonyl)-5-methyl-4-oxothieno[2,3-d]pyrimidin-3(4H)-yl)acetamide;

N-cyclohexyl-2-(6-(4-(4-fluorophenyl)piperazine-1-carbonyl)-5-methyl-4-oxothieno[2,3-d]pyrimidin-3(4H)-yl)acetamide;

N-cyclohexyl-2-(6-(4-(2-fluorophenyl)piperazine-1-carbonyl)-5-methyl-4-oxothieno[2,3-d]pyrimidin-3(4H)-yl)acetamide;

2-(6-(4-(3-chlorophenyl)piperazine-1-carbonyl)-5-methyl-4-oxothieno[2,3-d]pyrimidin-3(4H)-yl)-N-cyclohexylacetamide;

N-cyclohexyl-2-(6-(4-(3,4-dichlorophenyl)piperazine-1-carbonyl)-5-methyl-4-oxothieno[2,3-d]pyrimidin-3(4H)-yl)acetamide;

N-cyclohexyl-2-(5-methyl-4-oxo-6-(piperidine-1-carbonyl)thieno[2,3-d]pyrimidin-3(4H)-yl)acetamide;

N-cyclohexyl-2-(6-(4-(3-methoxyphenyl)piperazine-1-carbonyl)-5-methyl-4-oxothieno[2,3-d]pyrimidin-3(4H)-yl)acetamide;

N-cyclohexyl-2-(5-methyl-6-(4-(4-methoxy phenyl)piperazine-1-carbonyl)-4-oxothieno[2,3-d]pyrimidin-3(4H)-yl)acetamide;

N-cyclohexyl-2-(5-methyl-6-(4-(3-nitrophenyl)piperazine-1-carbonyl)-4-oxothieno[2,3-d]pyrimidin-3(4H)-yl)acetamide;

N-(4,4-difluorocyclohexyl)-2-(5-methyl-4-oxo-6-(4-(phenyl)piperazine-1-carbonyl)thieno[2,3-d]pyrimidin-3(4H)-yl)acetamide;

N-(4,4-difluorocyclohexyl)-2-(5-methyl-4-oxo-6-(4-(2-fluorophenyl)piperazine-1-carbonyl)thieno[2,3-d]pyrimidin-3(4H)-yl)acetamide;

N-(4,4-difluorocyclohexyl)-2-(5-methyl-4-oxo-6-(4-(3-chlorophenyl)piperazine-1-carbonyl)thieno[2,3-d]pyrimidin-3(4H)-yl)acetamide;

N-cyclohexyl-2-(5-methyl-4-oxo-6-(4-phenylpiperazine-1-carbonyl)thieno[2,3-d]pyrimidin-3(4H)-yl)propanamide;

N-cyclohexyl-2-(6-(4-(2-fluorophenyl)piperazine-1-carbonyl)-5-methyl-4-oxothieno[2,3-d]pyrimidin-3(4H)-yl)propanamide;

N-cyclohexyl-2-(6-(4-(3-chlorophenyl)piperazine-1-carbonyl)-5-methyl-4-oxothieno[2,3-d]pyrimidin-3(4H)-yl)propanamide;

N-cyclopentyl-2-(6-(4-(2-fluorophenyl)piperazine-1-carbonyl)-5-methyl-4-oxothieno[2,3-d]pyrimidin-3(4H)-yl)acetamide;

2-(6-(4-(3-chlorophenyl)piperazine-1-carbonyl)-5-methyl-4-oxothieno[2,3-d]pyrimidin-3(4H)-yl)-N-cyclopentylacetamide;

2-(6-(4-(4-chloro-3-(trifluoromethyl)phenyl)piperazine-1-carbonyl)-5-methyl-4-oxothieno[2,3-d]pyrimidin-3(4H)-yl)-N-cyclopentylacetamide;

N-cyclopentyl-2-(5-methyl-6-(4-methylpiperazine-1-carbonyl)-4-oxothieno[2,3-d]pyrimidin-3(4H)-yl)acetamide;

N-cyclopentyl-2-(5-methyl-6-(4-tertbutylpiperazine-1-carbonyl)-4-oxothieno[2,3-d]pyrimidin-3(4H)-yl)acetamide;

N-cyclopentyl-2-(5-methyl-4-oxo-6-(4-phenylpiperazine-1-carbonyl)thieno[2,3-d]pyrimidin-3(4H)-yl)acetamide;

2-(6-(4-(4-chlorophenyl)piperazine-1-carbonyl)-5-methyl-4-oxothieno[2,3-d]pyrimidin-3(4H)-yl)-N-cyclopentylacetamide;

N-cyclopentyl-2-(6-(4-(3-methoxyphenyl)piperazine-1-carbonyl)-5-methyl-4-oxothieno[2,3-d]pyrimidin-3(4H)-yl)acetamide;

N-cyclopentyl-2-(6-(4-(4-methoxyphenyl)piperazine-1-carbonyl)-5-methyl-4-oxothieno[2,3-d]pyrimidin-3(4H)-yl)acetamide;

N-cyclopentyl-2-(6-(4-(3-nitrophenyl)piperazine-1-carbonyl)-5-methyl-4-oxothieno[2,3-d]pyrimidin-3(4H)-yl)acetamide;

N-cyclopentyl-2-(5-methyl-4-oxo-6-(4-phenylpiperazine-1-carbonyl)thieno[2,3-d]pyrimidin-3(4H)-yl)propanamide;

N-cyclopentyl-2-(6-(4-(2-fluorophenyl)piperazine-1-carbonyl)-5-methyl-4-oxothieno[2,3-d]pyrimidin-3(4H)-yl)propanamide;

N-cyclopentyl-2-(6-(4-(4-fluorophenyl)piperazine-1-carbonyl)-5-methyl-4-oxothieno[2,3-d]pyrimidin-3(4H)-yl)propanamide;

N-cyclopropyl-2-(5-methyl-4-oxo-6-(4-phenylpiperazine-1-carbonyl)thieno[2,3-d]pyrimidin-3(4H)-yl)acetamide;

N-cyclopropyl-2-(6-(4-(2-fluorophenyl)piperazine-1-carbonyl)-5-methyl-4-oxothieno[2,3-d]pyrimidin-3(4H)-yl)acetamide;

2-(6-(4-(2-fluorophenyl)piperazine-1-carbonyl)-5-methyl-4-oxothieno[2,3-d]pyrimidin-3(4H)-yl)-N-phenylacetamide;

2-(5-methyl-4-oxo-6-(4-phenylpiperazine-1-carbonyl)thieno[2,3-d]pyrimidin-3(4H)-yl)-N-phenylacetamide;

2-(6-(4-(3,5-bis(trifluoromethyl)phenyl)piperazine-1-carbonyl)-5-methyl-4-oxothieno[2,3-d]pyrimidin-3(4H)-yl)-N-phenylacetamide;

2-(5-methyl-6-(4-methylpiperazine-1-carbonyl)-4-oxothieno[2,3-d]pyrimidin-3(4H)-yl)-N-phenylacetamide;

2-(6-(4-phenylpiperazine-1-carbonyl)-5-methyl-4-oxothieno[2,3-d]pyrimidin-3(4H)-yl)-N-(3,5-difluorophenyl)acetamide;

2-(6-(4-(3-chlorophenyl)piperazine-1-carbonyl)-5-methyl-4-oxothieno[2,3-d]pyrimidin-3(4H)-yl)-N-(3,5-difluorophenyl)acetamide;

(S)-N-(3,5-difluorophenyl)-2-(6-(3-fluoropyrrolidin-1-carbonyl)-5-methyl-4-oxothieno[2,3-d]pyrimidin-3(4H)-yl)acetamide;

(S)-N-(3,5-difluorophenyl)-2-(6-(3,3-difluoropyrrolidin-1-carbonyl)-5-methyl-4-oxothieno[2,3-d]pyrimidin-3(4H)-yl)acetamide;

N-(3,5-difluorophenyl)-2-(6-(4-fluoropiperidin-1-carbonyl)-5-methyl-4-oxothieno[2,3-d]pyrimidin-3(4H)-yl)acetamide;

N-(3,5-difluorophenyl)-2-(6-(4,4-difluoropiperidin-1-carbonyl)-5-methyl-4-oxothieno[2,3-d]pyrimidin-3(4H)-yl)acetamide;

N-(3,5-difluorophenyl)-2-(6-(3,3-difluoropiperidin-1-carbonyl)-5-methyl-4-oxothieno[2,3-d]pyrimidin-3(4H)-yl)acetamide;

2-(6-(4-(2-fluorophenyl)piperazine-1-carbonyl)-5-methyl-4-oxothieno[2,3-d]pyrimidin-3(4H)-yl)-N-(3-(trifluoromethyl)phenyl)acetamide;

2-(5-methyl-(4-oxo-6-(4-(trifluoromethyl)piperidin-1-carbonyl)thieno[2,3-d]pyrimidin-3(4H)-yl)-N-(3-(trifluoromethyl)phenyl)acetamide;

N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide;

N-(3,5-bis(trifluoromethyl)phenyl)-2-(5-methyl-4-oxo-6-(piperazine-1-carbonyl)thieno[2,3-d]pyrimidin-3(4H)-yl)acetamide;

3-(2-(3,5-bis(trifluoromethyl)phenylamino)-2-oxoethyl)-N,5-dimethyl-4-oxo-3,4-dihydrothieno[2,3-d]pyrimidine-6-carboxamide;

3-(2-(3,5-bis(trifluoromethyl)phenylamino)-2-oxoethyl)-5-methyl-4-oxo-3,4-dihydrothieno[2,3-d]pyrimidine-6-carboxamide;

3-(2-(3,5-bis(trifluoromethyl)phenylamino)-2-oxoethyl)-N-tert-butyl-5-methyl-4-oxo-3,4-dihydrothieno[2,3-d]pyrimidine-6-carboxamide;

N-(3,5-bis(trifluoromethyl)phenyl)-2-(5-methyl-4-oxo-6-(piperidine-1-carbonyl)thieno[2,3-d]pyrimidin-3(4H)-yl)acetamide;

N-(3,5-bis(trifluoromethyl)phenyl)-2-(5-methyl-4-oxo-6-(pyrrolidine-1-carbonyl)thieno[2,3-d]pyrimidin-3(4H)-yl)acetamide;

(S)-N-(3,5-bis(trifluoromethyl)phenyl)-2-(5-methyl-4-oxo-6-(3-fluoropyrrolidine-1-carbonyl)thieno[2,3-d]pyrimidin-3(4H)-yl)acetamide;

N-(3,5-bis(trifluoromethyl)phenyl)-2-(5-methyl-4-oxo-6-(4-fluoropiperidine-1-carbonyl)thieno[2,3-d]pyrimidin-3(4H)-yl)acetamide;

6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one;

5-methyl-3-(2-oxo-2-(pyrrolidin-1-yl)ethyl)-6-(4-phenylpiperazine-1-carbonyl)thieno[2,3-d]pyrimidin-4(3H)-one;

(R)-6-(4-(3-chlorophenyl)-piperazine-1-carbonyl)-3-(2-(3-fluoropyrrolidin-1-yl)-2-oxoethyl)-5-methylthieno[2,3-d]pyrimidin-4(3H)-one;

(S)-6-(4-(3-chlorophenyl)-piperazine-1-carbonyl)-3-(2-(3-fluoropyrrolidin-1-yl)-2-oxoethyl)-5-methylthieno[2,3-d]pyrimidin-4(3H)-one;

(S)-6-(4-(2-fluorophenyl)-piperazine-1-carbonyl)-3-(2-(3-fluoropyrrolidin-1-yl)-2-oxoethyl)-5-methylthieno[2,3-d]pyrimidin-4(3H)-one;

6-(4-(3-chlorophenyl)-piperazine-1-carbonyl)-3-(2-(3,3-difluoropyrrolidin-1-yl)-2-oxoethyl)-5-methylthieno[2,3-d]pyrimidin-4(3H)-one;

3-(2-(3,3-difluoropyrrolidin-1-yl)-2-oxoethyl)-6-(4-(2-fluorophenyl)piperazine-1-carbonyl)-5-methylthieno[2,3-d]pyrimidin-4(3H)-one;

6-(4-(3-chlororophenyl)piperazine-1-carbonyl)-5-methyl-3-(2-oxo-2-(2-trifluoromethyl)pyrrolidin-1-yl)ethyl)thieno[2,3-d]pyrimidin-4(3H)-one;

6-(4-(2-fluorophenyl)piperazine-1-carbonyl)-5-methyl-3-(2-oxo-2-(piperidin-1-yl)ethyl)thieno[2,3-d]pyrimidin-4(3H)-one;

6-(4-(3-chlorophenyl)piperazine-1-carbonyl)-5-methyl-3-(2-(3-methylpiperidin-1-yl)-2-oxoethyl)thieno[2,3-d]pyrimidin-4(3H)-one;

6-(4-(2-fluorophenyl)piperazine-1-carbonyl)-5-methyl-3-(2-(4-methylpiperidin-1-yl)-2-oxoethyl)thieno[2,3-d]pyrimidin-4(3H)-one;

4-(2-(4-fluoropiperidin-1-yl)-2-oxoethyl)-6-(4-(3-chlorophenyl)piperazine-1-carbonyl)-5-methylthieno[2,3-d]pyrimidin-4(3H)-one;

3-(2-(3,3-difluoropiperidin-1-yl)-2-oxoethyl)-6-(4-(2-fluorophenyl)piperazine-1-carbonyl)-5-methylthieno[2,3-d]pyrimidin-4(3H)-one;

3-(2-(3,3-difluoropiperidin-1-yl)-2-oxoethyl)-6-(4-(3-chlorophenyl)piperazine-1-carbonyl)-5-methylthieno[2,3-d]pyrimidin-4(3H)-one;

6-(4-(3-chlorophenyl)piperazine-1-carbonyl)-3-(2-(4,4-difluoropiperidin-1-yl)-2-oxoethyl)-5-methylthieno[2,3-d]pyrimidin-4(3H)-one;

3-(2-(4,4-difluoropiperidin-1-yl)-2-oxoethyl)-6-(4-(2-fluorophenyl)piperazine-1-carbonyl)-5-methylthieno[2,3-d]pyrimidin-4(3H)-one;

6-(4-(2-fluorophenyl)piperazine-1-carbonyl)-5-methyl-3-(2-oxo-2-((4-trifluoromethyl)piperidin-1-yl)ethyl)thieno[2,3-d]pyrimidin-4(3H)-one;

3-(2-(3,3-difluoropiperidin-1-yl)-2-oxoethyl)-6-(4-(4-fluorophenyl)piperazine-1-carbonyl)-5-methylthieno[2,3-d]pyrimidin-4(3H)-one;

(S)-6-(4-(4-fluorophenyl)-piperazine-1-carbonyl)-3-(2-(3-fluoropyrrolidin-1-yl)-2-oxoethyl)-5-methylthieno[2,3-d]pyrimidin-4(3H)-one;

5-methyl-3-(2-(2-oxopyrrolidin-1-yl)ethyl)-6-(4-phenylpiperazine-1-carbonyl)thieno[2,3-d]pyrimidin-4(3H)-one;

6-(4-(3,5-bis(trifluoromethyl)phenyl)piperazine-1-carbonyl)-5-methyl-3-(2-(2-oxopyrrolidin-1-yl)ethyl)thieno[2,3-d]pyrimidin-4(3H)-one;

6-(4-(4-chlorophenyl)piperazine-1-carbonyl)-5-methyl-3-(2-(2-oxopyrrolidin-1-yl)ethyl)thieno[2,3-d]pyrimidin-4(3H)-one;

6-(4-(2-fluorophenyl)piperazine-1-carbonyl)-5-methyl-3-(2-(2-oxopyrrolidin-1-yl)ethyl)thieno[2,3-d]pyrimidin-4(3H)-one;

2-(5-methyl-4-oxo-6-(4-phenylpiperazine-1-carbonyl)thieno[2,3-d]pyrimidin-3(4H)-yl)-N-(2,2,2-trifluoroethyl)acetamide;

3-benzyl-N,N,5-trimethyl-4-oxo-3,4-dihydrothieno[2,3-d]pyrimidine-6-carboxamide;

3-(2-fluorobenzyl)-N,N,5-trimethyl-4-oxo-3,4-dihydrothieno[2,3-d]pyrimidine-6-carboxamide;

6-(3,5-dimethylpiperazine-1-carbonyl)-3-(2-fluorobenzyl)-5-methylthieno[2,3-d]pyrimidin-4(3H)-one;

3-(2-fluorobenzyl)-5-methyl-6-(piperazine-1-carbonyl)thieno[2,3-d]pyrimidin-4(3H)-one;

6-(4-(3-chlorophenyl)piperazine-1-carbonyl)-3-(2-fluorobenzyl)-5-methyl thieno[2,3-d]pyrimidin-4(3H)-one;

6-(4-(4-fluorobenzoyl)piperazine-1-carbonyl)-3-(2-fluorobenzyl)-5-methylthieno[2,3-d]pyrimidin-4(3H)-one;

3-(2-fluorobenzyl)-5-methyl-6-(4-(3,4,5-trimethoxybenzoyl)piperazine-1-carbonyl)thieno[2,3-d]pyrimidin-4(3H)-one;

3-(2-(4-(3-chlorophenyl)piperazine-1-yl)-2-oxoethyl)-5-methyl-6-(pyrrolidine-1-carbonyl)thieno[2,3-d]pyrimidin-4(3H)-one;

(S)-3-(2-(4-(3-chlorophenyl)piperazine-1-yl)-2-oxoethyl)-5-methyl-6-(3-fluoro pyrrolidine-1-carbonyl)thieno[2,3-d]pyrimidin-4(3H)-one;

3-(2-(4-(3-chlorophenyl)piperazine-1-yl)-2-oxoethyl)-6-(3,3-difluoro pyrrolidine-1-carbonyl)-5-methylthieno[2,3-d]pyrimidin-4(3H)-one;

3-(2-(4-(3-chlorophenyl)piperazine-1-yl)-2-oxoethyl)-6-(3,3-difluoro piperidine-1-carbonyl)-5-methylthieno[2,3-d]pyrimidin-4(3H)-one;

6-(4,4-difluoropiperidine-1-carbonyl)-3-(2-(4-(2-fluorophenyl)piperazin-1-yl)-2-oxoethyl)-5-methylthieno[2,3-d]pyrimidin-4(3H)-one;

N-ethyl-2-(6-(4-(2-fluorophenyl)piperazine-1-carbonyl)-5-methyl-4-oxothieno[2,3-d]pyrimidin-3(4H)-yl)-N-(2,2,2-trifluoroethyl)acetamide;

N-ethyl-2-(6-(4-(phenyl piperazine-1-carbonyl)-5-methyl-4-oxothieno[2,3-d]pyrimidin-3(4H)-yl)-N-(2,2,2-trifluoroethyl)acetamide;

N-ethyl-2-(6-(4-(3-chlorophenyl)piperazine-1-carbonyl)-5-methyl-4-oxothieno[2,3-d]pyrimidin-3(4H)-yl)-N-(2,2,2-trifluoroethyl)acetamide;

2-(6-(4-(3-chlorophenyl)piperazine-1-carbonyl)-5-methyl-4-oxothieno[2,3-d]pyrimidin-3(4H)-yl)-N-ethyl-N-(2,2,2-trifluoroethyl)acetamide;

N-ethyl-2-(6-(4-(4-fluorophenyl)piperazine-1-carbonyl)-5-methyl-4-oxothieno[2,3-d]pyrimidin-3(4H)-yl)-N-(2,2,2-trifluoroethyl)acetamide;

N-ethyl-2-(5-methyl-4-oxo-6-(4-phenylpiperazine-1-carbonyl)thieno[2,3-d]pyrimidin-3(4H)-yl)-N-(2,2,2-trifluoroethyl)acetamide;
N-ethyl-2-(5-methyl-4-oxo-6-(4-(4-(trifluoromethyl)phenyl)piperazine-1-carbonyl)thieno[2,3-d]pyrimidin-3(4H)-yl)-N-(2,2,2-trifluoroethyl)acetamide;
N-tert-butyl-2-(6-(4-(3-chloro-4-fluorophenyl)piperazine-1-carbonyl)-5-methyl-4-oxothieno[2,3-d]pyrimidin-3(4H)-yl)acetamide;
N-tert-butyl-2-(6-(4-(3,4-dichlorophenyl)piperazine-1-carbonyl)-5-methyl-4-oxothieno[2,3-d]pyrimidin-3(4H)-yl)acetamide;
2-(6-(4-(3-chloro-4-fluorophenyl)piperazine-1-carbonyl)-5-methyl-4-oxothieno[2,3-d]pyrimidin-3(4H)-yl)-N-cyclohexylacetamide;
6-(4-(3-chloro-4-fluorophenyl)piperazine-1-carbonyl)-5-methyl-3-(2-oxo-2-(pyrrolidin-1-yl)ethyl)thieno[2,3-d]pyrimidin-4(3H)-one;
6-(4-(3,4-dichlorophenyl)piperazine-1-carbonyl)-5-methyl-3-(2-oxo-2-(pyrrolidin-1-yl)ethyl)thieno[2,3-d]pyrimidin-4(3H)-one;
6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one;
(S)-6-(4-(3-chloro-4-fluorophenyl)piperazine-1-carbonyl)-3-(2-(3-fluoropyrrolidin-1-yl)-2-oxoethyl)-5-methylthieno[2,3-d]pyrimidin-4(3H)-one;
6-(4-(3,5-dichlorophenyl)piperazine-1-carbonyl)-5-methyl-3-(2-oxo-2-(pyrrolidin-1-yl)ethyl)thieno[2,3-d]pyrimidin-4(3H)-one;
N-(2,4-difluorophenyl)-2-(6-(4-(2-fluorophenyl)piperazine-1-carbonyl)-5-methyl-4-oxothieno[2,3-d]pyrimidin-3(4H)-yl)acetamide;
2-(6-(4-(3-chlorophenyl)piperazine-1-carbonyl)-5-methyl-4-oxothieno[2,3-d]pyrimidin-3(4H)-yl)-N-(2,4-difluorophenyl)acetamide;
(S)-N-(3,5-difluorophenyl)-2-(6-(3-fluoropyrrolidine-1-carbonyl)-5-methyl-4-oxothieno[2,3-d]pyrimidin-3(4H)-yl)acetamide; or
2-(6-(4-(2-fluorophenyl)piperazine-1-carbonyl)-5-methyl-4-oxothieno[2,3-d]pyrimidin-3(4H)-yl)-N-(4-(trifluoromethyl)phenyl)acetamide;
or a pharmaceutically acceptable salt of one of these.

42. The method of claim 1, wherein the compound is:
2-(6-(4-(3-chlorophenyl)piperazine-1-carbonyl)-5-methyl-4-oxothieno[2,3-d]pyrimidin-3(4H)-yl)-N,N-diethylacetamide;
2-(6-(4-(4-chlorophenyl)piperazine-1-carbonyl)-5-methyl-4-oxothieno[2,3-d]pyrimidin-3(4H)-yl)-N,N-diethylacetamide;
2-(6-(4-(3,4-dichlorophenyl)piperazine-1-carbonyl)-5-methyl-4-oxothieno[2,3-d]pyrimidin-3(4H)-yl)-N,N-diethylacetamide;
2-(6-(4-(4-chloro-3-(trifluoromethyl)phenyl)piperazine-1-carbonyl)-5-methyl-4-oxothieno[2,3-d]pyrimidin-3(4H)-yl)-N,N-diethylacetamide;
N,N-diethyl-2-(5-methyl-4-oxo-6-(4-(4-(trifluoromethyl)phenyl)piperazine-1-carbonyl)thieno[2,3-d]pyrimidin-3(4H)-yl)acetamide;
N-tert-butyl-2-(6-(4-(4-chlorophenyl)piperazine-1-carbonyl)-5-methyl-4-oxothieno[2,3-d]pyrimidin-3(4H)-yl)acetamide;
N-tert-butyl-2-(6-(4-(3-chlorophenyl)piperazine-1-carbonyl)-5-methyl-4-oxothieno[2,3-d]pyrimidin-3(4H)-yl)acetamide;
2-(6-(4-(3,5-bis(trifluoromethyl)phenyl)piperazine-1-carbonyl)-5-methyl-4-oxothieno[2,3-d]pyrimidin-3(4H)-yl)-N-tert-butylacetamide;
N-cyclohexyl-2-(5-methyl-4-oxo-6-(4-phenylpiperazine-1-carbonyl)thieno[2,3-d]pyrimidin-3(4H)-yl)acetamide;
2-(6-(4-(4-chlorophenyl)piperazine-1-carbonyl)-5-methyl-4-oxothieno[2,3-d]pyrimidin-3(4H)-yl)-N-cyclohexylacetamide;
N-cyclohexyl-2-(6-(4-(3-fluorophenyl)piperazine-1-carbonyl)-5-methyl-4-oxothieno[2,3-d]pyrimidin-3(4H)-yl)acetamide;
N-cyclohexyl-2-(6-(4-(4-fluorophenyl)piperazine-1-carbonyl)-5-methyl-4-oxothieno[2,3-d]pyrimidin-3(4H)-yl)acetamide;
N-cyclohexyl-2-(6-(4-(2-fluorophenyl)piperazine-1-carbonyl)-5-methyl-4-oxothieno[2,3-d]pyrimidin-3(4H)-yl)acetamide;
2-(6-(4-(3-chlorophenyl)piperazine-1-carbonyl)-5-methyl-4-oxothieno[2,3-d]pyrimidin-3(4H)-yl)-N-cyclohexylacetamide;
N-cyclohexyl-2-(5-methyl-6-(4-(3-nitrophenyl)piperazine-1-carbonyl)-4-oxothieno[2,3-d]pyrimidin-3(4H)-yl)acetamide;
N-cyclohexyl-2-(5-methyl-4-oxo-6-(4-phenylpiperazine-1-carbonyl)thieno[2,3-d]pyrimidin-3(4H)-yl)propanamide;
N-cyclohexyl-2-(6-(4-(2-fluorophenyl)piperazine-1-carbonyl)-5-methyl-4-oxothieno[2,3-d]pyrimidin-3(4H)-yl)propanamide;
N-cyclopentyl-2-(6-(4-(2-fluorophenyl)piperazine-1-carbonyl)-5-methyl-4-oxothieno[2,3-d]pyrimidin-3(4H)-yl)acetamide;
2-(6-(4-(3-chlorophenyl)piperazine-1-carbonyl)-5-methyl-4-oxothieno[2,3-d]pyrimidin-3(4H)-yl)-N-cyclopentylacetamide;
2-(6-(4-(4-chloro-3-(trifluoromethyl)phenyl)piperazine-1-carbonyl)-5-methyl-4-oxothieno[2,3-d]pyrimidin-3(4H)-yl)-N-cyclopentylacetamide;
N-cyclopentyl-2-(5-methyl-4-oxo-6-(4-phenylpiperazine-1-carbonyl)thieno[2,3-d]pyrimidin-3(4H)-yl)acetamide;
2-(6-(4-(4-chlorophenyl)piperazine-1-carbonyl)-5-methyl-4-oxothieno[2,3-d]pyrimidin-3(4H)-yl)-N-cyclopentylacetamide;
N-cyclopentyl-2-(5-methyl-4-oxo-6-(4-phenylpiperazine-1-carbonyl)thieno[2,3-d]pyrimidin-3(4H)-yl)propanamide;
N-cyclopentyl-2-(6-(4-(2-fluorophenyl)piperazine-1-carbonyl)-5-methyl-4-oxothieno[2,3-d]pyrimidin-3(4H)-yl)propanamide;
2-(6-(4-(2-fluorophenyl)piperazine-1-carbonyl)-5-methyl-4-oxothieno[2,3-d]pyrimidin-3(4H)-yl)-N-phenylacetamide;
2-(5-methyl-4-oxo-6-(4-phenylpiperazine-1-carbonyl)thieno[2,3-d]pyrimidin-3(4H)-yl)-N-phenylacetamide;
2-(6-(4-(3,5-bis(trifluoromethyl)phenyl)piperazine-1-carbonyl)-5-methyl-4-oxothieno[2,3-d]pyrimidin-3(4H)-yl)-N-phenylacetamide;
2-(6-(4-phenylpiperazine-1-carbonyl)-5-methyl-4-oxothieno[2,3-d]pyrimidin-3(4H)-yl)-N-(3,5-difluorophenyl)acetamide;
2-(6-(4-(2-fluorophenyl)piperazine-1-carbonyl)-5-methyl-4-oxothieno[2,3-d]pyrimidin-3(4H)-yl)-N-(3-(trifluoromethyl)phenyl)acetamide;

N-(3,5-bis(trifluoromethyl)phenyl)-2-(6-(4-(2-fluorophenyl)piperazine-1-carbonyl)-5-methyl-4-oxothieno[2,3-d]pyrimidin-3(4H)-yl)acetamide;

3-(2-(3,5-bis(trifluoromethyl)phenylamino)-2-oxoethyl)-N,5-dimethyl-4-oxo-3,4-dihydrothieno[2,3-d]pyrimidine-6-carboxamide;

3-(2-(3,5-bis(trifluoromethyl)phenylamino)-2-oxoethyl)-N-tert-butyl-5-methyl-4-oxo-3,4-dihydrothieno[2,3-d]pyrimidine-6-carboxamide;

N-(3,5-bis(trifluoromethyl)phenyl)-2-(5-methyl-4-oxo-6-(piperidine-1-carbonyl)thieno[2,3-d]pyrimidin-3(4H)-yl)acetamide;

6-(4-(3-chlorophenyl)piperazine-1-carbonyl)-5-methyl-3-(2-oxo-2-(pyrrolidin-1-yl)ethyl)thieno[2,3-d]pyrimidin-4(3H)-one;

6-(4-(3-chlorophenyl)-piperazine-1-carbonyl)-3-(2-(3,3-difluoropyrrolidin-1-yl)-2-oxoethyl)-5-methylthieno[2,3-d]pyrimidin-4(3H)-one;  6-(4-(2-fluorophenyl)piperazine-1-carbonyl)-5-methyl-3-(2-oxo-2-(piperidin-1-yl)ethyl)thieno[2,3-d]pyrimidin-4(3H)-one; or 6-(4-(2-fluorophenyl)piperazine-1-carbonyl)-5-methyl-3-(2-oxo-2-((4-trifluoromethyl)piperidin-1-yl)ethyl)thieno[2,3-d]pyrimidin-4(3H)-one;

or a pharmaceutically acceptable salt of one of these.

\* \* \* \* \*